US011896655B2

(12) United States Patent
Pancera et al.

(10) Patent No.: US 11,896,655 B2
(45) Date of Patent: Feb. 13, 2024

(54) CIRCUMSPOROZOITE PROTEINS WITH INCREASED EXPRESSION IN MAMMALIAN CELLS

(71) Applicant: Fred Hutchinson Cancer Center, Seattle, WA (US)

(72) Inventors: Marie Pancera, Seattle, WA (US); Connor Weidle, Mill Creek, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 125 days.

(21) Appl. No.: 17/440,597

(22) PCT Filed: Mar. 18, 2020

(86) PCT No.: PCT/US2020/023375
§ 371 (c)(1),
(2) Date: Sep. 17, 2021

(87) PCT Pub. No.: WO2020/191060
PCT Pub. Date: Sep. 24, 2020

(65) Prior Publication Data
US 2022/0280626 A1    Sep. 8, 2022

Related U.S. Application Data

(60) Provisional application No. 62/820,087, filed on Mar. 18, 2019.

(51) Int. Cl.
*A61K 39/002* (2006.01)
*A61K 39/015* (2006.01)
*A61P 33/06* (2006.01)
*A61K 31/355* (2006.01)
*A61K 39/00* (2006.01)

(52) U.S. Cl.
CPC .......... *A61K 39/015* (2013.01); *A61K 31/355* (2013.01); *A61P 33/06* (2018.01); *A61K 2039/52* (2013.01); *A61K 2039/627* (2013.01)

(58) Field of Classification Search
None
See application file for complete search history.

(56) References Cited

PUBLICATIONS

Kisalu, et al., "A human antibody prevents malaria infection and defines a new site of vulnerability on Plasmodium falciparum circumsporozite protein," Nat. Med. vol. 24, No. 4, 2018, pp. 408-416.
Pardi, et al., "Nucleoside-modified mRNA immunization elicits influenza virus hemugglutinin stalk-specific antibodies," Nat. Comm., vol. 9, No. 3361, 2018, 12 pages.
Search Report and Written Opinion dated Jun. 18, 2020 for International Application No. PCT/US20/23375, 5 pages.
Adams, et al., "The Thrombospondin Type 1 Repeat (TSR) Superfamily: Diverse Proteins With Related Roles in Neuronal Development." Developmental Dynamics, vol. 218, 2000, pp. 280-299.
Battye, et al., "iMOSFLM: a new graphical interface for diffractionimage processing with MOSFLM,"Acta Crystallographica Section D, vol. D67, 2011, pp. 271-281.
Bibikova, et al., "Enhancing Gene Targeting with Designed Zinc Finger Nucleases," Science, vol. 300, 2003, 2 pages.
Bibikova, et al., "Targeted Chromosomal Cleavage and Mutagenesis in Drosophila Using Zinc-Finger Nucleases," Genetics, vol. 161, 2002, pp. 1169-1175.
Bongfen, et al., "The N-terminal domain of Plasmodium falciparum circumsporozoite protein represents a target of protective immunity," Vaccine, vol. 27, No. 2, 1009, pp. 328-335.
Borst, et al., "Germline VRC01 antibody recognition of a modified clade C HIV-1 envelope trimer and a glycosylated HIV-1 gp120 core," eLife, vol. 7, No. e37688, 2018, 32 pages.
Coppi, et al., "The malaria circumsporozoite protein has two functional domains, each with distinct roles as sporozoites journey from mosquito to mammalian host," The Journal of Experimental Medicine, vol. 208, No. 2, 2011, pp. 341-356.
Coppi, et al., "The Plasmodium circumsporozoite protein is proteolytically processed during cell invasion," The Journal of Experimantal Medicine, vol. 201, No. 1, 2005, pp. 27-33.
Cullis, et al., "Lipid polymorphism and the roles of lipids in membranes ," Chem. Phys. Lip., vol. 40, No. 2-4, 1986, pp. 127-144.
De Koning-Ward, et al., "A New Rodent Model to Assess Blood Stage Immunity to the Plasmodium falciparum Antigen Merozoite Surface Protein 1(19) Reveals a Protective Role for Invasion Inhibitory Antibodies," J. Exp. Med., vol. 198, No. 6, 2003, pp. 869-875.
Doud, et al., "Unexpected fold in the circumsporozoite protein target of malaria vaccines," PNAS, vol. 109, No. 20, 2012, pp. 7817-7822.
Foquet, et al., "Vaccine-induced monoclonal antibodies targeting circumsporozoite protein prevent Plasmodium falciparum infection," The Journal of Clinical Investigation, vol. 124, No. 1, 2014, pp. 140-144.
Gandhi, et al., "Variation in the Circumsporozoite Protein of Plasmodium falciparum: Vaccine Development Implications," PLOS One, vol. 9, No. 7, 2014, 9 pages.
Grant, et al., "cisTEM, user-friendly software for single- particle image processing," eLife, vol. 7, No. e35383, 2018, 24 pages.
Hollingdale, et al., "Activity of human volunteer sera to candidate Plasmodium falciparum circumsporozoite protein vaccines in the inhibition of sporozoite invasion assay of human hepatoma cells and hepatocytes," Trans. R. Soc. Trop. Med. Hyg., vol. 84, No. 3, 1990, pp. 325-329.
Imkeller, et al., "Antihomotypic affinity maturation improves human B cell responses against a repetitive epitope," Science, vol. 360, 2018, pp. 1358-1362.
Ireton, et al., "Microseed matrix screening to improve crystals of yeast cytosine deaminase" Acta Crystallographica Section D, vol. D60, 2004, pp. 601-605.

(Continued)

*Primary Examiner* — Jennifer E Graser
(74) *Attorney, Agent, or Firm* — C. Rachal Winger; Chrystal Quisenberry; Lee & Hayes PC

(57) ABSTRACT

Mutated and/or truncated malarial circumsporozoite proteins (CSP) and associated nucleic acids that are more stable and highly expressed in mammalian cells are described. The mutated and/or truncated CSP and associated nucleic acids can be expressed to produce malaria vaccine antigens.

20 Claims, 15 Drawing Sheets

Figure 1:
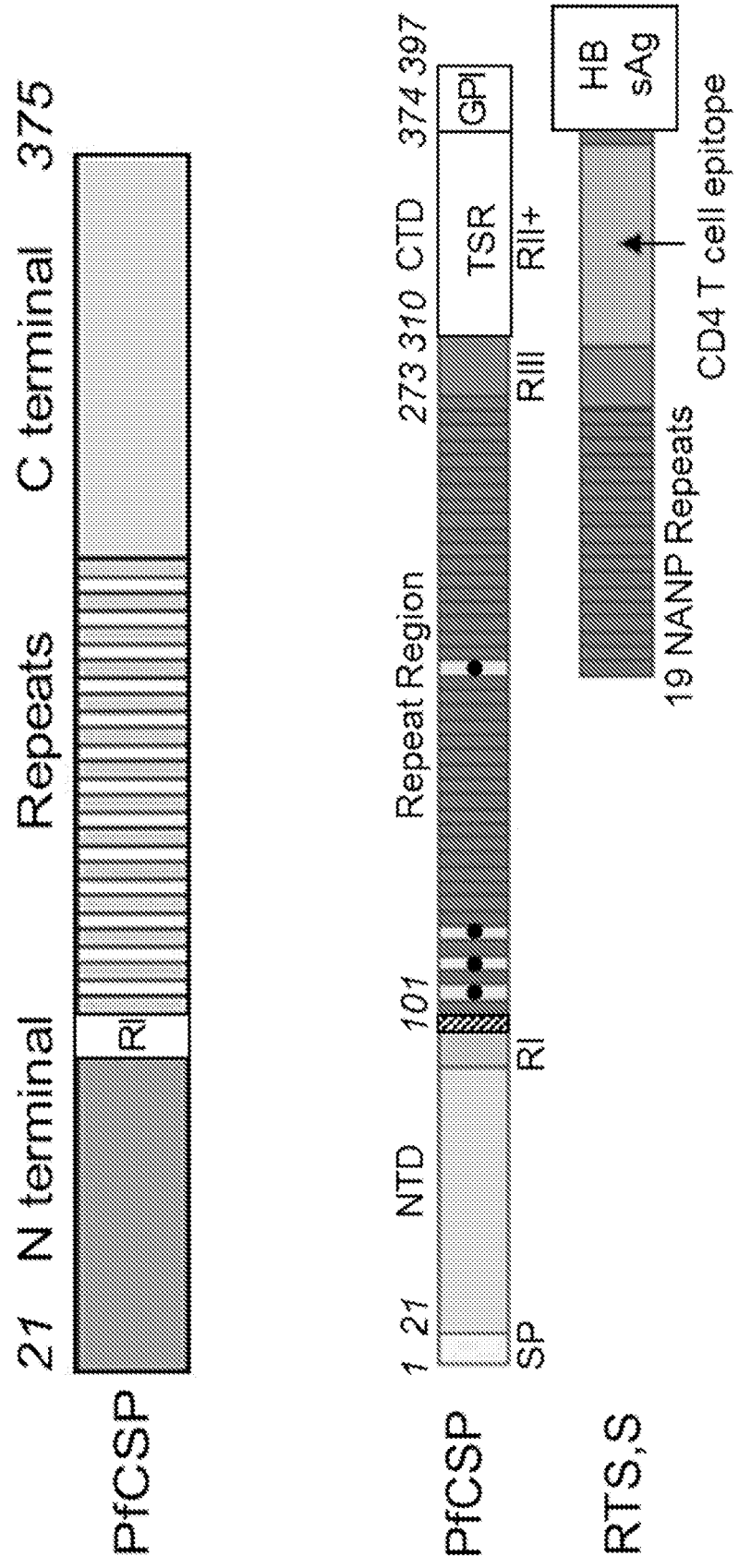

Specification includes a Sequence Listing.

(56) References Cited

PUBLICATIONS

Jackson, et al., "X-ray structure determination using low-resolution electron microscopy maps for molecular replacement," Nat Protoc. vol. 10, No. 9, 2015, pp. 1275-1284.

Kester, et al., "Randomized, Double-Blind, Phase 2a Trial of Falciparum Malaria Vaccines RTS, S/AS01B and RTS,S/AS02A in Malaria-Naive Adults: Safety, Efficac, and Immunologic Associates of Protection," J Infect Dis., vol. 3, 2009, pp. 337-346.

Kisalu, et al., "A human monoclonal antibody prevents malaria infection and defines a new site of vulnerability on Plasmodium falciparum circumsporozoite protein," Nat Med., vol. 24, No. 4, 2018, pp. 408-416.

Krishnamurty, et al., "Somatically Hypermutated Plasmodium-Specific IgM+ Memory B Cells Are Rapid, Plastic, Early Responders upon Malaria Rechallenge," Immunity, vol. 45, 2016, pp. 402-414.

Kwong, et al., "Probability Analysis of Variational Crystallization and Its Application to gp120, The Exterior Envelope Glycoprotein of Type 1 Human Immunodeficiency Virus (HIV-1)," The Journal of Biological Chemistry, vol. 274, No. 7, 1999, pp. 4115-4123.

Miller, et al., "Quantitative Bioluminescent Imaging of Pre-Erythrocytic Malaria Parasite Infection Using Luciferase-Expressing Plasmodium yoelli," PLOS One, vol. 8, No. 4, 2013, 9 pages.

Oyen, et al., "Structural basis for antibody recognition of the NANP repeats in Plasmodium falciparum circumsporozoite protein," PNAS, vol. 114, No. 48, 2017, pp. E10438-E10445.

Scally, et al., "Rare PfCSP C-terminal antibodies induced by live sporozoite vaccination are ineffective against malaria Infection," The Journal of Experimental Medicine, vol. 215, No. 1, 2018, pp. 63-75.

Singh, et al., "Genetic linkage of autologous T cell epitopes in a chimeric recombinant construct improves anti-parasite and anti-disease protective effect of a malaria vaccine candidate," Vaccine, vol. 28, No. 14, 2010, pp. 2580-2592.

Singh, et al., "Plasmodium Circumsporozoite Protein Promotes the Development of the Liver Stages of the Parasite," Cell, vol. 131, 2007, pp. 492-504.

Suloway, et al., "Automated molecular microscopy: the new Leginon system," J. Struct. Biol., vol. 151, No. 1, 2005, pp. 41-60.

Swearingen, et al., "Interrogating the Plasmodium Sporozoite Surface: Identification of Surface-Exposed Proteins and Demonstration of Glycosylation on CSP and TRAP by Mass Spectrometry-Based Proteomics," PLOS Pathogens, vol. 12, No. 4, 2016, 32 pages.

Triller, et al., "Natural Parasite Exposure Induces Protective Human Anti-Malarial Antibodies," Immunity, vol. 47, 2017, pp. 1197-1209.

White, et al., "The Relationship between RTS,S Vaccine-Induced Antibodies, CD4+ T Cell Responses and protection against Plasmodium falciparum Infection," PLOS One, vol. 8, No. 4, 2013, 10 pages.

Zhao, et al., "The rodent malaria liver stage survives in the rapamycin-induced autophagosome of infected Hepa1-6 cells," Scientific Reports, vol. 6, No. 38170, 2016, 9 pages.

Zivanov, et al., "New tools for automated high-resolution cryo-EM structure determination in RELION-3," eLife, vol. 7, No. 342166, 2018, 22 pages.

| Res. # | AMINO ACIDS | | | | YIELD (in pmoles) | | | |
|---|---|---|---|---|---|---|---|---|
| 1 | S | Y | E | | 10 | 6 | 6 | |
| 2 | L | N | | | 16 | 3 | | |
| 3 | G | N | | | 12 | 7 | | |
| 4 | E | N | Y | | 10 | 5 | 3 | |
| 5 | N | E | | | 12 | 5 | | |
| 6 | D | N | | | 7 | 7 | | |
| 7 | D | N | | | 10 | 6 | | |

FIG. 5A

SLKKNSRSLGENDD ────▶ SLSSNSSSLGENDD
(SEQ ID NO: 7)                (SEQ ID NO: 8)

QEYQCYGSSSNTRVLNELNYDNAGTNLYNELEMNYYGKQENWYSLSSNSSSLGENDD
(SEQ ID NO: 9)

FIG. 5B

PfCSP S-mut

FIG. 9

| CSP variants | Number of NANP repeats |
| --- | --- |
| PfC5S-SAmut | 38 |
| PfC5S-SAmut-23/4 | 23 |
| PfC5S-SAmut-19/3 | 19 |
| PfC5S-SAmut-12/3 | 12 |
| PfC5S-SAmut-5/3 | 5 |

FIG. 9 cont'd

FL C5S-SAmut:
QEYQSYGSSSNTRVLNELNYDNAGTNLYNELEMNYYGKQENWYSLSSNSASLGENDDGNN
EDNEKLRKPKHKKLKQPADGNPDPNANPNVDPNANPNVDPNANPNVDPNANPNANPNANPN
ANPNANPNANPNANPNANPNANPNANPNANPNANPNANPNANPNANPNANPNVDPNA
NPNANPNANPNANPNANPNANPNANPNANPNANPNANPNANPNANPNANPNANPNAN
PNANPNANPNKNNQGNGQGHNMPNDPNRNVDENANANSAVKNNNNEEPSDKHIKEYLNKIQ
NSLSTEWSPCSVTCGNGIQVRIKPGSANKPKDELDYANDIEKKICKMEKCSGSG<u>LNDIFEAQKIE
WHE</u>LEVLFQGPG*HHHHHH* (SEQ ID NO: 12)

C5S-SAmut-23/4:
QEYQSYGSSSNTRVLNELNYDNAGTNLYNELEMNYYGKQENWYSLSSNSASLGENDDGNN
EDNEKLRKPKHKKLKQPADGNPDPNANPNVDPNANPNVDPNANPNVDPNANPNANPNANPN
ANPNANPNANPNANPNANPNANPNANPNANPNANPNANPNANPNANPNANPNVDPNA
NPNANPNANPNKNNQGNGQGHNMPNDPNRNVDENANANSAVKNNNNEEPSDKHIKEYLNKI
QNSLSTEWSPCSVTCGNGIQVRIKPGSANKPKDELDYANDIEKKICKMEKCSGSG<u>LNDIFEAQK
IEWHE</u>LEVLFQGPG*HHHHHH* (SEQ ID NO: 13)

C5S-SAmut-19/3:
QEYQSYGSSSNTRVLNELNYDNAGTNLYNELEMNYYGKQENWYSLSSNSASLGENDDGNN
EDNEKLRKPKHKKLKQPADGNPDPNANPNVDPNANPNVDPNANPNVDPNANPNANPNANPN
ANPNANPNANPNANPNANPNANPNANPNANPNANPNANPNANPNANPNKNNQGNGQ
GHNMPNDPNRNVDENANANSAVKNNNNEEPSDKHIKEYLNKIQNSLSTEWSPCSVTCGNGIQ
VRIKPGSANKPKDELDYANDIEKKICKMEKCSGSG<u>LNDIFEAQKIEWHE</u>LEVLFQGPG*HHHHHH*
(SEQ ID NO: 14)

C5S-SAmut-5/3:
QEYQSYGSSSNTRVLNELNYDNAGTNLYNELEMNYYGKQENWYSLSSNSASLGENDDGNN
EDNEKLRKPKHKKLKQPADGNPDPNANPNVDPNANPNVDPNANPNVDPNANPNANPNKNNQ
GNGQGHNMPNDPNRNVDENANANSAVKNNNNEEPSDKHIKEYLNKIQNSLSTEWSPCSVTC
GNGIQVRIKPGSANKPKDELDYANDIEKKICKMEKCSGSG<u>LNDIFEAQKIEWHE</u>LEVLFQGPG*H
HHHH* (SEQ ID NO: 15)

DeltaN-CSP
SLGENDDGNNEDNEKLRKPKHKKLKQPADGNPDPNANPNVDPNANPNVDPNANPNVDPNAN
PNANPNANPNANPNANPNANPNANPNANPNANPNANPNANPNANPNANPNANPNANP
NANPNVDPNANPNANPNANPNANPNANPNANPNANPNANPNANPNANPNANPNANPN
ANPNANPNANPNANPNANPNKNNQGNGQGHNMPNDPNRNVDENANANSAVKNNNNEEPSD
KHIKEYLNKIQNSLSTEWSPCSVTCGNGIQVRIKPGSANKPKDELDYANDIEKKICKMEKCSGS
G<u>LNDIFEAQKIEWHE</u>LEVLFQGPG*HHHHHH* (SEQ ID NO: 77)

DeltaN-CSP-5/3
SLGENDDGNNEDNEKLRKPKHKKLKQPADGNPDPNANPNVDPNANPNVDPNANPNVDPNAN
PNANPNANPNANPNANPNANPNANPNANPNANPNANPNANPNANPNANPNANPNANP
NANPNVDPNANPNANPNANPNKNNQGNGQGHNMPNDPNRNVDENANANSAVKNNNNEEPS
DKHIKEYLNKIQNSLSTEWSPCSVTCGNGIQVRIKPGSANKPKDELDYANDIEKKICKMEKCSGS
G<u>LNDIFEAQKIEWHE</u>LEVLFQGPG*HHHHHH* (SEQ ID NO: 78)

FIG. 9 cont'd

DeltaN-CSP-19/3
SLGENDDGNNEDNEKLRKPKHKKLKQPADGNPDPNANPNVDPNANPNVDPNANPNVDPNAN
PNANPNANPNANPNANPNANPNANPNANPNANPNANPNANPNANPNANPNANPNANPNANP
NKNNQGNGQGHNMPNDPNRNVDENANANSAVKNNNNEEPSDKHIKEYLNKIQNSLSTEWSP
CSVTCGNGIQVRIKPGSANKPKDELDYANDIEKKICKMEKCSGSG<u>LNDIFEAQKIEWHE</u>**LEVLF
QGPG**HHHHHH (SEQ ID NO: 79)

NPDPNANPNVDPNAN (junctional epitope) (SEQ ID NO: 16)

NVDPNANPNVDPN (minor epitope) (SEQ ID NO: 17)

NPDPNANPNVDPNANPNVDPNANPNVDPN (junctional epitope linked to minor epitope) (SEQ ID NO: 18)

FIG. 11

```
Plasmodium species   Host
P. falciparum   (human)     QEYQCYGSSSMTxxxxxxxxxNLYNELEMNYYGKQENWYSLKKMSxxxxx
P. vivax        (human)     ------VDLSKAINLNGVMENNVDASSLGAA-HVG------QSASRGxxxx
P. malariae     (human)     PGYHHNSNSTKSRMLSELCYNNVDT-KLFNELEVRYSTNQDHFYNYNKTIxxxxx
P. knowlesi     (primate)   THEEHNVDLSRAxxxxxVSENNVDTSSLGAA-QVR------QSASRGxxxx
P. reichenowi   (primate)   QEYQCYGSSSMTGVINELNLNGVSENNVDASSLGAA-QVR------QSASRGxxxx
P. cynomolgi    (NHP)       TQWGHNVDFSKAINLNGVSENNVDASSLGAA-QVR------QSASRGxxxx
P. berghei      (rodent)    PGYGQNKSIQAQxxxxxxCYNEGNDMKLYHVL----MSKNGKIYNRNTVNxxxxx
P. yoelii       (rodent)    PGYGQNKSVQAQxxxxxxCYNEENDMKLYHVL----NSKNGKIYNRNIVNxxxxx
P. gallinaceum  (birds)     QEYQHWGNVYKNFxxxxxVCYNMMNI-QLYNELEMENYMSMTYFYNMKKTIxxxxx Plasmodium species   Host
P. falciparum   (human)     NDDGNN------------EDMEKLRKPKHKxxxxxADGN
P. vivax        (human)     NPDDEEGDAKKK------KDGKKAEPKNPREMxxxxGDRA
P. malariae     (human)     NMMEKDGNVTNER-----------KKKPTKAVEMxxxxPGDD
P. knowlesi     (primate)   KPKEGDDKEKKK-----E-KEKEEEPKNLMEMxxxxMAEG
P. reichenowi   (primate)   NDDADMGDEGIDEMRRH-----RMKEGKEKLKKPKHMxxxxGNDN
P. cynomolgi    (NHP)       NPKNEEGADKPK-------KKDEKQVEPKKPREMxxxxAGMN
P. berghei      (rodent)    APEGKKKNEKKNEKIERMN-----------xxxxPPPP
P. yoelii       (rodent)    ALNGKPEEKKDDPPKDGMKDDLPKEG-KKDDLPKExxxxKDP
P. gallinaceum  (birds)     NDMEAMVNRANMVANDMRANGMRGN---VNRA--MDRNI----
```

(SEQ ID NOs. 19-27)

CIRCUMSPOROZOITE PROTEINS WITH INCREASED EXPRESSION IN MAMMALIAN CELLS

CROSS-REFERENCE TO RELATED APPLICATIONS

This application is a U.S. National Phase based on International Patent Application No. PCT/US2020/023375, filed Mar. 18, 2020, which claims priority to U.S. Provisional Patent Application No. 62/820,087 filed Mar. 18, 2019, the entire contents of both of which are incorporated by reference herein in their entirety.

REFERENCE TO SEQUENCE LISTING

The Sequence Listing associated with this application is provided in text format in lieu of a paper copy and is hereby incorporated by reference into the specification. The name of the text file containing the Sequence Listing is F053-0104US_ST25.txt. The text file is 78 KB, was created on Sep. 14, 2021 and is being submitted electronically via EFS-Web.

FIELD OF THE DISCLOSURE

The current disclosure provides truncated and/or mutated malarial circumsporozoite proteins (CSP) and associated nucleic acids that are more stable and highly expressed in mammalian cells. The truncated and/or mutated CSP and associated nucleic acids can be used to produce malaria vaccine antigens.

BACKGROUND OF THE DISCLOSURE

Malaria is a deadly disease that affects 220 million worldwide and caused 435,000 deaths in 2017. It is initiated by *Plasmodium* parasites which are transmitted to people through the bites of infected female Anopheles mosquitoes. Malaria is a preventable and curable infectious disease, and public health efforts have dramatically lowered infection rates and reduced the disease burden in some areas by using antimalarial drugs, mosquito nets, and insecticides. However, antimalarial drug and insecticide resistance may counterbalance these efforts.

Vaccines are formulations that produce an immune system response against a particular pathogen by preemptively exposing a subject's immune system to an antigen of the pathogen. A pathogen antigen can be an intact, but non-infectious form of a pathogen (e.g., heat-killed), or can be a protein or protein fragment of the pathogen. When the immune system recognizes a pathogen antigen following preemptive exposure, it can lead to long-term immune memory so that if the antigen is encountered again, the immune system can quickly and effectively mount an effective response.

When a vaccine is delivered to a subject, antigen presenting cells (APC) of the immune system take up the antigen component and present it or a fragment thereof to B cells and T cells. B cells that express receptors specific for the presented antigen will produce and secrete antibodies that circulate through the body to elicit a quick, robust immune response if the antigen is encountered again later in life. Standard vaccines are designed to function via such antibody responses created by B cells. The effectiveness of B cell immunity is enhanced when the vaccine antigen is similarly recognized by CD4+ helper T cells.

A vaccine is urgently needed to reduce malaria infection rates in many geographic areas. An ideal vaccine would eliminate transmission and eradicate malaria. The *Plasmodium* parasite life cycle, however, is highly complex, passing through multiple life stages in two living beings, the mosquito vector and the vertebrate host. Each stage of the life cycle presents unique challenges to vaccine developers. The three stages of the *Plasmodium* life cycle include (1) the pre-erythrocytic stage, also known as the liver stage, or the stage before the parasite infects human red blood cells, (2) the erythrocytic stage, or the blood stage when the parasite is infecting red blood cells, and (3) the sexual stage, when the parasite has been taken up by a mosquito and is sexually reproducing in the mosquito gut. The reproduction of the parasite can be both asexual (the first two stages) and sexual (the last stage). Each stage of development presents a different form of the parasite with unique shapes and structures: sporozoite, merozoite, gametocytes and oocytes, which present different surface antigens to the immune system making the development of effective vaccines against the parasite a very complex and challenging task. Another difficulty is that malaria does not confer sterilizing immunity, although people who are re-infected have a less severe case of the disease, showing some naturally acquired immunity which is lost upon lack of exposure.

Immunization with irradiated sporozoites can protect mice from challenges with infectious sporozoites, which was successfully translated to humans. This finding gave hope to the scientific community that an effective malaria vaccine can be developed.

The *Plasmodium falciparum* Circumsporozoite protein (PfCSP) forms a dense coat at the surface of the sporozoite and is responsible for various functions (attachment to cells, development). PfCSP has been a target for vaccine design and a truncated version of CSP linked to hepatitis B surface antigen (HBsAg) is the premise of the anti-malarial RTS,S vaccine currently under development. RTS,S, targets the pre-erythrocytic stage of the life cycle and has shown 36% efficacy over four years of follow-up in children receiving four doses and has been approved for licensing by European regulators.

A protective antibody that binds a novel site of vulnerability on PfCSP, the junctional epitope, that is currently not included in the RTS,S vaccine was recently isolated as described in Kisalu et al., Nature Medicine, 2018 (doi: 10.1038/nm4513). It was hypothesized that using an immunogen that contains numerous or all of the protective epitopes of PfCSP could increase the breadth and possibly the durability of the immune response against malaria following vaccination and thus could improve upon the current RTS,S and related vaccines.

While these vaccines have provided significant advances in the on-going pursuit of an effective anti-malarial vaccine, significant challenges remain. One such challenge includes the difficulty associated with producing some CSP proteins. Currently available mammalian expression systems provide extremely low yields of protein, such as 50 μg/L. Expression in mammalian systems can be advantageous when using DNA or mRNA delivery.

SUMMARY OF THE DISCLOSURE

The current disclosure describes truncated and/or mutated forms of CSP proteins that increase stability and yield when expressed in mammalian systems by, for example, 100-

300%. The mutations that provide significant increases in expression are located within the N-terminus domain of the CSP protein.

Particular embodiments include mutating KKNSR (SEQ ID NO: 1) to SSNSS (SEQ ID NO: 2) directly upstream of an identified SLGENDD (SEQ ID NO: 3) cleavage site. This mutation can increase expression 100-fold in mammalian cells over the wild type CSP protein.

Particular embodiments include removing a free cysteine in the N-terminus preventing dimerization and mutating KKNSR (SEQ ID NO: 1) to SSNSA (SEQ ID NO: 4) directly upstream of the identified SLGENDD (SEQ ID NO: 3) cleavage site. This alternation avoids a glycosylation site introduced by the SSNSS (SEQ ID NO: 2) motif. This mutant of WT CSP can have a 300-fold increase in expression in mammalian cells over WT. In particular embodiments, dimerization of proteins can increase avidity, so the free cysteine need not be removed.

Particular embodiments include a mutated N-terminus as described herein expressed as a fusion protein with one or more CSP repeat domains; with the junctional CSP epitope; the minor CSP epitope; the junctional CSP epitope linked to the minor epitope; the RST,S epitope; or any other relevant fragment of the CSP protein. In particular embodiments, the mutated N-terminus can remain fused to other CSP fragments and epitopes following expression. In other embodiments, the fusion proteins described herein can allow cleavage of the mutated N-terminus from other CSP fragments and epitopes. Particular embodiments include FL C5S-SAmut: (SEQ ID NO: 12); C5S-SAmut-23/4: (SEQ ID NO: 13); C5S-SAmut-19/3: (SEQ ID NO: 14); C5S-SAmut-5/3: (SEQ ID NO: 15); DeltaN-CSP (SEQ ID NO: 77); DeltaN-CSP-5/3 (SEQ ID NO: 78); and DeltaN-CSP-19/3 (SEQ ID NO: 79).

When used as vaccines, the mutated proteins (or associated nucleic acids) disclosed herein can be multimerized and/or associated with various forms of particles (e.g., lipid nanoparticles) for delivery. The disclosed vaccines can similarly be administered with one or more vaccine adjuvants.

BRIEF DESCRIPTION OF THE SEVERAL VIEWS OF THE DRAWINGS

FIG. 1. Schematic and organization of the *Plasmodium falciparum* Circumsporozoite protein (PfCSP) and the RTS, S, AS01 vaccine. Top panel: designations of N-terminal domain; repeat region; and C-terminal domain of PfCSP. Middle panel: PfCSP in more detail: SP: signal peptide (residues 1-20); NTD: N-terminal domain (residues 21-92); RI: region I (residues 93-96); Junction NPDP (residues 101-115 (SEQ ID NO: 32)); Repeat Region with NANP (SEQ ID NO: 30) repeats in dark and light grey and Minor repeats NVDP (SEQ ID NO: 31) designated with (•) (for example, residues 109-112); Start of C-terminal domain: RIII: Region III (residues 273-310); TSR: type I thrombospondin repeat region (RII+: Region II+, residues 311-373); GPI: Glycosylphosphatidylinositol domain (residues 374-397). Bottom panel: RTS,S, AS01 vaccine: 19 NANP (SEQ ID NO: 30) repeats in dark and light grey; RIII; TSR; and truncated GPI with HBsAg: hepatitis B surface antigen.

FIGS. 2A, 2B. Wldtype (WT) PfCSP mammalian expression: Wild Type PfCSP can be produced in 293E HEK cells, however, expression is poor (e.g., 50 μg/L). (2A) PfCSP size exclusion chromatography S200 (y axis in mAU); (2B) SDS Page Gel 4-12% Bis-Tris.

FIGS. 3A-3C. Mutant NR2C Mammalian Expression: The NR2C mutant version of PfCSP with only 2 copies of the NANP (SEQ ID NO: 30) repeat domain has improved expression over WT (1 mg/L). However, a mix of species was observed due to proteolytic cleavage. (3A) schematic of mutant NR2C protein; (3B) NRC2 size exclusion chromatography S200; (3C) SDS Page Gel 4-12% Bis-Tris (NR: non-reduced).

FIG. 4. Assessment of the proteolytic cleavage site of NR2C led to identification of a 100% sequence match for the SLGENDD (SEQ ID NO: 3) amino acid site.

FIGS. 5A-5C. Mutating KKNSR (SEQ ID NO: 1) to SSNSS (SEQ ID NO: 2) directly upstream of the identified SLGENDD (SEQ ID NO: 3) cleavage site allowed fora 100-fold increase in expression of monomer. Additionally, a large quantity of dimer was produced allowing for increased avidity. (5A) mutation positions and identity underlined for mutant referred to as SAmut (SEQ ID NO: 9); (5B) PfCSP S mutant size exclusion chromatography S200; (5C) SDS Page Gel 4-12% Bis-Tris (R: reduced).

FIGS. 6A-6C. An additional mutant version of PfCSP removes the free cysteine in the N-terminus preventing dimerization ($1^{st}$ underlined amino acid). Additionally, the KKNSR (SEQ ID NO: 1) motif was changed to SSNSA (SEQ ID NO: 4) as the SSNSS (SEQ ID NO: 2) motif introduces a glycosylation site ($2^{nd}$-$4^{th}$ underlined amino acids). This mutant of CSP, referred to herein as the C5S-SAmut (SEQ ID NO: 11), has a 300-fold increase in expression vs WT (SEQ ID NO: 10) of the monomeric species. (6A) mutation positions and identity underlined for mutant; (6B) PfCSP SA-mutant C5S mutant size exclusion chromatography S200; (6C) SDS Page Gel 4-12% Bis-Tris (L: Ladder; 1: 70 mL non-reduced; 2: 70 reduced).

FIG. 7. Side-by-side presentation of the expression profiles shown in FIG. 5B for SAmut and FIG. 6B for C5S-SAmut.

FIG. 8. Antigenicity of PfCSP and C5S-SAmut by ELISA with PfCSP-directed mAbs. CIS43 recognizes the junctional epitope; mAb10 binds the NANP (SEQ ID NO: 30) repeat; mAb15 binds an epitope in the CTD; NHP20 binds an epitope in the NTD; 5D5 binds an epitope near RI; 606-4 binds RI; VRC01 is a cognate anti-HIV-1 antibody used as negative control.

FIG. 9. CSP truncations based on CSP of the 3D7 strain. FL C5S-SAmut: 38 major repeats (light and dark grey), 4 minor repeats (designated with (•)), junctional epitope (*) (SEQ ID NO: 12); C5S-SAmut-23/4: 23 major repeats, 4 minor repeats (SEQ ID NO: 13); C5S-SAmut-19/3: 19 major repeats, 3 minor repeats (SEQ ID NO: 14); C5S-SAmut-5/3: 5 major repeats, 3 minor repeats (SEQ ID NO: 15); and N-terminus truncations DeltaN-CSP (SEQ ID NO: 77); DeltaN-CSP-23/4; DeltaN-CSP-19/3 (SEQ ID NO: 79); and DeltaN-CSP-5/3 (SEQ ID NO: 78). In provided sequences, Avi tags are underlined, HRV 3C sites are bolded, and ending 6×His tags are italicized. Mutation positions are designated with increased font size in combination with underlining. Signal peptides can be introduced to each of these sequences. The junctional epitope (SEQ ID NO: 16), minor epitope (SEQ ID NO: 17), and an example of the junctional epitope linked to the minor epitope (SEQ ID NO: 18) are also provided.

FIGS. 10A, 10B. Challenge study. Candidate vaccine immunogens were evaluated using an in vivo malaria infection model as a tool to screen for potent malaria-neutralizing antibodies. These models take advantage of a transgenic rodent malaria parasite (*P. berghei*, Pb) in which the endogenous PbCSP is replaced with PfCSP to evaluate pre-erythrocytic stage vaccine candidates. In addition, these parasites also constitutively express luciferase. In vivo bioluminescent imaging allows for an efficient, sensitive and non-invasive alternative for quantitative analysis of liver stage parasite infection. (10A) experimental protocol; (10B) study results.

FIG. 11. Sequences of NTD from human and animal *Plasmodium* species and location or Pexel I, Pexel II and RI. Alignment generated with Clustal Omega Pexel site defined as RxLxE/Q/D Uniprot IDs for protein sequences: *P. falciparum*, Q27425 (SEQ ID NO: 19); *P. vivax*, Q8MPK1 (SEQ ID NO: 20); *P. knowlesi*, F2VII7 (SEQ ID NO: 21); *P. malariae*, 062597 (SEQ ID NO: 22); *P. cynomolgi*, I2FGF0 (SEQ ID NO: 23); *P. reichenowi*, U3M 191 (SEQ ID NO: 24); *P. berghei*, A0A0Y9UA70 (SEQ ID NO: 25); *P. yoelii*, Q4U4G6 (SEQ ID NO: 26); *P. gallinaceum*, Q94675 (SEQ ID NO: 27). As one example, corresponding mutations of *P. falciparum* in *P. vivax* include: QSASRGRG (SEQ ID NO: 28) to QSASSGSG (SEQ ID NO: 29).

DETAILED DESCRIPTION

Malaria is a mosquito-borne parasitic disease that causes high fevers, severe anemia, and often death of infants and small children, primarily in sub-Saharan Africa. In 2015, there were an estimated 212 million cases and 429,000 deaths due to malaria infection. Based on the substantial morbidity, mortality and economic impact of malaria, immune interventions such as a highly effective vaccines or protective antibodies are urgently needed to prevent and ultimately eliminate malaria worldwide.

*Plasmodium falciparum* Circumsporozoite protein (PfCSP) is a membrane anchored protein of the *Plasmodium falciparum* sporozoite, one of the species that causes malaria in humans. PfCSP can be made as a recombinant soluble protein by removing the anchor region (38 KDa soluble protein) and expressing the protein in *E. coli*, Yeast or mammalian cells. It is divided in three regions (FIG. 1, top and middle panels): the N-terminus (NTD), which includes the ligand-binding domain and a cleavage site; a centrally-located repeat region which contains 38 NANP (SEQ ID NO: 30) repeats (major) and four NVDP (SEQ ID NO: 31) repeats (minor) (for *P. falciparum*, Uniprot: Q7K740_PLAF7); and the C-terminus, which contains a type I thrombospondin repeat region (TSR). PfCSP plays a role in the development of the sporozoite and is responsible for hepatocyte binding.

In more detail, the NTD interacts with Heparan Sulfate Proteoglycans (HSPGs) and is believed to play a role in masking the C-terminus domain in transit to liver. Zhao et al., Sci Rep. 2016; 6:38170. CSP mutants lacking NTD promiscuously stick to tissue in mosquito and skin. Coppi et al., J Exp Med. 2011; 208(2):341-56. A lysine cluster upstream of RI is critical for HSPGs binding. PfCSP is cleaved at RI. Coppi et al, J Exp Med. 2005; 201(1):27-33. RI is conserved among all mammalian infecting strains (FIG. 11) and NTD is less diverse across continents. Singh et al., Cell. 2007; 131(3):492-504. NTD also often contains two *Plasmodium* export element (PEXEL) sites, responsible for export of proteins out of parasitophorous vacuoles. These PEXEL sites are defined by a conserved sequence of RxLxE/Q/D (FIG. 11; Singh et al., Cell. 2007; 131(3):492-504). The lower diversity of NTD, which is functionally important and has a role in immunity, makes the inclusion of this region in an improved version of the vaccine an attractive possibility. Additionally, antibody responses to the N-terminus of CSP have been shown to be associated with protection. Bongfen et al., Vaccine. 2009; 27(2):328-35.

The central repeat region of PfCSP contains 34-39 NANP (SEQ ID NO: 30) major repeats and four NVDP (SEQ ID NO: 31) minor repeats as well as the unique junction NPDP (SEQ 10 NO: 32) sequence. Gandhi et al., PLoS One. 2014; 9(7):e101783 (doi: 10.1371/journal.pone.0101783). Antibodies directed against the repeat region may be a correlate of protection (Foquet et al., J Clin Invest. 2014; 124(1):140-4; White et al., PLoS One. 2013; 8(4):e61395 (doi: 10.1371/journal.pone.0061395; Kester et al., J Infect Dis. 2009; 200(3):337-46), as was confirmed in a CHMI challenge where antibodies to the central repeat region were shown to effectively block invasion. Hollingdale et al., Trans R Soc Trop Med Hyg. 1990; 84(3):325-9; Lancet. 2015; 386 (9988):31-45. Structural information on major (NANP (SEQ ID NO: 30) or NPNA) repeat-directed antibodies have become recently available in complex with major repeat peptides using X-ray crystallography. Imkeller et al., Science. 2018; 360(6395):1358-62; Oyen et al., Proc Natl Acad Sci USA. 2017; 114(48):E10438-E45; Triller et al., Immunity. 2017; 47(6):1197-209 e10.

The C-terminal domain (CTD) includes the TSR region which has cell adhesion properties and has been reported to be O-fucosylated. Swearingen et al, PLoS Pathog. 2016; 12(4):e1005606; Adams & Tucker, Dev Dyn. 2000; 218(2): 280-99. It is immunodominant and contains a T cell epitope. Singh et al., Vaccine. 2010; 28(14):2580-92. A crystal structure of CTD has been obtained (Doud et al., Proc Natl Acad Sci USA. 2012; 109(20):7817-22) unliganded and in complex with non-protective antibody (Scally et al., J Exp Med. 2018; 215(1):63-75), induced rarely by this epitope.

RTS,S, is a pre-erythrocytic stage vaccine currently under development. It has shown 36% efficacy in a phase III clinical trial. It is based on the hepatitis B surface antigen (HBsAg) and portion of the PfCSP antigen (FIG. 1, bottom panel) and induces high antibody titers against the PfCSP and a moderate CD4+ T cell response. Additionally, antibodies targeting novel sites of vulnerability on PfCSP have recently been identified. Kisalu et al. Nat Medicine, 2018. These epitopes, including the junctional epitope, the minor epitope, and the junctional epitope linked to the minor epitope (FIG. 9) are not present in RTS,S. As such, work on developing novel immunogens is continuing.

Despite these advances, significant challenges in malarial vaccine development remain. One such challenge includes the difficulty associated with producing some anti-malarial CSP proteins in mammalian cells.

Figure 10A:
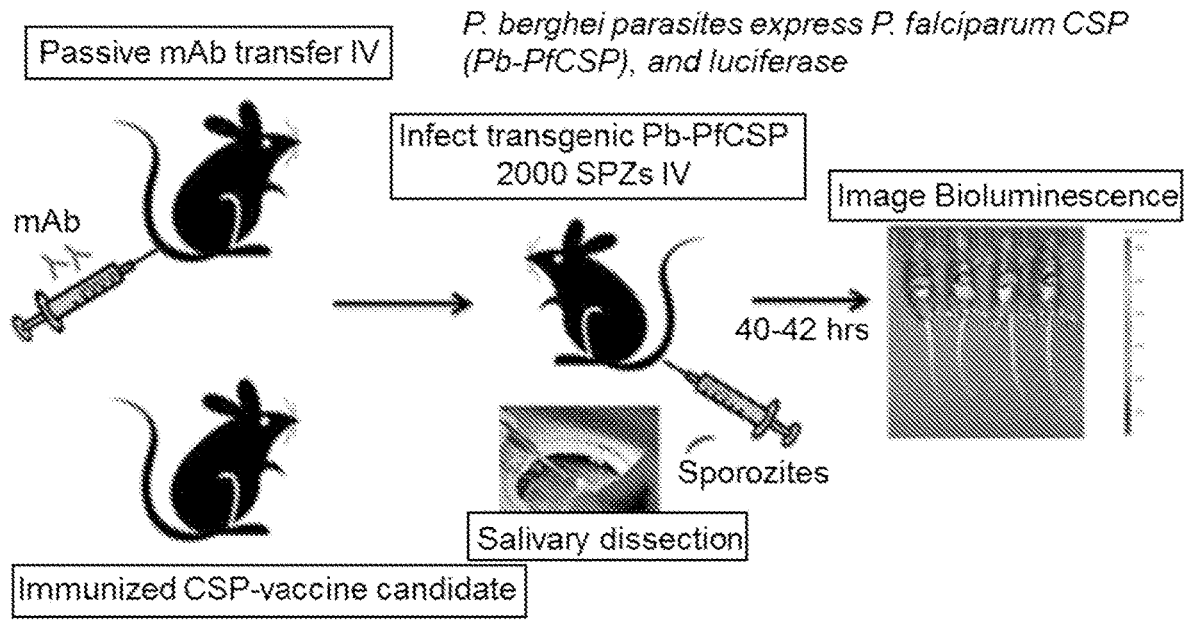
Figure 10B:
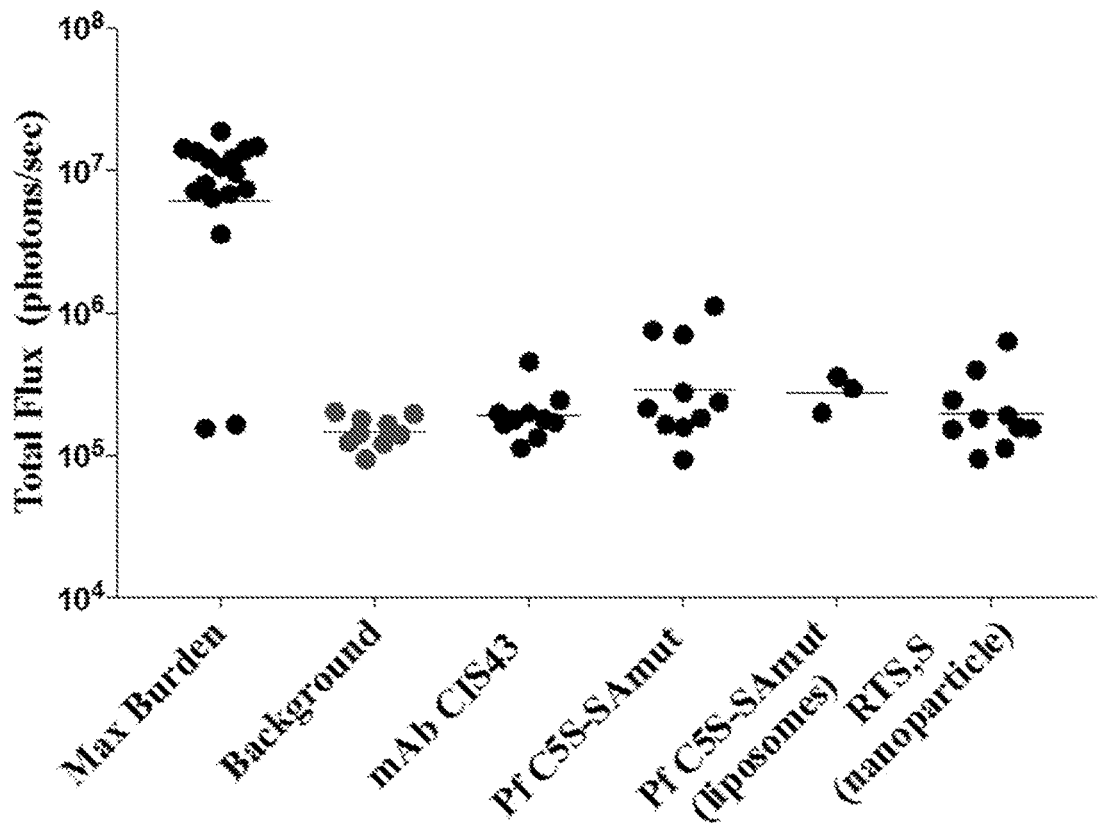

The current disclosure provides mutant stabilized versions of PfCSP with increased protein expression in mammalian cells. This development is crucial for further studies of PfCSP as a vaccine candidate. Additionally, proteins described herein show vaccine efficacy in in vivo immunization and challenge studies (FIGS. 10A, 10B).

In studies described herein, CSP constructs were cloned into the pVRC8400 plasmid vector. The protein was cloned with a 6his-tag on the C-terminus of the protein used for purification. The CSP constructs were transfected in HEK293F cells. Cells were cultured in suspension in Freestyle 293 media (Life Technologies) at 37° C. in the presence of 5% CO$_2$ and transfected with 500 µg/L plasmid DNA using 293 Free Transfection Reagent (EMD Millipore) at a density of 1 million cells per 1 mL of supernatant. After 6 days, cells were centrifuged at 4,500 rpm for 20 mins. Supernatant was filtered sterilized and incubated with His60 Ni-Superflow Resin (Novagen) overnight at 4° C., capturing CSP proteins with the 6his-tag on the C-terminus of the proteins. The Ni resin was separated from the supernatant and washed with a solution of 150 mM NaCl, 20 mM Tris pH 8.0, 20 mM Imidazole pH 7.0 and eluted with a solution of 300 mM NaCl, 50 mM Tris pH 8.0, 250 mM Imidazole pH 7.0. To further purify the proteins, the samples were run on size-exclusion chromatography (SEC) using a HiLoad 16/600 Superdex 200 pg (GE) column.

Figure 2A:
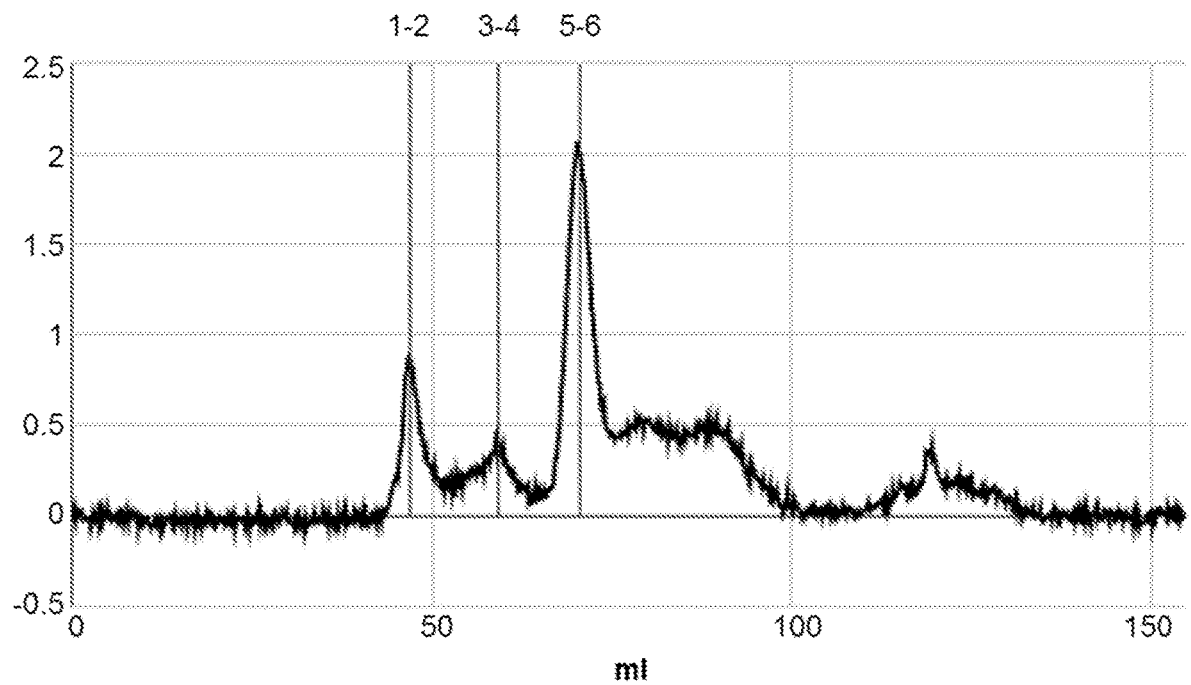
Figure 2B:
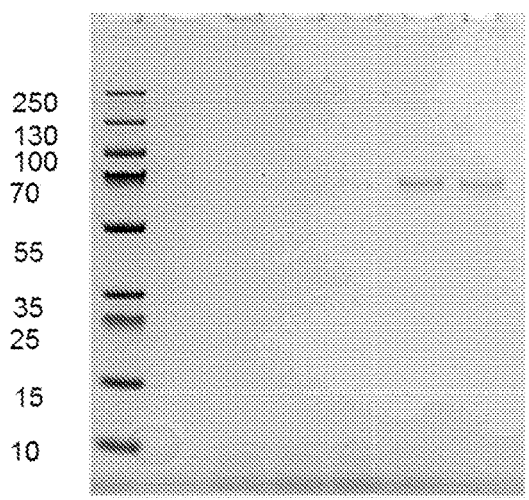
Figure 3A:
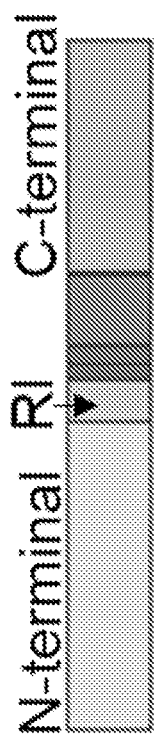
Figure 3B:
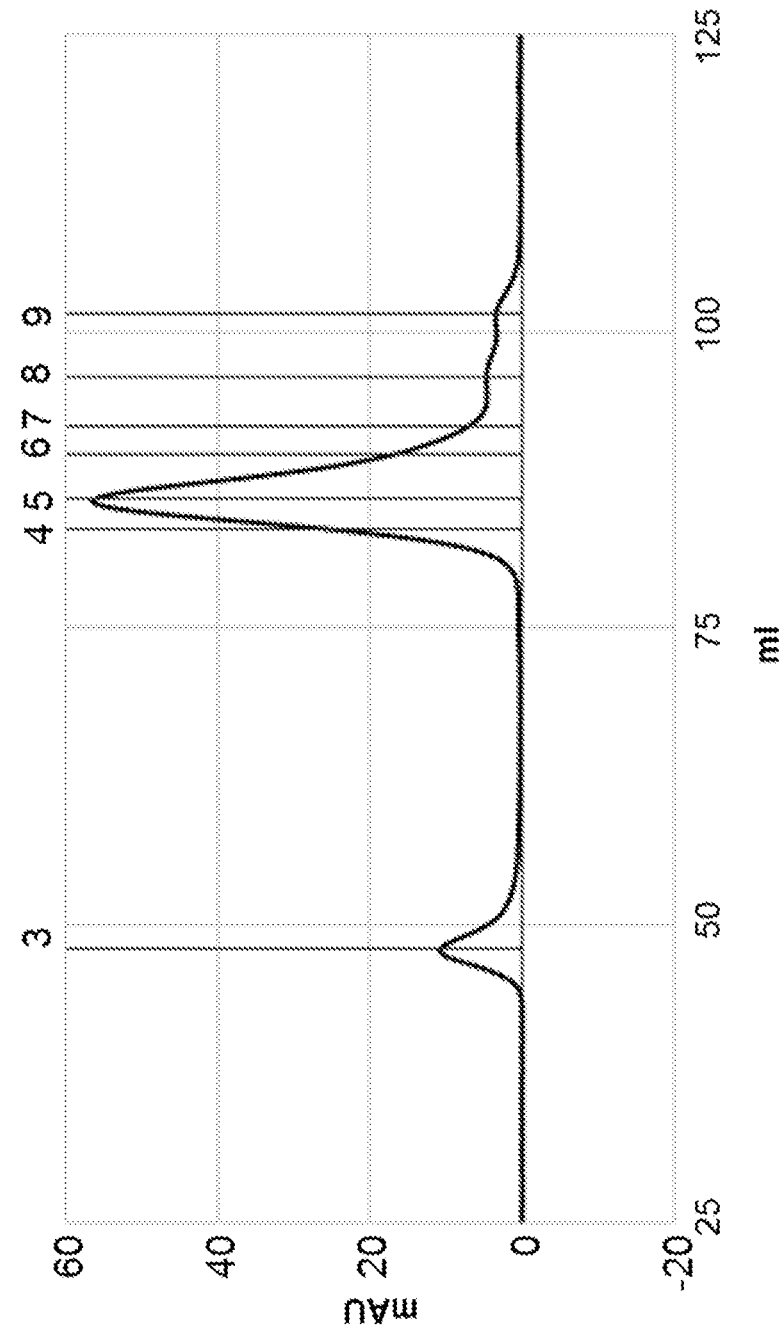
Figures 3C, 4:
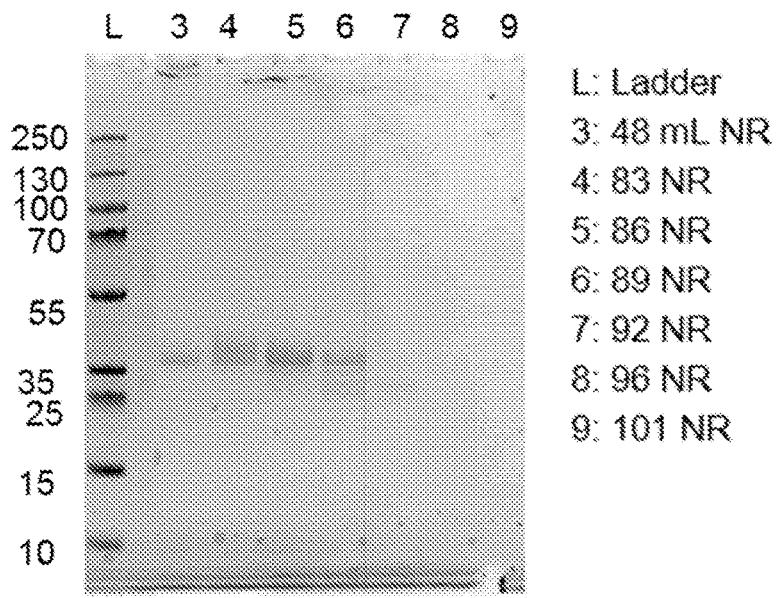

As shown in FIGS. 2A, 2B, wild type (WT) PfCSP can be expressed in mammalian 293E HEK cells, but expression is poor and in the range of 50 μg/L. FIGS. 3A-3C depict a version of the CSP protein with 2 copies of the NANP (SEQ ID NO: 30) repeat domain. This mutant has improved expression in the range of 1 mg/L. However, a mix of species is observed due to proteolytic cleavage. To determine where the protein was being proteolytically cleaved, a sample was subjected to edman degradation or N-terminal sequencing. FIG. 4 shows a 100% sequence match for the SLGENDD (SEQ ID NO: 3) amino acid site.

As shown in relation to FIGS. 5A-6C, the current disclosure describes mutated forms of CSP proteins that increase yield when expressed in mammalian systems by, for example, 100-300% over wild-type CSP. The mutations that provide significant increases in expression are located within the N-terminus of the CSP protein, allowing fusion of such stabilized N-termini with various CSP epitopes downstream of these positions.

Figure 5C:
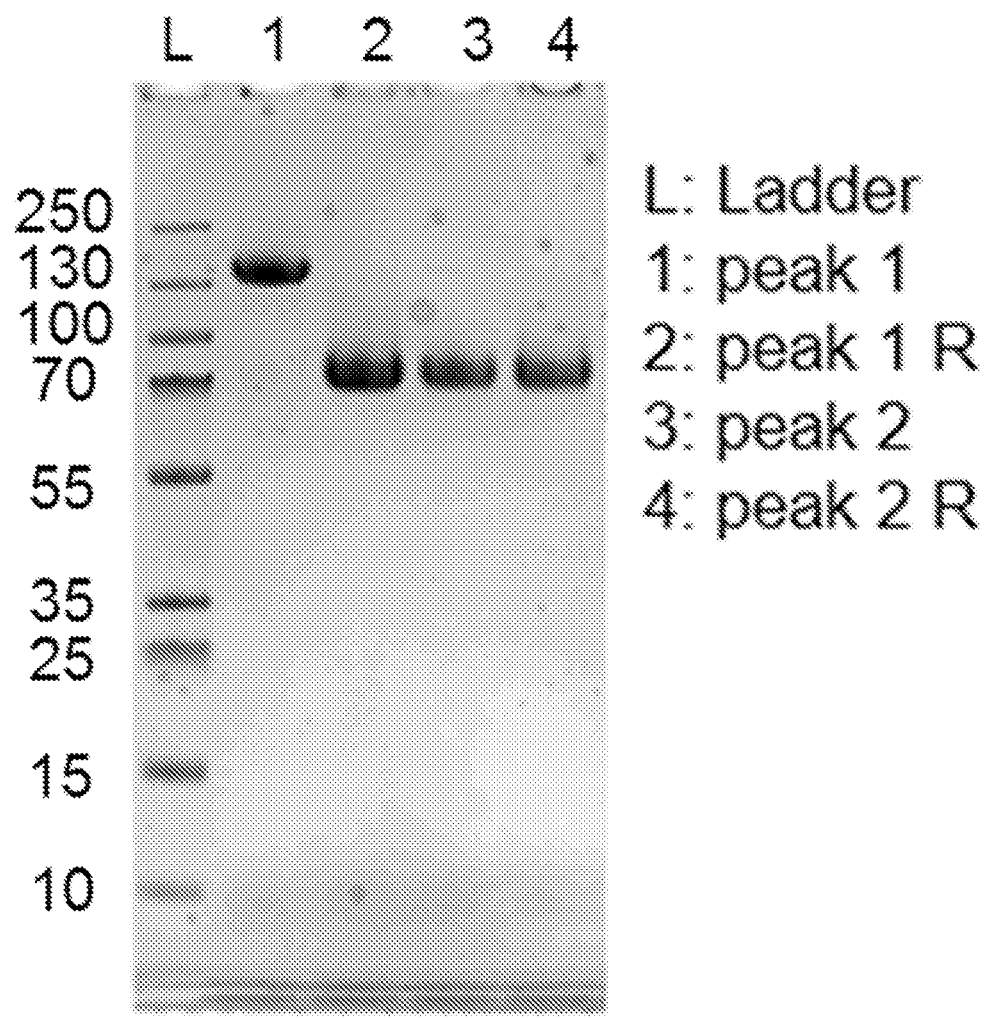
Figures 6A, 6B:
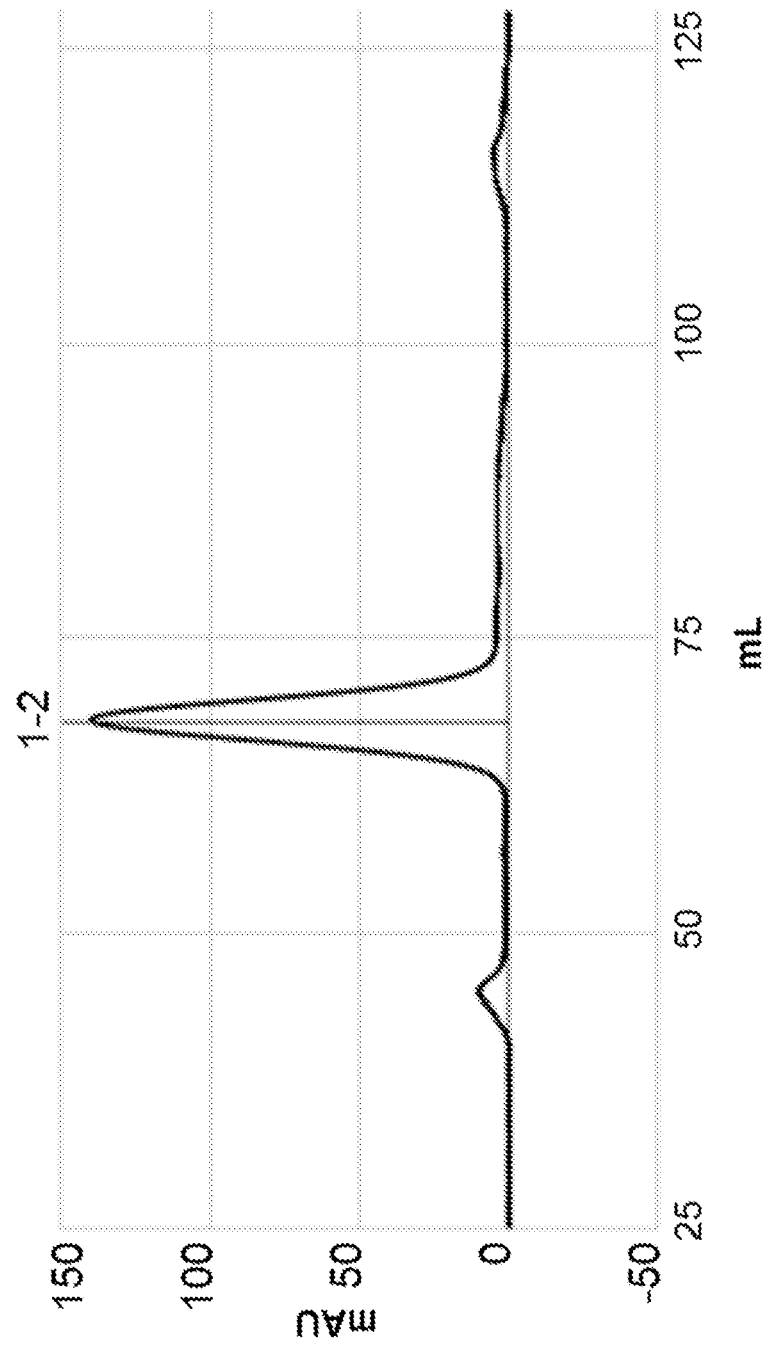
Figure 6C:
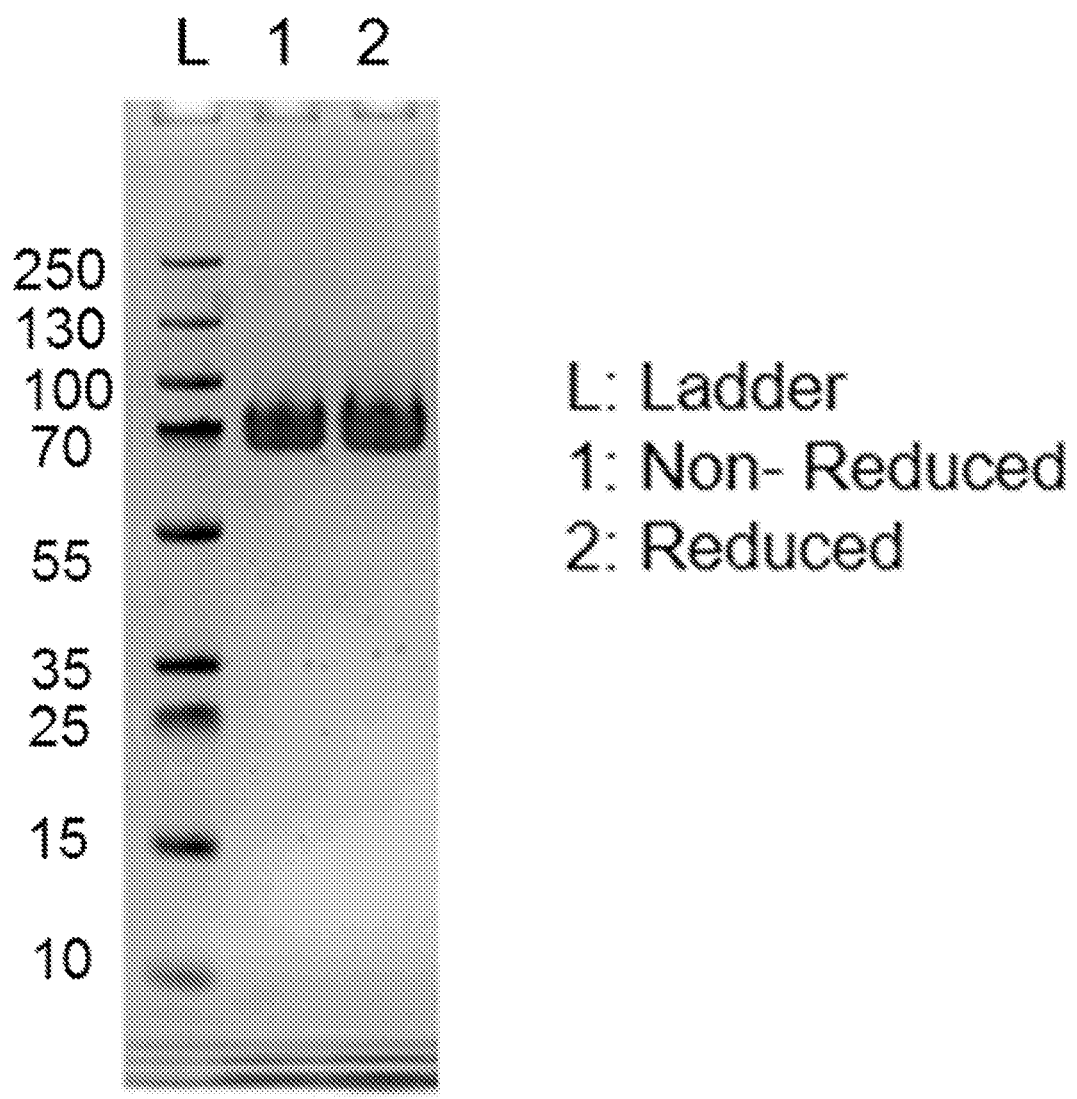
Figure 7:
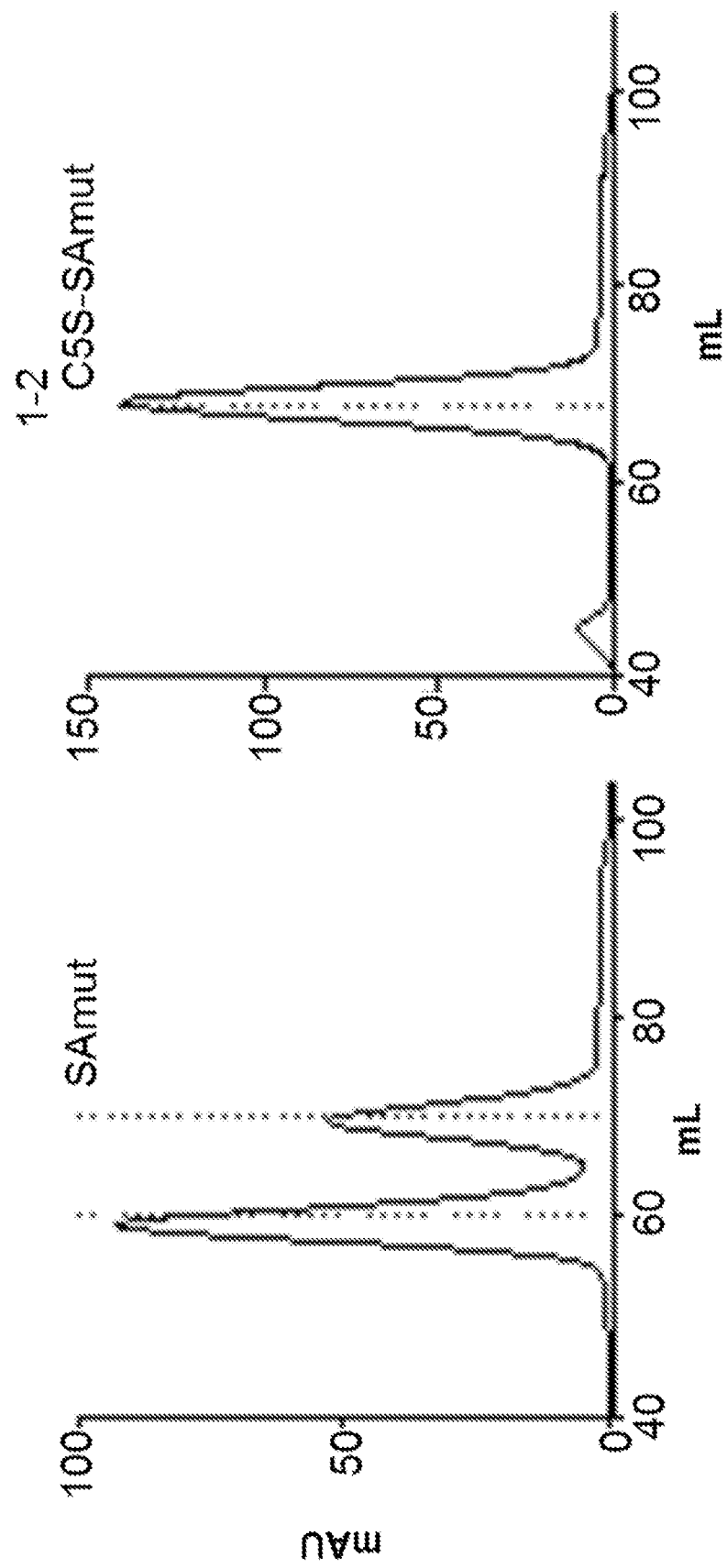
Figure 8:
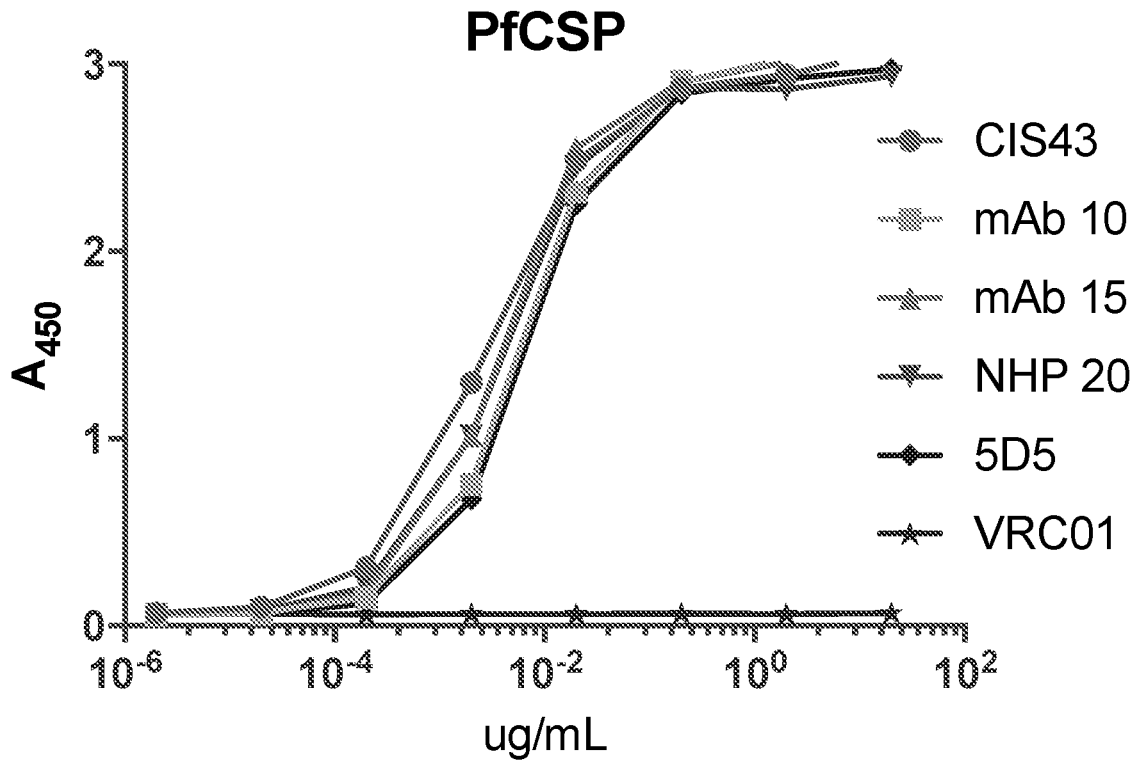
Figure 8:
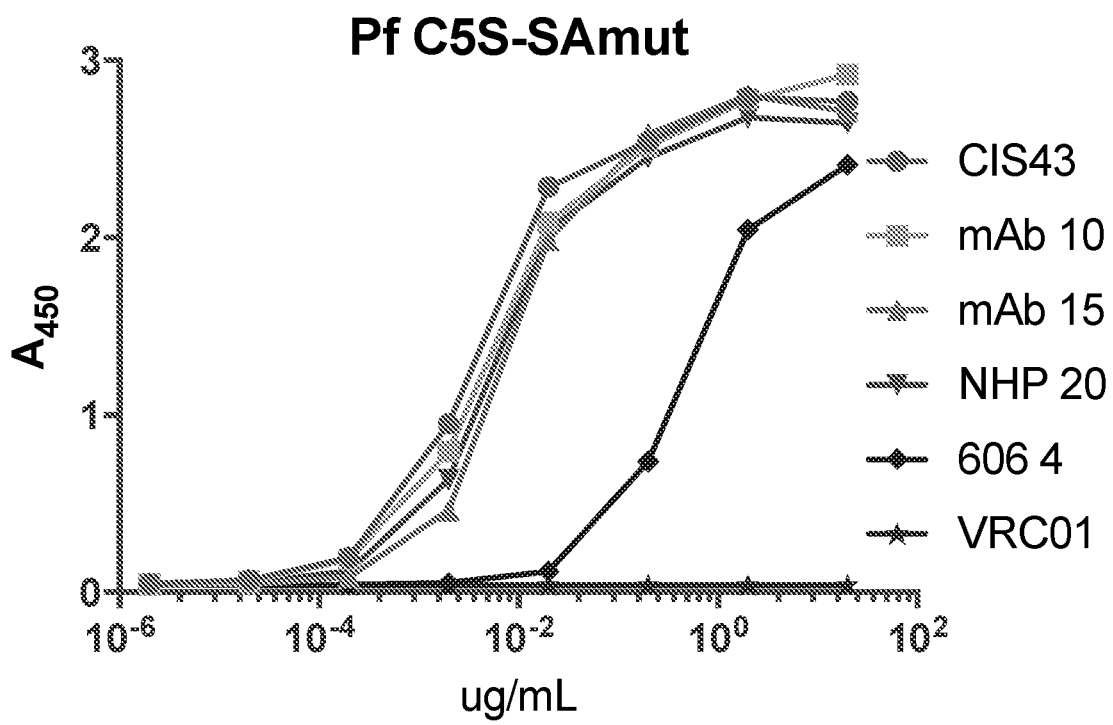

Particular embodiments include mutating KKNSR (SEQ ID NO: 1) to SSNSS (SEQ ID NO: 2) directly upstream of the identified SLGENDD (SEQ ID NO: 3) cleavage site. Directly upstream means there are no intervening amino acid residues between the last mutated residue and the beginning of the cleavage site, as depicted in FIG. 5A. This mutation increased expression 100-fold over the wild type CSP protein.

Particular embodiments include removing a free cysteine in the N-terminus preventing dimerization and changing the mutated SSXXS (SEQ ID NO: 5) motif to SSXXA (SEQ ID NO: 6) to avoid introduction of a glycosylation site. This mutant of WT CSP resulted in a 300-fold increase in expression over WT CSP. In particular embodiments, dimerization of proteins can increase avidity, so the free cysteine need not be removed.

In particular embodiments, mutant proteins disclosed herein can be used to create next generation pre-erythrocytic malaria vaccines as particular embodiments present all the epitopes of the CSP unlike the current RTS,S vaccine which only contains the repeat region and the C-terminus. However, the current disclosure is not limited to this approach. For example, particular embodiments include a mutated N-terminus as described herein expressed as a fusion protein with one or more CSP repeat domains; with the junctional CSP epitope; the minor CSP epitope; the junctional CSP epitope linked to the minor epitope; the RST,S epitope; or any other relevant fragment of the CSP protein. In particular embodiments, the mutated N-terminus can remain fused to other CSP fragments and epitopes following expression. In other embodiments, the fusion proteins described herein can allow cleavage of the mutated N-terminus from other CSP fragments and epitopes.

Particular epitopes that can be expressed with the stabilized N-termini disclosed herein are depicted in FIGS. 1 (RTS,S), 3A (NR2C), and 9 (RTS,S, NR2C, R2C, junctional epitope, minor epitope, junctional epitope linked to minor epitope). Fusion proteins according to the current disclosure are also depicted in FIG. 9 and include the C5S-SAmut, C5S-SAmut-23/4; C5S-SAmut-19/3; and C5S-SAmut-5/3, as well as DeltaN-CSP, DeltaN-CSP-5/3, and DeltaN-CSP-19/3.

When used as vaccines, the mutated proteins (or associated nucleic acids) disclosed herein can be multimerized and/or associated with various forms of particles (e.g., lipid nanoparticles) for delivery. The disclosed vaccines can similarly be administered with one or more vaccine adjuvants.

Aspects of the current disclosure are now described in more detail as follows: (i) Production of Mutant CSP; (ii) Multimerization Domains; (iii) Linkers and Cleavage Components; (iv) Particles; (v) Vaccine Adjuvants; (vi) Compositions; (vii) Kits; (viii) Methods of Use in Subjects; (ix) Exemplary Experimental Procedures; (x) Exemplary Embodiments; and (vi) Closing Paragraphs.

Production of Mutant CSP. Mutant CSP described herein can be produced using any protein manufacturing technique. In particular embodiments, the mutant CSP proteins are produced ex vivo (e.g., by recombinant cell-based protein manufacturing). The mutant CSP proteins can also be produced in vivo by a subject for an in vivo therapeutic effect.

Exemplary cell types that can be used to produce mutant CSP proteins ex vivo include: HEK (e.g., HEK293F, HEK293S, HEK293SGH, EK293FTM, HEK293SGGD, GP2-293); HeLa and related cell lines (e.g., HeLa S3, HeLa B, HeLa T4); Chinese Hamster Ovary (COS) and related cell lines (e.g., COS-1, COS-6, COS-M6A, COS-7); A549; MDCK; HepG2; C2C12; THP-1; HUDEP-2; C8161; CCRF-CEM; MOLT; mIMCD-3; NHDF; Huh1; Huh4; Huh7; HUVEC; HASMC; HEKn; HEKa; MiaPaCell; Panc1; PC-3; TF1; CTLL-2; C1R; Rat6; CV1; RPTE; A10; T24; J82; A375; ARH-77; Calu1; SW480; SW620; SKOV3; SK-UT; CaCo2; P388D1; SEM-K2; WEHI-231; HB56; TIB55; Jurkat; J45.01; LRMB; BcI-1; BC-3; IC21; DLD2; Raw264.7; NRK; NRK-52E; MRCS; MEF; BS-C-1; monkey kidney epithelial; BALB/3T3 mouse embryo fibroblast; 3T3 Swiss; 3T3-L1; 132-d5 human fetal fibroblasts; 10.1 mouse fibroblasts; 3T3; 721; 9L; A2780; A2780ADR; A2780cis; A172; A20; A253; A431; A-549; ALC; B16; B35; BCP-1; BEAS-2B; bEnd.3; BHK-21; BR 293; BxPC3; C3H-10T1/2; C6/36; Cal-27; CHO; CHO-7; CHO-IR; CHO-K1; CHO-K2; CHO-T; CHO Dhfr-/-; COR-L23; COR-L23/CPR; COR-L23/5010; COR-L23/R23; COV-434; CML T1; CMT; CT26; D17; DH82; DU145; DuCaP; EL4; EM2; EM3; EMT6/AR1; EMT6/AR10.0; FM3; H1299; H69; HB54; HB55; HCA2; Hepa1c1c7; HL-60; HMEC; HT-29; JY; K562; Ku812; KCL22; KG1; KYO1; LNCap; Ma-Mel 1-48; MC-38; MCF-7; MCF-10A; MDA-MB-231; MDA-MB-468; MDA-MB-435; MDCK II; MOR/0.2R; MONO-MAC 6; MTD-1A; MyEnd; NCI-H69/CPR; NCI-H69/LX10; NCI-H69/LX20; NCI-H69/LX4; NIH-3T3; NALM-1; NW-145; OPCN/OPCT cell lines; Peer; PNT-1A/PNT2; RenCa; RIN-5F; RMA/RMAS; Saos-2; Sf-9; SkBr3; T2; T-47D; T84; THP1; U373; U87; U937; VCaP; Vero; WM39; WT-49; X63; YAC-1; and YAR.

Desired genes encoding mutant CSP proteins described herein can be introduced into cells by any method known in the art, including transfection, electroporation, microinjection, lipofection, calcium phosphate mediated transfection, infection with a viral or bacteriophage vector including the gene sequences, cell fusion, chromosome-mediated gene transfer, microcell-mediated gene transfer, sheroplast fusion, in vivo nanoparticle-mediated delivery, etc. Numerous techniques are known in the art for the introduction of foreign genes into cells (see e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92) and may be used, provided that the necessary developmental and physiological functions of the recipient cells are not unduly disrupted. In particular embodiments, the technique can provide for the stable transfer of the gene to the cell, so that the gene is expressible by the cell and, in certain instances, preferably heritable and expressible by its cell progeny.

The term "gene" refers to a nucleic acid sequence (used interchangeably with polynucleotide or nucleotide sequence) that encodes a mutant CSP protein described herein. "Encoding" refers to the property of specific sequences of nucleotides in a gene, such as a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. This definition includes various sequence polymorphisms, mutations, and/or sequence variants wherein such alterations do not substantially affect the function of the encoded mutant CSP protein. The term "gene" may include not only coding sequences but also regulatory regions such as promoters, enhancers, and termination regions. The term further can include all introns and other DNA sequences spliced from an mRNA transcript, along with variants resulting from alternative splice sites. Gene sequences encoding the molecule can be DNA or RNA that directs the expression of a mutant CSP protein. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in mammalian cells. Portions of complete gene sequences are referenced throughout the disclosure as is understood by one of ordinary skill in the art.

Gene sequences encoding mutant CSP proteins described herein can be derived using numerous publicly available programs and can be prepared by synthetic or recombinant methods from the relevant amino acid sequences and other description provided herein.

In embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence.

As indicated, polynucleotide gene sequences encoding more than one portion of an expressed molecule can be operably linked to each other and relevant regulatory sequences. For example, there can be a functional linkage between a regulatory sequence and an exogenous nucleic acid sequence resulting in expression of the latter. For another example, a first nucleic acid sequence can be operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary or helpful, join coding regions, into the same reading frame. Regulatory elements such as insulators, post-regulatory elements, termination signals, etc. may also be included.

A "vector" is a nucleic acid molecule that is capable of transporting another nucleic acid. Vectors may be, e.g., plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

Retroviral vectors (see Miller, et al., 1993, Meth. Enzymol. 217:581-599) can be used. In such embodiments, the gene to be expressed is cloned into the retroviral vector for its delivery into cells. In particular embodiments, a retroviral vector includes all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail about retroviral vectors can be found in Boesen, et al., 1994, Biotherapy 6:291-302; Clowes, et al., 1994, J. Clin. Invest. 93:644-651; Kiem, et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114. Adenoviruses, adena-associated viruses (AAV) and alphaviruses can also be used. See Kozarsky and Wilson, 1993, Current Opinion in Genetics and Development 3:499-503, Rosenfeld, et al., 1991, Science 252:431-434; Rosenfeld, et al., 1992, Cell 68:143-155; Mastrangeli, et al., 1993, J. Clin. Invest. 91:225-234; Walsh, et al., 1993, Proc. Soc. Exp. Bioi. Med. 204:289-300; and Lundstrom, 1999, J. Recept. Signal Transduct. Res. 19: 673-686. Other methods of gene delivery include use of mammalian artificial chromosomes (Vos, 1998, Curr. Op. Genet. Dev. 8:351-359); liposomes (Tarahovsky and lvanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

There are a large number of available viral vectors suitable within the current disclosure, including those identified for human gene therapy applications (see Pfeifer and Verma, 2001, Ann. Rev. Genomics Hum. Genet. 2:177). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles including transgenes are described in, e.g., U.S. Pat. No. 8,119,772; Walchli, et al., 2011, PLoS One 6:327930; Zhao, et al., 2005, J. Immunol. 174:4415; Engels, et al., 2003, Hum. Gene Ther. 14:1155; Frecha, et al., 2010, Mol. Ther. 18:1748; and Verhoeyen, et al., 2009, Methods Mol. Biol. 506:97. Retroviral and lentiviral vector constructs and expression systems are also commercially available.

Targeted genetic engineering approaches may also be utilized. The CRISPR (Clustered Regularly Interspaced Short Palindromic Repeats)/Cas (CRISPR-associated protein) nuclease system is an engineered nuclease system used for genetic engineering that is based on a bacterial system. Information regarding CRISPR-Cas systems and components thereof are described in, for example, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments utilize zinc finger nucleases (ZFNs) as gene editing agents. ZFNs are a class of site-specific nucleases engineered to bind and cleave DNA at specific positions. ZFNs are used to introduce double stranded breaks (DSBs) at a specific site in a DNA sequence which enables the ZFNs to target unique sequences within a genome in a variety of different cells.

For additional information regarding ZFNs and ZFNs useful within the teachings of the current disclosure, see, e.g., U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; 2003/0232410 and US 2009/0203140 as well as Gaj et al., Nat Methods, 2012, 9(8):805-7; Ramirez et al., Nucl Acids Res, 2012, 40(12): 5560-8; Kim et al., Genome Res, 2012, 22(7): 1327-33; Urnov et al., Nature Reviews Genetics, 2010, 11:636-646; Miller, et al. Nature biotechnology 25, 778-785 (2007); Bibikova, et al. Science 300, 764 (2003); Bibikova, et al. Genetics 161, 1169-1175 (2002); Wolfe, et al. Annual review of biophysics and biomolecular structure 29, 183-212 (2000); Kim, et al. Proceedings of the National Academy of Sciences of the United States of America 93, 1156-1160 (1996); and Miller, et al. The EMBO journal 4, 1609-1614 (1985).

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing double DSBs in the DNA, which induce repair mechanisms in cells. Generally, two TALENs must bind and flank each side of the target DNA site for the DNA cleavage domain to dimerize and induce a DSB. For additional information regarding TALENs, see U.S. Pat. Nos. 8,440,431; 8,440,432; 8,450,471; 8,586,363; and 8,697,853; as well as Joung and Sander, Nat Rev Mol Cell Biot, 2013, 14(I):49-55; Beurdeley et al., Nat Commun, 2013, 4: 1762; Scharenberg et al., Curr Gene Ther, 2013, 13(4):291-303; Gaj et al., Nat Methods, 2012, 9(8):805-7; Miller, et al. Nature biotechnology 29, 143-148 (2011); Christian, et al. Genetics 186, 757-761 (2010); Boch, et al. Science 326, 1509-1512 (2009); and Moscou, & Bogdanove, Science 326, 1501 (2009).

Particular embodiments can utilize MegaTALs as gene editing agents. MegaTALs have a sc rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

Particles may be used to administer nucleic acids encoding mutant CSP proteins.

In some embodiments, the delivered nucleic acid includes a plasmid, a cDNA, or an mRNA that can include, e.g., a sequence (e.g., a gene) for expressing a mutant CSP protein.

In particular embodiments, nucleic acids include synthetic mRNA. In particular embodiments, synthetic mRNA is engineered for increased intracellular stability using 5'-capping. Multiple distinct 5'-cap structures can be used to generate the 5'-cap of a synthetic mRNA molecule. For example, the Anti-Reverse Cap Analog (ARCA) cap contains a 5'-5'-triphosphate guanine-guanine linkage where one guanine contains an N7 methyl group as well as a 3'-O-methyl group. Synthetic mRNA molecules may also be capped post-transcriptionally using enzymes responsible for generating 5'-cap structures. For example, recombinant Vaccinia Virus Capping Enzyme and recombinant 2'-O-methyltransferase enzyme can create a canonical 5'-5'-triphosphate linkage between the 5'-most nucleotide of an mRNA and a guanine nucleotide where the guanine contains an N7 methylation and the ultimate 5'-nucleotide contains a 2'-O-methyl generating the Cap1 structure. This results in a cap with higher translational-competency and cellular stability and reduced activation of cellular pro-inflammatory cytokines.

Synthetic mRNA or other nucleic acids may also be made cyclic. Synthetic mRNA may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular.

In the first route, the 5'-end and the 3'-end of the nucleic acid may contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a synthetic mRNA molecule will undergo a nucleophilic attack on the 5'-NHS-ester moiety forming a new 5'-/3'-amide bond.

In the second route, T4 RNA ligase may be used to enzymatically link a 5'-phosphorylated nucleic acid molecule to the 3'-hydroxyl group of a nucleic acid forming a new phosphorodiester linkage. In an example reaction, 1 μg of a nucleic acid molecule can be incubated at 37° C. for 1 hour with 1-10 units of T4 RNA ligase (New England Biolabs, Ipswich, Mass.) according to the manufacturer's protocol. The ligation reaction may occur in the presence of a split oligonucleotide capable of base-pairing with both the 5'- and 3'-region in juxtaposition to assist the enzymatic ligation reaction.

In the third route, either the 5'- or 3'-end of a cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

Particular embodiments can utilize nucleoside modified RNAs, such as pseudouridine or 1-methyl-pseudouridine (see, e.g., US 2018/0303925).

(ii) Multimerization Domains. In particular embodiments, mutant proteins described herein can be expressed with a multimerization domain at, for example, the C-terminus to increase the avidity of the vaccine antigens. Exemplary multimerization domains include C4b multimerization domains such as:

```
Sequence
                                    (SEQ ID NO: 33)
SGRAHAGWETPEGCEQVLTGKRLMQCLPNPEDVKMALEVYKLSLEIEQLE

LQRDSARQSTLDKELVPR (SEQ ID NO: 34)
KKQGDADVCGEVAYIQSVVSDCHVPTAELRTLLEIRKLFLEIQKLKVELQ

GLSKE (SEQ ID NO: 35)
ETPEGCEQVLTGKRLMQCLPNPEDVKMALEVYKLSLEIEQLELQRDSARQ

STLDKEL (SEQ ID NO: 36)
WETPEGCEQVLTGKRLMQCLPNPEDVKMALEVYKLSLEIEQLELQRDSAR

QSTLDKEL (SEQ ID NO: 37)
CEQVLTGKRLMQCLPNPEDVKMALEVYKLSLEIEQLELQRDSARQSTLDK

EL (SEQ ID NO: 38)
ETPEGCEQVLTGKRLMQCLPNPEDVKMALEVYKLSLEIEQLELQRDSARQ

YTLDKEL (SEQ ID NO: 39)
ETPEGCEQVLAGKRLMQCLPNPEDVKMALEVYKLSLEIEQLELQRDRARQ

STLDKEL (SEQ ID NO: 40)
ETPEGCEQVLAGKRLMQCLPNPEDVKMALEVYKLSLEIEQLELQRDRARQ

STWDKEL (SEQ ID NO: 41)
EVPEGCEQVQAGRRLMQCLADPYEVKMALEVYKLSLEIELLELQRDKARK

SSVLRQL (SEQ ID NO: 42)
VVPEGCEHILKGRKTMQCLPNPEDVKMALEIYKLSLDIELLELQRDRAKE

STVQSPV (SEQ ID NO: 43)
EVPKDCEHVFAGKKLMQCLPNSNDVKMALEVYKLTLEIKQLQLQIDKAKH

VDREL (SEQ ID NO: 44)
EYPEDCEQVHEGKKLMQCLPNLEEIKLALELYKLSLETKLLELQIDKEKK

AKAKYSI (SEQ ID NO: 45)
EYPEDCEQVHEGKKLMECLPTLEEIKLALALYKLSLETNLLELQIDKEKK

AKAKYST (SEQ ID NO: 46)
EIAEGCEQVLAGRKIMQCLPKPEDVRTALELYKLSLEIKQLEKKLEKEEK

CTPEVQE (SEQ ID NO: 47)
EYPEGCEQVVTGRKLLQCLSRPEEVKLALEVYKLSLEIEILQTNKLKKEA

FLLREREKNVTCDFNPE (SEQ ID NO: 48)
EYPEGCEQVVTGRKLLKCLSRPEEVKLALEVYKLSLEIALLELQIDKPKD

AS (SEQ ID NO: 49)
EVPENCEQVIVGKKLMKCLSNPDEAQMALQLYKLSLEAELLRLQIVKARQ

GS (SEQ ID NO: 50)
EASEDLKPALTGNKTMQYVPNSHDVKMALEIYKLTLEVELLQLQIQKEKH

TEAH (SEQ ID NO: 51)
VSAEVCEAVFKGQKLLKCLPNAMEVKMALEVYKLSLEIEKLEQEKRKLEI

A (SEQ ID NO: 52)
EVPEECKQVAAGRKLLECLPNPSDVKMALEVYKLSLEIEQLEKEKYVKIQ

EKFSKKEMKQLTSALH (SEQ ID NO: 53)
EVLEDCRIVSRGAQLLHCLSSPEDVHRALKVYKLFLEIERLEHQKEKWIQ

LHRKPQSMK (SEQ ID NO: 54)
EGPEDCEIVNKGRQLLQCLSSPEDVQRALEVYKLSLEIERLEQQREKRTS

VHRKAHYTKVDGP (SEQ ID NO: 55)
EAPEGCEQVLTGRKLMQCLPSPEDVKVALEVYKLSLEIKQLEKERDKLMN

THQKFSEKEEMKDLFFP (SEQ ID NO: 56)
EVPEGCEQVLTGKKLMQCLPNPEDVKMALEVYKLSLEIELLELQIDKARQ

GS (SEQ ID NO: 57)
GCEQVLTGKRLMQCLPNPEDVKMALEVYKLSLEIEQLELQRDSARQS (SEQ ID NO: 58)
ETPEGCEQVLTGKRLMQCLPNPEDVKMALEVYKLSLEIEQLELQRDSARQ

S (SEQ ID NO: 59)
GSEQVLTGKRLMQSLPNPEDVKMALEVYKLSLEIEQLELQRDSARQSTLD

KEL (SEQ ID NO: 60)
ETPEGCEQVLTGKRLMQCLPNPEDVKMALEIYKLTLEIEQLELQRDSARQ

STLDKEL (SEQ ID NO: 61)
ETPEGCEQVLTGKRLMQCLPNPEDVKMALEIYKLSLEIKQLELQRDSARQ

STLDKEL
```

-continued (SEQ ID NO: 62)
EGCEQILTGKRLMQCLPDPEDVKMALEIYKLSLEIKQLELQRDRARQSTL (SEQ ID NO: 63)
ETPEGCEQVLTGKRLMQCLPNPEDVKMALEVYKLSLEIKQLELQRDRARQ

STLDKEL (SEQ ID NO: 64)
EGCEQILTGKRLMQCLPNPEDVKMALEIYKLSLEIEQLELQRDRARQSTL

DK (SEQ ID NO: 65)
WETPEGCEQVLTGKRLMQCLPNPEDVKMALEVYKLSLEIEQLELQRDSAR

QSTLDKELVPR

Exemplary heptamerization domains include:

| Sequence |
|---|
| AHAGWETPEGCEQVLTGKRLMQCLPNPEDVKMALEVYKLSLEIEQLELQ RDSARQSTLDKEL (SEQ ID NO: 66; Human) |
| SKKQGDADVCGEVAYIQSVVSDCHVPTEDVKTLLEIRKLFLEIQKLKVE LQGLSKE (SEQ ID NO: 67; Chicken) |
| SKKQGDADVCGEVAYIQSVVSDCHVPTAELRTLLEIRKLFLEIQKLKVE LQGLSKE (SEQ ID NO: 68; Modified Chicken) |

Ferritin can also be used to multimerize vaccines.

(iii) Linkers and Cleavage Components. Particular embodiments may include a linker sequence between a vaccine antigen and multimerization domain or between other discrete components of an expressed molecule, such as between a CSP NTD, repeat domain, and/or CTD. Particular exemplary linkers include flexible Gly-Ser linkers. Such linkers are known to those of skill in the art. One exemplary Gly-Ser linker includes Ac-Cys-Gly-Gly-Gly (SEQ ID NO: 69). Additional Gly-Ser linkers include GST-SGSGKPGSGEGSTKG (SEQ ID NO: 70) and SGRAHAG (SEQ ID NO: 71). Further examples include a linker that includes (Gly)n, where n=1 to 10 (e.g., n=1, 2, 3, 4, 5, 6, 7, 8, 9, or 10); (Ser)n, where n=1 to 10 (e.g., n=1, 2, 3, 4, 5, 6, 7, 8, 9, or 10), (Ala)n, where n=1 to 10 (e.g., n=1, 2, 3, 4, 5, 6, 7, 8, 9, or 10), (Gly-Ser)n, where n=1 to 10 (e.g., n=1, 2, 3, 4, 5, 6, 7, 8, 9, or 10), (Gly-Ser-Ser-Gly)n, where n=1 to 10 (e.g., n=1, 2, 3, 4, 5, 6, 7, 8, 9, or 10), (Gly-Ser-Gly)n, where n=1 to 10 (e.g., n=1, 2, 3, 4, 5, 6, 7, 8, 9, or 10), (Gly-Ser-Ser)n, where n=1 to 10 (e.g., n=1, 2, 3, 4, 5, 6, 7, 8, 9, or 10), (Gly-Ala)n, where n=1 to 10 (e.g., n=1, 2, 3, 4, 5, 6, 7, 8, 9, or 10), or any combination thereof. If a more rigid linker is appropriate, a proline-rich linker can be used.

Particular embodiments can include cleavage components that allow separation of a stabilized N-terminus from a co-expressed epitope. In particular embodiments, the cleavage component can be a self-cleaving peptide, such as a self-cleaving "2A" peptide. 2A peptides function by causing the ribosome to skip the synthesis of a peptide bond at a defined location, leading to production of two proteins from one mRNA. The 2A sequences are short (e.g., 20 amino acids), facilitating use in size-limited constructs, and proteins are produced at a 1:1 ratio. Particular examples include T2A (GSG)EGRGSLLTCGDVEENPGP (SEQ ID NO: 72), P2A (GSG)ATNFSLLKQAGDVEENPGP (SEQ ID NO: 73), E2A (GSG)QCTNYALLKLAGDVESNPGPP (SEQ ID NO: 74), and F2A (GSG)VKQTLNFDLLKLAGD-VESNPGP (SEQ ID NO: 75).

In particular embodiments, nucleic acids can include an internal ribosome entry site (IRES) sequence. IRES are non-coding structured RNA sequences that allow ribosomes to initiate translation at a second internal site on a mRNA molecule, leading to production of two proteins from one mRNA. However, IRES driven translation is less efficient than 2A driven translation, which can lead to lower expression of the second protein in the transcript.

(iv) Particles. CSP proteins and/or nucleic acids disclosed herein can be associated with the following particle types:

| Nanoparticles | Number of Antigens | Vaccine usage | References |
|---|---|---|---|
| HBsAg | N/A | Hep B, RTS, S, R21 | Collins et al. 2017 |
| Chikungunya | 240 | VLP | Akhata et al. 2010 |
| HPV | 360 | HPV | HPV vaccine |
| Luminase synthase | 60 | HIV | Jardine et al. 2013 |
| Ferritin | 24 | Flu | Masaru et al. 2015 |
| I53-50 | 60 | RSV, Flu | Bale et al. 2017 |

In particular embodiments, CSP proteins and/or nucleic acids can be delivered using liposomes. Liposomes are microscopic vesicles including at least one concentric lipid bilayer. Vesicle-forming lipids are selected to achieve a specified degree of fluidity or rigidity of the final complex. In particular embodiments, liposomes provide a lipid composition that is an outer layer surrounding a porous particle.

Liposomes can be neutral (cholesterol) or bipolar and include phospholipids, such as phosphatidylcholine (PC), phosphatidylethanolamine (PE), phosphatidylinositol (PI), and sphingomyelin (SM) and other type of bipolar lipids including dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, DDAB, dioctadecyl dimethyl ammonium chloride (DODAC), 1,2-dimyristoyl-3-trimethylammonium propane (DMTAP), DOTAP, DOTMA, DC-Chol, phosphatidic acid (PA), dipalmitoylphosphatidylglycerol (DPPG), dioleoylphosphatidylglycerol, DOPG, and dicetylphosphate. In particular embodiments, lipids used to create liposomes disclosed herein include cholesterol, hydrogenated soy phosphatidylcholine (HSPC) and, the derivatized vesicle-forming lipid PEG-DSPE.

Methods of forming liposomes are described in, for example, U.S. Pat. Nos. 4,229,360; 4,224,179; 4,241,046; 4,737,323; 4,078,052; 4,235,871; 4,501,728; and 4,837,028, as well as in Szoka et al., Ann. Rev. Biophys. Bioeng. 9:467 (1980) and Hope et al., Chem. Phys. Lip. 40:89 (1986).

Particular embodiments can utilize lipid nanoparticles (LNPs) as described in US2018/0303925. Particles as described in Pardi et al., Nature Communications (2018) 9:3361 can also be used. Particular embodiments can include mRNA and poly(C) RNA (Sigma) encapsulated in LNPs using a self-assembly process. In particular embodiments, an aqueous solution of mRNA at pH=4.0 can be rapidly mixed with a solution of lipids dissolved in ethanol, as described in Maier, et al., Mol. Ther. 21, 1570-1578 (2013). The LNPs can include an ionizable cationic lipid including phosphatidylcholine/cholesterol/PEG-lipid (50:10:38.5:1.5 mol/mol) with RNA encapsulated at an RNA to total lipid ratio of 0.05 (wt/wt). Particular embodiments can utilize LNPs with a diameter of 80 nm as measured by dynamic light scattering using a Zetasizer Nano ZS (Malvern Instruments Ltd., Malvern, UK) instrument.

In particular embodiments, particles can include features that enhance the delivery and/or expression of a nucleic acid. For example, in particular embodiments, the particle includes a carrier molecule that condenses and protects a nucleic acid from enzymatic degradation. Such carriers are positively charged (e.g., poly($\beta$-amino ester)). Additional examples of positively charged polymers include polyamines; polyorganic amines (e.g., polyethyleneimine (PEI), polyethyleneimine celluloses); poly(amidoamines) (PAMAM); polyamino acids (e.g., polylysine (PLL), polyarginine); polysaccharides (e.g, cellulose, dextran, DEAE dextran, starch); spermine, spermidine, poly(vinylbenzyl trialkyl ammonium), poly(4-vinyl-N-alkyl-pyridiumiun), poly(acryloyl-trialkyl ammonium), and Tat proteins.

Examples of positively charged lipids include esters of phosphatidic acid with an aminoalcohol, such as an ester of dipalmitoyl phosphatidic acid or distearoyl phosphatidic acid with hydroxyethylenediamine. More particular examples of positively charged lipids include 3$\beta$-[N—(N', N'-dimethylaminoethyl)carbamoyl) cholesterol (DC-chol); N,N'-dimethyl-N,N'-dioctacyl ammonium bromide (DDAB); N,N'-dimethyl-N,N'-dioctacyl ammonium chloride (DDAC); 1,2-dioleoyloxypropyl-3-dimethyl-hydroxyethyl ammonium chloride (DORI); 1,2-dioleoyloxy-3-[trimethylammonio]-propane (DOTAP); N-(1-(2,3-dioleyloxy) propyl)-N,N,N-trimethylammonium chloride (DOTMA); dipalmitoylphosphatidylcholine (DPPC); 1,2-dioctadecyloxy-3-[trimethylammonio]-propane (DSTAP); and the cationic lipids described in e.g. Martin et al., Current Pharmaceutical Design 2005, 11, 375-394.

Examples of negatively charged polymers include alginic acids; carboxylic acid polysaccharides; carboxymethyl cellulose; carboxymethyl cellulose-cysteine; carrageenan (e.g., Gelcarin® 209, Gelcarin® 379); chondroitin sulfate; glycosaminoglycans; mucopolysaccharides; negatively charged polysaccharides (e.g., dextran sulfate); poly(acrylic acid); poly(D-aspartic acid); poly(L-aspartic acid); poly(L-aspartic acid) sodium salt; poly(D-glutamic acid); poly(L-glutamic acid); poly(L-glutamic acid) sodium salt; poly(methacrylic acid); sodium alginate (e.g., Protanal® LF 120M, Protanal® LF 200M, Protanal® LF 200D); sodium carboxymethyl cellulose (CMC); sulfated polysaccharides (heparins, agaropectins); pectin, gelatin and hyaluronic acid.

Neutrally charged polymers include zwitterionic polymers. Zwitterionic refers to the property of overall charge neutrality while having both a positive and a negative electrical charge. Zwitterionic polymers can behave like regions of cell membranes that resist cell and protein adhesion.

Zwitterionic polymers include zwitterionic constitutional units including pendant groups (i.e., groups pendant from the polymer backbone) with zwitterionic groups. Exemplary zwitterionic pendant groups include carboxybetaine groups (e.g., -Ra-N+(Rb)(Rc)-Rd-CO2-, where Ra is a linker group that covalently couples the polymer backbone to the cationic nitrogen center of the carboxybetaine groups, Rb and Rc are nitrogen substituents, and Rd is a linker group that covalently couples the cationic nitrogen center to the carboxy group of the carboxybetaine group).

In particular embodiments, polymers can include "star shaped polymers," which refer to branched polymers in which two or more polymer branches extend from a core. The core is a group of atoms having two or more functional groups from which the branches can be extended by polymerization.

In particular embodiments, the branches are zwitterionic or negatively-charged polymeric branches. For star polymers, the branch precursors can be converted to zwitterionic or negatively-charged polymers via hydrolysis, ultraviolet irradiation, or heat. The polymers also may be obtained by any polymerization method effective for polymerization of unsaturated monomers, including atom transfer radical polymerization (ATRP), reversible addition-fragmentation chain transfer polymerization (RAFT), photo-polymerization, ring-opening polymerization (ROP), condensation, Michael addition, branch generation/propagation reaction, or other reactions.

Blends of lipids and polymers in any concentration and in any ratio can also be used. Blending different polymer types in different ratios using various grades can result in characteristics that borrow from each of the contributing polymers. Various terminal group chemistries can also be adopted.

Without limiting the foregoing, particular embodiments disclosed herein can also utilize porous particles constructed from any material capable of forming a porous network. Exemplary materials include metals, transition metals and metalloids. Exemplary metals, transition metals and metalloids include lithium, magnesium, zinc, aluminum and silica. In particular embodiments, the porous nanocarriers include silica. The exceptionally high surface area of mesoporous silica (exceeding 1,000 m2/g) enables nucleic acid loading at levels exceeding conventional DNA carriers such as liposomes.

Particles can be formed in a variety of different shapes, including spheroidal, cuboidal, pyramidal, oblong, cylindrical, toroidal, and the like. The vaccines can be included in a variety of ways. For example, CSP proteins and/or nucleic acids can be associated (e.g., covalently and/or non-covalently) with the surface or close underlying vicinity of the surface of the particles. In particular embodiments, the CSP proteins and/or nucleic acids can be incorporated in a porous particle e.g., integrated in the material of a porous particle. For example, CSP proteins and/or nucleic acids can be incorporated into a polymer matrix of polymer particles that biodegrade following administration.

(v) Vaccine Adjuvants. CSP proteins and/or nucleic acids can be administered as vaccines. Vaccines are often administered with vaccine adjuvants. The term "adjuvant" refers to material that enhances the immune response to an antigen and is used herein in the customary use of the term. The precise mode of action is not understood for all adjuvants, but such lack of understanding does not prevent their clinical use for a wide variety of vaccines.

Exemplary vaccine adjuvants, include any kind of Toll-like receptor ligand or combinations thereof (e.g. CpG, Cpg-28 (a TLR9 agonist), Polyriboinosinic polyribocytidylic acid (Poly(I:C)), α-galactoceramide, MPLA, Motolimod (VTX-2337, a novel TLR8 agonist developed by VentiRx), IMO-2055 (EMD1201081), TMX-101 (imiquimod), MGN1703 (a TLR9 agonist), G100 (a stabilized emulsion of the TLR4 agonist glucopyranosyl lipid A), Entolimod (a derivative of Salmonella flagellin also known as CBLB502), Hiltonol (a TLR3 agonist), and Imiquimod), and/or inhibitors of heat-shock protein 90 (Hsp90), such as 17-DMAG (17-dimethylaminoethylamino-17-demethoxygeldanamycin).

In particular embodiments a squalene-based adjuvant can be used. Squalene is part of the group of molecules known as triterpenes, which are all hydrocarbons with 30 carbon molecules. Squalene can be derived from certain plant sources, such as rice bran, wheat germ, amaranth seeds, and olives, as well as from animal sources, such as shark liver oil. In particular embodiments, the squalene-based adjuvant is MF59® (Novartis, Basel, Switzerland). An example of a squalene-based adjuvant that is similar to MF59® but is designed for preclinical research use is Addavax™ (InvivoGen, San Diego, Calif.). MF59 has been FDA approved for use in an influenza vaccine, and studies indicate that it is safe for use during pregnancy (Tsai T, et al. Vaccine. 2010. 17:28(7):1877-80; Heikkinen T, et al. Am J Obstet Gynecol. 2012. 207(3):177). In particular embodiments, squalene-based adjuvants can include 0.1%-20% (v/v) squalene oil. In particular embodiments, squalene-based adjuvants can include 5% (v/v) squalene oil.

In particular embodiments the adjuvant alum can be used. Alum refers to a family of salts that contain two sulfate groups, a monovalent cation, and a trivalent metal, such as aluminum or chromium. Alum is an FDA approved adjuvant. In particular embodiments, vaccines can include alum in the amounts of 1-1000 ug/dose or 0.1 mg-10 mg/dose. In particular embodiments, the adjuvant Vaxfectin® (Vical, Inc., San Diego, Calif.) can be used. Vaxfectin® is a cationic lipid based adjuvant.

In particular embodiments, one or more STING agonists are used as a vaccine adjuvant. "STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein and is encoded by the gene TMEM173 in human. Activation of STING leads to production of Type I interferons (e.g. IFN-α and IFN-β), via the IRF3 (interferon regulatory factor 3) pathway; and to production of pro-inflammatory cytokines (e.g. TNF-α and IL-1β), via the NF-κB pathway and/or the NLRP3 inflammasome.

Human and murine STING are naturally activated two ways: via binding of exogenous (3', 3) cyclic dinucleotides (c-diGMP, c-diAMP and c-GAMP) that are released by invading bacteria or archaea; and via binding of (2',3')cyclic guanosine monophosphate-adenosine monophosphate ((2', 3')c-GAMP), an endogenous cyclic dinucleotide that is produced by the enzyme cyclic GMP-AMP synthase (cGAS; also known as C6orf150 or MB21D1) in the presence of exogenous double-stranded DNA (e.g. that released by invading bacteria, viruses or protozoa).

The term "STING agonist" refers to a substance that activates the STING receptor in vitro or in vivo. A compound can be deemed a STING agonist if: (i) induces Type I interferons in vitro in human or animal cells that contain STING; and (ii) does not induce Type I interferons in vitro in human or animal cells that do not contain STING or does not contain functioning STING. A typical test to ascertain whether a ligand is a STING agonist is to incubate the ligand in a wild-type human or animal cell line and in the corresponding cell line in which the STING coding gene has been genetically inactivated by a few bases or a longer deletion (e.g. a homozygous STING knockout cell line). An agonist of STING will induce Type I interferon in the wild-type cells but will not induce Type I interferon in the cells in which STING is inactivated.

In particular embodiments, STING agonists include cyclic molecules with one or two phosphodiester linkages, and/or one or two phosphorothioate diester linkages, between two nucleotides. This includes (3',5')-(3',5') nucleotide linkages (abbreviated as (3',3')); (3',5')-(2',5') nucleotide linkages (abbreviated as (3',2')); (2',5')-(3',5') nucleotide linkages (abbreviated as (2',3')); and (2',5')-(2',5') nucleotide linkages (abbreviated as (2',2')). "Nucleotide" refers to any nucleoside linked to a phosphate group at the 5', 3' or 2' position of the sugar moiety.

In particular embodiments, STING agonists include compounds of the formula:

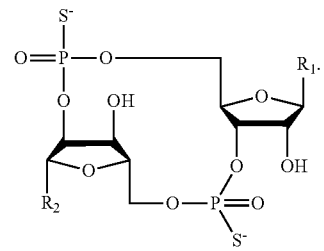

In particular embodiments, R1 and R2 may be independently 9-purine, 9-adenine, 9-guanine, 9-hypoxanthine, 9-xanthine, 9-uric acid, or 9-isoguanine, as shown below:

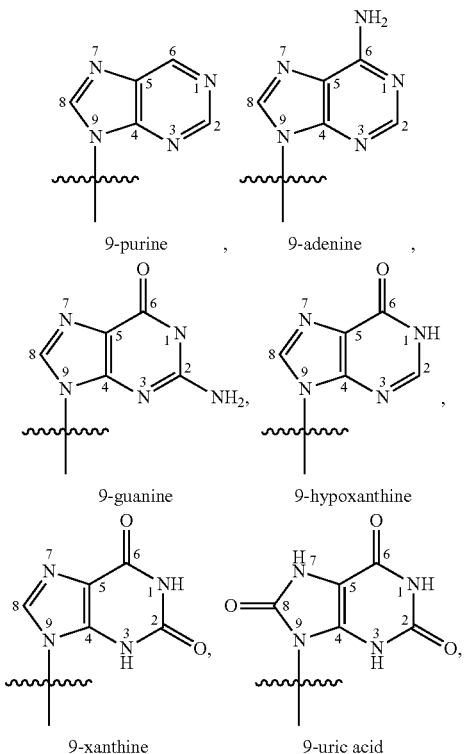

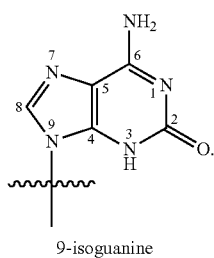

9-isoguanine

In particular embodiments, the STING agonist can include dithio-(RP, RP)-[cyclic[A(2',5')pA(3',5')p]] (also known as 2'-5', 3'-5' mixed phosphodiester linkage (ML) RR-S2 c-di-AMP or ML RR-S2 CDA), ML RR-S2-c-di-GMP (ML-CDG), ML RR-S2 cGAMP, or any mixtures thereof.

The structure of c-diGMP includes

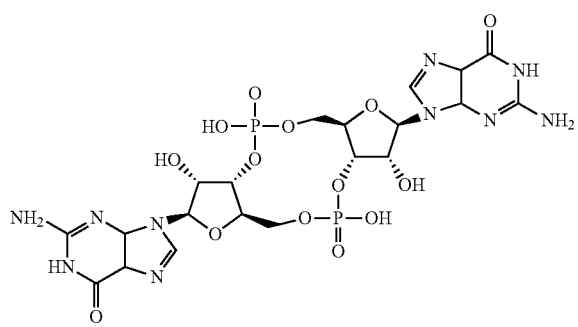

The structure of c-diAMP includes:

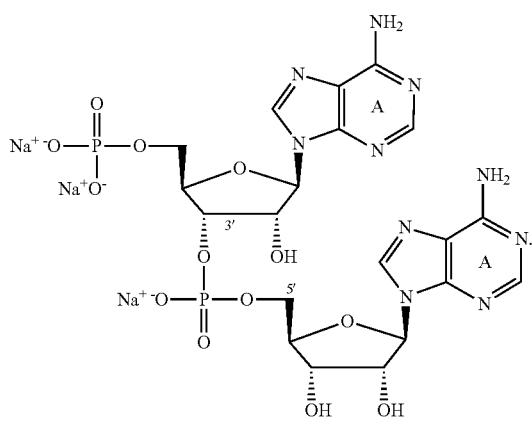

The structure of c-GAMP includes:

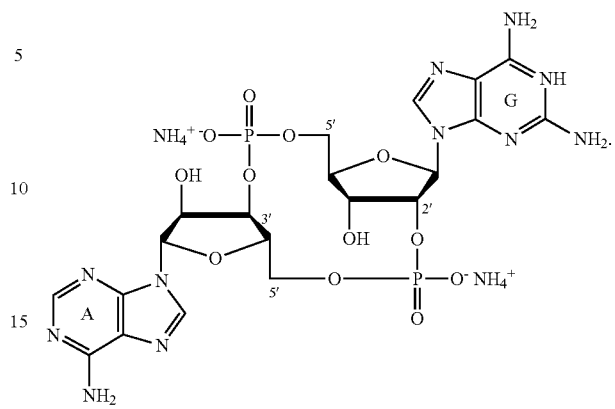

Additional particular examples of STING agonists include c-AIMP; (3',2')c-AIMP; (2',2')c-AIMP; (2',3')c-AIMP; c-AIMP(S); c-(dAMP-dTMP); c-(dAMP-2'FdIMP); c-(2'FdAMP-2'FdIMP); (2',3')c-(AMP-2'FdIMP); c-[2'FdAMP(S)-2'FdIMP(S)]; c-[2'FdAMP(S)-2'FdIMP(S)] (POM)2; and DMXAA. Additional examples of STING agonists are described in WO2016/145102.

Other immune stimulants can also be used as vaccine adjuvants. Additional exemplary small molecule immune stimulants include TGF-β inhibitors, SHP-inhibitors, STAT-3 inhibitors, and/or STAT-5 inhibitors. Exemplary siRNA capable of down-regulating immune-suppressive signals or oncogenic pathways (such as kras) can be used whereas any plasmid DNA (such as minicircle DNA) encoding immune-stimulatory proteins can also be used.

Exemplary cytokines include IL-2, IL-7, IL-12, IL-15, IL-18, IL-21, TNFα, IFN-α, IFN-β, IFN-γ, or GM-CSF. In particular embodiments, the immune stimulant may be a cytokine and or a combination of cytokines, such as IL-2, IL-12 or IL-15 in combination with IFN-α, IFN-β or IFN-γ, or GM-CSF, or any effective combination thereof, or any other effective combination of cytokines. The above-identified cytokines stimulate TH1 responses, but cytokines that stimulate TH2 responses may also be used, such as IL-4, IL-10, IL-11, or any effective combination thereof. Also, combinations of cytokines that stimulate TH1 responses along with cytokines that stimulate TH2 responses may be used.

Immune stimulants derived from the molecules noted in the preceding paragraphs can also be used. For example, RLI is an IL-15-IL-15 receptor-α fusion protein that exhibits 50-fold greater potency than IL-15 alone.

(vi) Compositions. The nucleic acids, particle, protein vaccine antigens, and/or vaccine adjuvants disclosed herein (individually, collectively, or in grouped combinations referred to as "active ingredients") can be provided as part of compositions formulated for administration to subjects.

In particular embodiments, the active ingredients are provided as part of a composition that can include, for example, at least 0.1% w/v or w/w of active ingredient(s); at least 1% w/v or w/w of active ingredient(s); at least 10% w/v or w/w of active ingredient(s); at least 20% w/v or w/w of active ingredient(s); at least 30% w/v or w/w of active ingredient(s); at least 40% w/v or w/w of active ingredient(s); at least 50% w/v or w/w of active ingredient(s); at least 60% w/v or w/w of active ingredient(s); at least 70% w/v or w/w of active ingredient(s); at least 80% w/v or w/w of active ingredient(s); at least 90% w/v or w/w of active ingredient(s); at least 95% w/v or w/w of active ingredient(s); or at least 99% w/v or w/w of active ingredient(s).

The compositions disclosed herein can be formulated for administration by, for example, injection, inhalation, infusion, perfusion, lavage or ingestion. The compositions can further be formulated for, for example, intravenous, intradermal, intraarterial, intranodal, intralymphatic, intraperitoneal, intralesional, intraprostatic, intravaginal, intrarectal, topical, intrathecal, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, topical, intrathecal, intramuscular, intravesicular, oral and/or subcutaneous injection.

For injection, compositions can be formulated as aqueous solutions, such as in buffers including Hanks' solution, Ringer's solution, or physiological saline. The aqueous solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

For administration by inhalation, compositions can be formulated as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the therapeutic and a suitable powder base such as lactose or starch.

Any composition formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers or polysaccharides.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as sparingly soluble salts.

Additionally, compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for a few weeks up to over 100 days.

(vii) Kits. Combinations of active ingredients can also be provided as kits. Kits can include containers including one or more nucleic acids encoding a mutant CSP protein, mutant CSP proteins, particles, protein vaccine antigens, and/or vaccine adjuvants described herein formulated individually, or in various combinations. Generally, the kit will include the nucleic acid, mutant CSP protein, particle, protein vaccine antigen, and/or vaccine adjuvants specific to enhance vaccine efficacy against a particular infectious agent, such as those described elsewhere herein.

Kits can also include a notice in the form prescribed by a governmental agency regulating the manufacture, use, or sale of pharmaceuticals or biological products, which notice reflects approval by the agency of manufacture, use, or sale for human administration. The notice may state that the provided active ingredients can be administered to a subject as provided or following production using components provided within the kit. The kits can include further instructions for using the kit, for example, instructions regarding preparation of mutant CSP proteins, particle, vaccines, and/or vaccine adjuvants for administration; proper disposal of related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In particular embodiments, kits can also include some or all of the necessary medical supplies needed to use the kit effectively, such as syringes, ampules, tubing, facemask, an injection cap, sponges, sterile adhesive strips, Chloraprep, gloves, and the like. Variations in contents of any of the kits described herein can be made. The instructions of the kit will direct use of the active ingredients to effectuate a new clinical use described herein.

(viii) Methods of Use in Subjects. Once formed, the compositions find use in a number of applications. In particular embodiments, the compositions find use in the treatment of disease. "Treatment" refers to both therapeutic treatment and prophylactic treatment or preventative measures, wherein the object is to prevent, reduce the occurrence or severity of, or slow down or lessen a targeted pathologic condition or disorder, including malaria. "Subjects" include those in need of treatment, such as, those with a condition (e.g., an infection), as well as those prone to have or develop an a condition (e.g., an infection), or those in whom a condition is to be prevented, such as those in a high risk group for exposure to a pathogen.

Thus, in various exemplary embodiments, a subject can be a human subject. Other types of subjects include veterinary animals (dogs, cats, reptiles, birds, etc. and also including animals found within zoos), livestock (horses, cattle, goats, pigs, chickens, etc.), and research animals (monkeys, rats, mice, fish, etc.).

The compositions can be administered prophylactically in subjects who are at risk of developing a condition (e.g., malaria), or who have been exposed an agent leading to such an infection, to prevent, reduce, or delay the development of the infection or associated disease. For example, the compositions can be administered to a subject likely to have been exposed to malaria, or to a subject who is at high risk for exposure to malaria.

In particular embodiments, compositions can be administered to a subject in a therapeutically effective amount. A "therapeutically effective amount" is an amount sufficient to produce a desired physiological effect and/or an amount capable of achieving a desired result, particularly for treatment of a disorder or disease condition, including reducing or eliminating one or more symptom of the disorder or disease or prevention or delaying the onset of at least one a disease symptom. Therapeutically effective amounts can provide therapeutic treatments and/or prophylactic treatments.

Particular uses of the compositions include use as prophylactic vaccines. Vaccines increase the immunity of a subject against a particular disease caused by an infectious pathogen. Therefore, "vaccine" can refer to a treatment that increases the immunity of a subject against an infectious pathogen. Therefore, in some embodiments, a vaccine may be administered prophylactically, for example to a subject that is immunologically naive (e.g., no prior exposure or experience with an infectious pathogen). In some embodiments, a vaccine may be administered therapeutically to a subject who has been exposed to an infectious pathogen. Thus, a vaccine can be used to ameliorate a symptom associated with an infectious pathogen.

In particular embodiments, a vaccine is a therapeutically effective composition including one or more active ingredients disclosed herein that induce a B cell and/or T cell mediated or supported immune response in a subject against a condition. The skilled artisan will appreciate that the immune system generally is capable of producing an innate immune response and an adaptive immune response. An innate immune response generally can be characterized as not being substantially antigen specific and/or not generating immune memory. An adaptive immune response can be characterized as being substantially antigen specific, maturing over time (e.g., increasing affinity and/or avidity for antigen), and in general can produce immunologic memory. Even though these and other functional distinctions between innate and adaptive immunity can be discerned, the skilled artisan will appreciate that the innate and adaptive immune systems can be integrated and therefore can act in concert.

"Immune response" refers to a response of the immune system to a vaccine antigen. In various exemplary embodiments, an immune response to a vaccine antigen can be an innate and/or adaptive response. In some embodiments, an adaptive immune response can be a "primary immune response" which refers to an immune response occurring on the first exposure of a "naive" subject to a vaccine antigen. For example, in the case of a primary antibody response, after a lag or latent period of from 3 to 14 days depending on, for example, the composition, dose, and subject, antibodies to the vaccine antigen can be produced. Generally, IgM production lasts for several days followed by IgG production and the IgM response can decrease. Antibody production can terminate after several weeks but memory cells can be produced. In some embodiments, an adaptive immune response can be a "secondary immune response", "anamnestic response," or "booster response" which refer to the immune response occurring on a second and subsequent exposure of a subject to a vaccine antigen disclosed herein. Generally, in a secondary immune response, memory cells respond to the vaccine antigen and therefore the secondary immune response can differ from a primary immune response qualitatively and/or quantitatively. For example, in comparison to a primary antibody response, the lag period of a secondary antibody response can be shorter, the peak antibody titer can be higher, higher affinity antibody can be produced, and/or antibody can persist for a greater period of time. "Immune responses" can also be measured by expansion, persistence, and/or activity of B cells and/or memory T cells (e.g., TCM and/or TEM).

The actual dose of active ingredients administered to a particular subject can be determined by a physician, veterinarian, or researcher taking into account parameters such as physical and physiological factors including target, body weight, presence and/or severity of infection, stage of infection, previous or concurrent therapeutic interventions, idiopathy of the subject, and route of administration.

For administration, therapeutically effective amounts (also referred to herein as doses) can be initially estimated based on results from in vitro assays and/or animal model studies.

Exemplary doses of compositions include 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240 or 250 µg/kg body mass or mg/kg body mass although higher and/or lower doses can be used. The number of doses that can be administered as a function of time can be from 1, 2, 3, 4 or 5 doses over 1, 2, 3, 4, 5 or 6 weeks but can be increased or decreased depending, for example, on the immune status of a subject.

In particular embodiments, a composition can be administered initially, and thereafter maintained by further administration. For example, a composition can be administered by intramuscular injection. The subject's levels are then maintained by an oral dosage form, although other forms of administration, dependent upon the patient's condition, may be used. In the instance of a vaccine and particle composition, the composition may be administered as a single dose, or the composition may incorporate set booster doses. For example, booster doses may include variants of vaccine antigens to provide protection against multiple clades of infectious agents.

In particular embodiments, active ingredients for administration in one or more compositions can be (i) a nucleic acid and/or a nucleic acid within a particle, (ii) a protein vaccine antigen (optionally associated with a particle) and (iii) a vaccine adjuvant. In particular embodiments, when included in combinations, the substituents in the combination can be provided in exemplary ratios such as: 1:1:1; 1:2:1; 1:3:1; 1:4:1; 1:5; 1; 1:10:1; 1:2:2; 1:2:3; 1:3:4; 1:4:2; 1:5:3; 9:10:20; 5:2:1; 5:3:11; 5:4:1; 5:5; 1; 5:100:1; 5:20:2; 5:2:3; 5:14:200; 5:10:20; or additional beneficial ratios depending on the number and identity of substituents in a combination to reach an intended effect. The substituents in a combination can be provided within the same composition or within different compositions, as will be understood by one of ordinary skill in the art.

Therapeutically effective amounts can be achieved by administering single or multiple doses during the course of a treatment regimen (e.g., QID, TID, BID, daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly).

(ix) Exemplary Experimental Procedures. Protein expression and purification, affinity measurements, X-ray crystallography and cryo-EM can be performed reproducibly as follows:

Antibody isolation can be performed according to the methods described in Kisalu et al., Nat Med. 2018; 24(4): 408-16 and Krishnamurty et al., Immunity. 2016; 45(2):402-14.

Protein and antibody expression and production. Following sequence verification, expression plasmids for all malaria proteins and antibodies can be transiently transfected into mammalian HEK293EBNA cells adapted for suspension in serum free media. Soluble recombinant malaria proteins can be purified from the supernatant by passage over $Ni^{2+}$-NTA agarose and purified over size exclusion chromatography (SEC) to assess the size, stability and monodispersity of each sample. For antibody IgGs, plasmids coding for the heavy and light chains can co-transfected and the antibody can be purified using protein A agarose. For structural studies, purified IgGs can be digested to antigen binding fragment (Fab) using Lys C and further purified by SEC. Alternatively, a stop codon and a 6×HIS-tag can be introduced in the hinge region of the heavy chain by site-directed mutagenesis and Fabs can be transiently expressed and purified using $Ni^{2+}$-NTA beads and SEC. Complexes can then be made using excess of Fabs or malaria proteins and further purified by SEC before being subjected to X-ray crystallography and/or cryo-EM. Malaria proteins to be used as immunogens and any unused protein samples for structural analysis can be flash-frozen in liquid nitrogen and kept at −80° C. until further use.

Antibody antigenicity and affinity measurements. To understand epitopes recognized by antibodies generated against immunogen constructs described herein (and others), antigenicity characterization can be performed by ELISA, affinity measurement by BioLayer Interferometry (BLI) and Isothermal Titration calorimetry (ITC). ELISA provides qualitative binding information. BLI determines the affinity of antibodies for antigens by providing association and dissociation rate constants for Fabs and/or IgGs. ITC allows estimation of the binding events (one or more) and the stoichiometry of binding, which can be compared to values derived via direct observation of single particles by EM. ITC also determines the enthalpic and entropic contributions to binding, providing the basis for conformational changes associated with antibody binding.

Structures by X-ray crystallography. To obtain the structures of the antibodies with their epitope using X-ray crystallography, variational crystallograph, which involves the crystallization of protein complexes obtained from a large matrix of proteins including a combination of antibodies and malaria proteins can be used. Variational crystallography is described in Kwong et al., J Biol Chem. 1999; 274(7):4115-23 and increases successfully obtaining crystals that will diffract X-rays at high resolution. The presence of the Fabs often aids in the crystallization of proteins due to the additional lattice contacts that can be formed and the ability of some Fabs to stabilize a particular conformation of the protein. The malaria proteins and antibodies can also be crystallized unliganded to visualize if conformational changes are induced upon binding. Additionally, structures of unbound Fabs can assist with phasing of the complex structure. Each complex can be subjected to sitting-drop crystallization trials with both sparse matrix and systematic grid screens, which include numerous crystallization conditions of buffer, salt and precipitant. The initial screens can be set up using a Formulatrix NT8 robot, and will consume 100 nL of protein per drop, to minimize the amount of protein needed. Trays can be robotically inspected and imaged by a Formulatrix Rock Imager 182, and initial crystallization hits will be reproduced and optimized manually. Commercially available additive screens, as well as microseed-matrix screening, can also be used to improve crystal size and order (see, e.g., Ireton & Stoddard, Acta Crystallogr D Biol Crystallogr. 2004; 60(Pt 3):601-5). Once suitable crystals have been obtained, they can be flash frozen in liquid nitrogen for data collection. X-ray diffraction data can be collected using synchrotron radiation. Once atomic-level-resolution data have been collected, they can be indexed, scaled and merged with HKL2000 as described in Battye et al., Acta Crystallogr D Biol Crystallogr. 2011; 67(Pt 4):271-81. To solve the structures, either molecular replacement or other phasing techniques can be used.

Structures by single particle cryo-EM: Protein samples of interest can be screened by nsEM to identify constructs suitable for further structural studies. Negative-stain data can be collected on a Tecnai Spirit microscope with a Gatan CCD camera using Leginon automated acquisition software as described in Subway et al., J Struct Biol. 2005; 151(1): 41-60.

Single particles can be isolated from micrographs. Low-resolution 2D and 3D reconstructions can be calculated using cisTEM (Grant et al., Elife. 2018; 7 (doi: 10.7554/eLife.35383) to determine feasibility for high-resolution cryo-EM studies. Promising samples can be flash frozen on holey carbon films, and screened for the appropriate particle density and angular distribution, as described in Borst et al., Elife. 2018; 7 (doi: 10.7554/eLife.37688). High-resolution datasets can be collected on the U W Titan Krios E M and K2 Summit direct detector. Using this platform, near-atomic resolution (3.7 Å) of protein in complex with Fabs can be obtained (Borst et al., Elife. 2018; 7 (doi: 10.7554/eLife.37688). Data collection takes 2-3 days, while image analysis and data processing using Relion (Zivanov et al., Elife. 2018; 7 (doi: 10.7554/eLife.42166) take several weeks to yield maps that can be interpreted at <4 Å resolution. In addition, the phasing method described in Jackson et al., Nature Protocols. 2015; 10(9):1275-84 can be used by using a cryo-EM map-fragment to phase diffraction data, which provides another example of the benefits of employing both X-ray crystallography and cryo-EM methodologies.

Immunogen Design validation. Purity and antigenicity of immunogen designs can be assessed as described above. Candidate vaccine immunogens can be evaluated using in vivo malaria infection models. Examples of these models take advantage of a transgenic rodent malaria parasite (*P. berghei*, Pb) in which the endogenous PbCSP or PbMSP1-19 are replaced with PfCSP or PfMSP1-19 to evaluate pre-erythrocytic and blood stage vaccine candidates, respectively. Miller et al., PLoS One. 2013; 8(4):e60820 (doi: 10.1371/journal.pone.0060820); de Koning-Ward et al., J Exp Med. 2003; 198(6):869-75. In addition, these parasites also constitutively express luciferase. In vivo bioluminescent imaging allows for an efficient, sensitive and non-invasive alternative for quantitative analysis of liver stage parasite infection.

(x) Exemplary Embodiments

1. A mutant N-terminus domain (NTD) of a circumsporozoite protein (CSP) including a KKNSR (SEQ ID NO: 1) to SSNSS (SEQ ID NO: 2) or SSNSA (SEQ ID NO: 4) mutation directly upstream of a SLGENDD (SEQ ID NO: 3) cleavage site.
2. The mutant NTD of embodiment 1, including removal of a cysteine within the N-terminus of the CSP.
3. The mutant NTD of embodiment 2, wherein the cysteine is residue 5 of the wild-type CSP protein lacking the signal peptide.
4. The mutant NTD of embodiment 2 or 3, wherein the removal of the cysteine includes replacing the cysteine with serine.
5. A truncated circumsporozoite protein (CSP) having the sequence as set forth for DeltaN-CSP (SEQ ID NO: 77), DeltaN-CSP-5/3 (SEQ ID NO: 78), or DeltaN-CSP-19/3.
6. The mutant NTD or truncated CSP of any of embodiments 1-5, expressed as a fusion protein with a secondary malaria vaccine epitope.
7. The mutant NTD or truncated CSP of embodiment 6, wherein the secondary malaria vaccine epitope is selected from RTS,S; NR2C, R2C, the junctional epitope, the minor epitope, or a junctional epitope linked to the minor epitope.
8. The mutant NTD of embodiment 7, wherein the fusion protein includes C5S-SAmut, C5S-SAmut-23/4, C5S-SAmut-19/3, or C5S-SAmut-5/3.
9. The mutant NTD or truncated CSP of embodiment 5 or 8, lacking the His tag and/or Avi tag.
10. The mutant NTD or truncated CSP of any of embodiments 6-9, wherein the fusion protein further includes a multimerization domain.
11. The mutant NTD or truncated CSP of embodiment 10, wherein the multimerization domain includes a C4b multimerization domain or a ferritin multimerization domain.
12. The mutant NTD or truncated CSP of any of embodiments 6-11, wherein the fusion protein further includes a linker.
13. The mutant NTD or truncated CSP of embodiment 12, wherein the linker includes a Gly-Ser linker.
14. The mutant NTD or truncated CSP of any of embodiments 6-13, wherein the fusion protein further includes a self-cleaving peptide.
15. The mutant NTD or truncated CSP of embodiment 14, wherein the self-cleaving peptide includes T2A, P2A, E2A, or F2A.
16. A mutant circumsporozoite protein (CSP) comprising the sequence T2A, P2A, E2A, or (SEQ ID No: 8) or SLSSN-SASLGENDD (SEQ ID NO: 76) in place of the wild-type SLKKNSRSLGENDD (SEQ ID NO: 7) sequence
17. A mutant circumsporozoite protein (CSP) comprising the sequence QEYQCYGSSSNTRVLNELNTDNAGTNLY-NELEMNYYGKQENWYSLSSNSSSLGENDD (SEQ ID NO: 9) or QEYQSYGSSSNTRVLNELNTDNAGTN-LYNELEMNYYGKQENWYSLSSNSSSLGENDD (SEQ ID NO: 11) in place of the wild-type QEYQCYGSSSNTRVLNELNTDNAGTNLYNELEM-NYYGKQENWYSLKKNSRSLGENDD (SEQ ID NO: 10) sequence.
18. Use of a mutant NTD or truncated CSP of any of embodiments 1-17 as an anti-malarial vaccine.
19. A method of stimulating an anti-malarial immune response in a subject including administering a therapeutically effective amount of a mutant NTD or truncated CSP of any of embodiments 1-17 to the subject thereby stimulating the anti-malarial immune response in the subject.
20. A method of producing a mutant N-terminus domain (NTD) of a circumsporozoite protein (CSP) including introducing a gene encoding the mutant NTD into mammalian cells under conditions to result in expression of the mutant NTD wherein the mutant NTD includes a KKNSR (SEQ ID NO: 1) to SSNSS (SEQ ID NO: 2) or SSNSA (SEQ ID NO: 4) mutation directly upstream of a SLGENDD (SEQ ID NO: 3) cleavage site.
21. The method of embodiment 20, wherein the gene encodes a serine rather than a cysteine within the mutant NTD.
22. The method of embodiment 21, wherein the encoded serine is expressed at residue 5 of the wild-type CSP protein lacking the signal peptide.
23. The method of any of embodiments 20-22, wherein the gene encodes the NTD as part of a fusion protein with a secondary malaria vaccine epitope.
24. The method of embodiment 23, wherein the secondary malaria vaccine epitope is selected from RTS,S; NR2C, R2C, the junctional epitope, the minor epitope, or a junctional epitope linked to the minor epitope.
25. The method of embodiment 20, wherein the fusion protein includes C5S-SAmut, C5S-SAmut-23/4, C5S-SAmut-19/3, or C5S-SAmut-5/3.
26. The method of any of embodiments 23-25, wherein the fusion protein further includes a multimerization domain.
27. The method of embodiment 26, wherein the multimerization domain includes a C4b multimerization domain or a ferritin multimerization domain.
28. The method of any of embodiments 23-27, wherein the fusion protein further includes a linker.
29. The method of embodiment 28, wherein the linker includes a Gly-Ser linker.
30. The method of any of embodiments 23-29, wherein the fusion protein further includes a self-cleaving peptide.
31. The method of embodiment 30, wherein the self-cleaving peptide includes T2A, P2A, E2A, or F2A.
32. The method of any of embodiments 20-31, wherein the producing is ex vivo or in vivo.

33. The method of any of embodiments 20-32, wherein the mammalian cells are in suspension in a serum free media.
34. The method of any of embodiments 20-33, wherein the introducing the gene includes transfecting the mammalian cells with plasmid DNA.
35. The method of any of embodiments 20-34, wherein the introducing the gene includes transfecting the mammalian cells with a viral vector.
36. The method of any of embodiments 20-35, wherein the mammalian cells are HEK cells.
37. The method of any of embodiments 20-36, further including purifying the produced mutant NTD.
38. The method of embodiment 37, wherein the purifying includes size exclusion chromatography.

(xi) Closing Paragraphs. Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wis.) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (nonpolar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PEN- ALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH$_2$PO$_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the increased expression relative to WT CSP proteins as described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A mutant N-terminus domain (NTD) of a circumsporozoite protein (CSP) comprising
   i) a KKNSR (SEQ ID NO: 1) to SSNSS (SEQ ID NO: 2) mutation directly upstream of a SLGENDD (SEQ ID NO: 3) cleavage site of a wild-type *Plasmodium falciparum* CSP; or
   ii) a KKNSR (SEQ ID NO: 1) to SSNSA (SEQ ID NO: 4) mutation directly upstream of a SLGENDD (SEQ ID NO: 3) cleavage site of a wild-type *Plasmodium falciparum* CSP;
wherein the wild-type *Plasmodium falciparum* CSP comprises a sequence as set forth in SEQ ID NOs: 7, 10, or 19.

2. The mutant NTD of claim 1, further comprising a cysteine deletion.

3. The mutant NTD of claim 2, wherein the cysteine is residue 5 of the wild-type *Plasmodium falciparum* CSP protein.

4. The mutant NTD of claim 1, further comprising a cysteine to serine substitution.

5. The mutant NTD of claim 1, expressed as a fusion protein with a secondary malaria vaccine epitope.

6. The mutant NTD of claim 5, wherein the secondary malaria vaccine epitope is selected from RTS,S; NR2C, R2C, the junctional epitope, the minor epitope, or a junctional epitope linked to the minor epitope.

7. The mutant NTD of claim 5, wherein the fusion protein comprises the sequence as set forth in SEQ ID NO: 12 (FL C5S-SAmut), SEQ ID NO: 13 (C5S-SAmut-23/4), SEQ ID NO: 14 (C5S-SAmut-19/3), or SEQ ID NO: 15 (C5S-SAmut-5/3).

8. A circumsporozoite protein (CSP) comprising
   i) a KKNSR (SEQ ID NO: 1) to SSNSS (SEQ ID NO: 2) mutation directly upstream of a SLGENDD (SEQ ID NO: 3) cleavage site within the N-terminal domain of a wild-type *Plasmodium falciparum* CSP; or
   ii) a KKNSR (SEQ ID NO: 1) to SSNSA (SEQ ID NO: 4) mutation directly upstream of a SLGENDD (SEQ ID NO: 3) cleavage site within the N-terminal domain of a wild-type *Plasmodium falciparum* CSP;

wherein the wild-type *Plasmodium falciparum* CSP comprises a sequence as set forth in SEQ ID NOs: 7, 10, or 19.

9. The CSP of claim 8, further comprising a cysteine deletion within the N-terminus of the CSP.

10. The CSP of claim 9, wherein the cysteine is residue 5 of the wild-type *Plasmodium falciparum* CSP protein.

11. The CSP of claim 8, further comprising a cysteine to serine substitution within the N-terminus of the CSP.

12. The CSP of claim 8, having the sequence SLSSNSSSLGENDD (SEQ ID NO: 8) or SLSSNSASLGENDD (SEQ ID NO: 76) in place of the wild-type SLKKNSRSLGENDD (SEQ ID NO: 7) sequence.

13. The CSP of claim 8, having the sequence QEYQCYGSSSNTRVLNELNYDNAGTNLYNELEMNYYGKQENWYSLSSNSSSLGENDD (SEQ ID NO: 9) or QEYQSYGSSSNTRVLNELNYDNAGTNLYNELEMNYYGKQENWYSLSSNSASLGENDD (SEQ ID NO: 11) in place of the wild-type QEYQCYGSSSNTRVLNELNYDNAGTNLYNELEMNYYGKQENWYSLKKNSRSLGEN DD (SEQ ID NO: 10) sequence.

14. A method of stimulating an anti-malarial immune response in a subject comprising administering a therapeutically effective amount of a circumsporozoite protein (CSP) to the subject, wherein the CSP protein comprises
   ii) a KKNSR (SEQ ID NO: 1) to SSNSS (SEQ ID NO: 2) mutation directly upstream of a SLGENDD (SEQ ID NO: 3) cleavage site in the N-terminal domain (NTD) of a wild-type *Plasmodium falciparum* CSP; or
   iii) a KKNSR (SEQ ID NO: 1) to SSNSA (SEQ ID NO: 4) mutation directly upstream of a SLGENDD (SEQ ID NO: 3) cleavage site in the NTD of a wild-type *Plasmodium falciparum* CSP;

wherein the wild-type *Plasmodium falciparum* CSP comprises a sequence as set forth in SEQ ID NOs: 7, 10, or 19, thereby stimulating the anti-malarial immune response in the subject.

15. The method of claim 14, wherein the CSP protein comprises a cysteine deletion within the N-terminus of the wild-type *Plasmodium falciparum* CSP.

16. The method of claim 15, wherein the deleted cysteine was at residue 5 of the wild-type *Plasmodium falciparum* CSP protein.

17. The method of claim 14, wherein the CSP protein comprises a cysteine to serine substitution.

18. The method of claim 14, wherein the CSP comprises a malaria vaccine epitope.

19. The method of claim 18, wherein the malaria vaccine epitope is selected from RTS,S; NR2C, R2C, the junctional epitope, the minor epitope, or a junctional epitope linked to the minor epitope.

20. The method of claim 14, wherein the CSP comprises the sequence as set forth in SEQ ID NO: 12, SEQ ID NO: 13, SEQ ID NO: 14, or SEQ ID NO: 15.

* * * * *

SEQUENCE LISTING

```
<160> NUMBER OF SEQ ID NOS: 79

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Lys Lys Asn Ser Arg
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic construct

<400> SEQUENCE: 2

Ser Ser Asn Ser Ser
1               5

<210> SEQ ID NO 3
<211> LENGTH: 7
<212> TYPE: PRT
<213> ORGANISM: Artificial Sequence
<220> FEATURE:
<223> OTHER INFORMATION: cleavage site

<400> SEQUENCE: 3

Ser Leu Gly Glu Asn Asp Asp
1               5
```

-continued

<210> SEQ ID NO 4
<211> LENGTH: 5
<212> TYPE: PRT
<213> ORGANISM: Artificial Sequence
<220> FEATURE:
<223> OTHER INFORMATION: synthetic construct

<400> SEQUENCE: 4

Ser Ser Asn Ser Ala
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(4)
<223> OTHER INFORMATION: Xaa can be any amino acid residue

<400> SEQUENCE: 5

Ser Ser Xaa Xaa Ser
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(4)
<223> OTHER INFORMATION: Xaa can be any amino acid residue

<400> SEQUENCE: 6

Ser Ser Xaa Xaa Ala
1               5

<210> SEQ ID NO 7
<211> LENGTH: 14
<212> TYPE: PRT
<213> ORGANISM: Artificial Sequence
<220> FEATURE:
<223> OTHER INFORMATION: circumsporozoite protein (CSP)

<400> SEQUENCE: 7

Ser Leu Lys Lys Asn Ser Arg Ser Leu Gly Glu Asn Asp Asp
1               5                   10

<210> SEQ ID NO 8
<211> LENGTH: 14
<212> TYPE: PRT
<213> ORGANISM: Artificial Sequence
<220> FEATURE:
<223> OTHER INFORMATION: mutant circumsporozoite protein (CSP)

<400> SEQUENCE: 8

Ser Leu Ser Ser Asn Ser Ser Ser Leu Gly Glu Asn Asp Asp
1               5                   10

<210> SEQ ID NO 9
<211> LENGTH: 57
<212> TYPE: PRT
<213> ORGANISM: Artificial Sequence
<220> FEATURE:
<223> OTHER INFORMATION: circumsporozoite protein (CSP)

<400> SEQUENCE: 9

Gln Glu Tyr Gln Cys Tyr Gly Ser Ser Asn Thr Arg Val Leu Asn
1               5                   10                  15

Glu Leu Asn Tyr Asp Asn Ala Gly Thr Asn Leu Tyr Asn Glu Leu Glu
            20                  25                  30

Met Asn Tyr Tyr Gly Lys Gln Glu Asn Trp Tyr Ser Leu Ser Ser Asn
        35                  40                  45

Ser Ser Ser Leu Gly Glu Asn Asp Asp
    50                  55

<210> SEQ ID NO 10
<211> LENGTH: 57
<212> TYPE: PRT
<213> ORGANISM: Artificial Sequence
<220> FEATURE:
<223> OTHER INFORMATION: circumsporozoite protein (CSP)

<400> SEQUENCE: 10

Gln Glu Tyr Gln Cys Tyr Gly Ser Ser Asn Thr Arg Val Leu Asn
1               5                   10                  15

Glu Leu Asn Tyr Asp Asn Ala Gly Thr Asn Leu Tyr Asn Glu Leu Glu
            20                  25                  30

Met Asn Tyr Tyr Gly Lys Gln Glu Asn Trp Tyr Ser Leu Lys Lys Asn
        35                  40                  45

Ser Arg Ser Leu Gly Glu Asn Asp Asp
    50                  55

<210> SEQ ID NO 11
<211> LENGTH: 57
<212> TYPE: PRT
<213> ORGANISM: Artificial Sequence
<220> FEATURE:
<223> OTHER INFORMATION: C5S-SAmut

<400> SEQUENCE: 11

Gln Glu Tyr Gln Ser Tyr Gly Ser Ser Ser Asn Thr Arg Val Leu Asn
1               5                   10                  15

Glu Leu Asn Tyr Asp Asn Ala Gly Thr Asn Leu Tyr Asn Glu Leu Glu
            20                  25                  30

Met Asn Tyr Tyr Gly Lys Gln Glu Asn Trp Tyr Ser Leu Ser Ser Asn
        35                  40                  45

Ser Ala Ser Leu Gly Glu Asn Asp Asp
    50                  55

<210> SEQ ID NO 12
<211> LENGTH: 387
<212> TYPE: PRT
<213> ORGANISM: Artificial Sequence
<220> FEATURE:
<223> OTHER INFORMATION: FL C5S-Samut

<400> SEQUENCE: 12

Gln Glu Tyr Gln Ser Tyr Gly Ser Ser Ser Asn Thr Arg Val Leu Asn
1               5                   10                  15

Glu Leu Asn Tyr Asp Asn Ala Gly Thr Asn Leu Tyr Asn Glu Leu Glu
            20                  25                  30

Met Asn Tyr Tyr Gly Lys Gln Glu Asn Trp Tyr Ser Leu Ser Ser Asn
        35                  40                  45

Ser Ala Ser Leu Gly Glu Asn Asp Asp Gly Asn Asn Glu Asp Asn Glu
    50                  55                  60
Lys Leu Arg Lys Pro Lys His Lys Lys Leu Lys Gln Pro Ala Asp Gly
65                  70                  75                  80
Asn Pro Asp Pro Asn Ala Asn Pro Asn Val Asp Pro Asn Ala Asn Pro
                85                  90                  95
Asn Val Asp Pro Asn Ala Asn Pro Asn Val Asp Pro Asn Ala Asn Pro
            100                 105                 110
Asn Ala Asn Pro Asn Ala Asn Pro Asn Ala Asn Pro Asn Ala Asn Pro
        115                 120                 125
Asn Ala Asn Pro Asn Ala Asn Pro Asn Ala Asn Pro Asn Ala Asn Pro
    130                 135                 140
Asn Ala Asn Pro Asn Ala Asn Pro Asn Ala Asn Pro Asn Ala Asn Pro
145                 150                 155                 160
Asn Ala Asn Pro Asn Ala Asn Pro Asn Ala Asn Pro Asn Ala Asn Pro
                165                 170                 175
Asn Val Asp Pro Asn Ala Asn Pro Asn Ala Asn Pro Asn Ala Asn Pro
            180                 185                 190
Asn Ala Asn Pro Asn Ala Asn Pro Asn Ala Asn Pro Asn Ala Asn Pro
        195                 200                 205
Asn Ala Asn Pro Asn Ala Asn Pro Asn Ala Asn Pro Asn Ala Asn Pro
    210                 215                 220
Asn Ala Asn Pro Asn Ala Asn Pro Asn Ala Asn Pro Asn Ala Asn Pro
225                 230                 235                 240
Asn Ala Asn Pro Asn Ala Asn Pro Asn Ala Asn Pro Asn Lys Asn Asn
                245                 250                 255
Gln Gly Asn Gly Gln Gly His Asn Met Pro Asn Asp Pro Asn Arg Asn
            260                 265                 270
Val Asp Glu Asn Ala Asn Ala Asn Ser Ala Val Lys Asn Asn Asn Asn
            275                 280                 285
Glu Glu Pro Ser Asp Lys His Ile Lys Glu Tyr Leu Asn Lys Ile Gln
        290                 295                 300
Asn Ser Leu Ser Thr Glu Trp Ser Pro Cys Ser Val Thr Cys Gly Asn
305                 310                 315                 320
Gly Ile Gln Val Arg Ile Lys Pro Gly Ser Ala Asn Lys Pro Lys Asp
                325                 330                 335
Glu Leu Asp Tyr Ala Asn Asp Ile Glu Lys Lys Ile Cys Lys Met Glu
            340                 345                 350
Lys Cys Ser Gly Ser Gly Leu Asn Asp Ile Phe Glu Ala Gln Lys Ile
        355                 360                 365
Glu Trp His Glu Leu Glu Val Leu Phe Gln Gly Pro Gly His His His
    370                 375                 380
His His His
385

<210> SEQ ID NO 13
<211> LENGTH: 327
<212> TYPE: PRT
<213> ORGANISM: Artificial Sequence
<220> FEATURE:
<223> OTHER INFORMATION: C5S-SAmut-23/4

<400> SEQUENCE: 13

Gln Glu Tyr Gln Ser Tyr Gly Ser Ser Ser Asn Thr Arg Val Leu Asn
1               5                   10                  15

-continued

Glu Leu Asn Tyr Asp Asn Ala Gly Thr Asn Leu Tyr Asn Glu Leu Glu
                 20                  25                  30

Met Asn Tyr Tyr Gly Lys Gln Glu Asn Trp Tyr Ser Leu Ser Ser Asn
             35                  40                  45

Ser Ala Ser Leu Gly Glu Asn Asp Gly Asn Asn Glu Asp Asn Glu
 50                  55                  60

Lys Leu Arg Lys Pro Lys His Lys Lys Leu Lys Gln Pro Ala Asp Gly
 65                  70                  75                  80

Asn Pro Asp Pro Asn Ala Asn Pro Asn Val Asp Pro Asn Ala Asn Pro
                 85                  90                  95

Asn Val Asp Pro Asn Ala Asn Pro Asn Val Asp Pro Asn Ala Asn Pro
             100                 105                 110

Asn Ala Asn Pro Asn Ala Asn Pro Asn Ala Asn Pro Asn Ala Asn Pro
             115                 120                 125

Asn Ala Asn Pro Asn Ala Asn Pro Asn Ala Asn Pro Asn Ala Asn Pro
             130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
             165                 170                 175

Asn Val Asp Pro Asn Ala Asn Pro Asn Ala Asn Pro Asn Ala Asn Pro
             180                 185                 190

Asn Lys Asn Asn Gln Gly Asn Gly Gln Gly His Asn Met Pro Asn Asp
             195                 200                 205

Pro Asn Arg Asn Val Asp Glu Asn Ala Asn Ala Ser Ala Val Lys
             210                 215                 220

Asn Asn Asn Asn Glu Glu Pro Ser Asp Lys His Ile Lys Glu Tyr Leu
225                 230                 235                 240

Asn Lys Ile Gln Asn Ser Leu Ser Thr Glu Trp Ser Pro Cys Ser Val
             245                 250                 255

Thr Cys Gly Asn Gly Ile Gln Val Arg Ile Lys Pro Gly Ser Ala Asn
             260                 265                 270

Lys Pro Lys Asp Glu Leu Asp Tyr Ala Asn Asp Ile Glu Lys Lys Ile
             275                 280                 285

Cys Lys Met Glu Lys Cys Ser Gly Ser Gly Leu Asn Asp Ile Phe Glu
             290                 295                 300

Ala Gln Lys Ile Glu Trp His Glu Leu Glu Val Leu Phe Gln Gly Pro
305                 310                 315                 320

Gly His His His His His His
            325

<210> SEQ ID NO 14
<211> LENGTH: 307
<212> TYPE: PRT
<213> ORGANISM: Artificial Sequence
<220> FEATURE:
<223> OTHER INFORMATION: C5S-SAmut-19/3

<400> SEQUENCE: 14

Gln Glu Tyr Gln Ser Tyr Gly Ser Ser Ser Asn Thr Arg Val Leu Asn
1               5                   10                  15

Glu Leu Asn Tyr Asp Asn Ala Gly Thr Asn Leu Tyr Asn Glu Leu Glu
                 20                  25                  30

Met Asn Tyr Tyr Gly Lys Gln Glu Asn Trp Tyr Ser Leu Ser Ser Asn
             35                  40                  45

Ser Ala Ser Leu Gly Glu Asn Asp Asp Gly Asn Asn Glu Asp Asn Glu
        50                  55                  60

Lys Leu Arg Lys Pro Lys His Lys Lys Leu Lys Gln Pro Ala Asp Gly
 65                  70                  75                  80

Asn Pro Asp Pro Asn Ala Asn Pro Asn Val Asp Pro Asn Ala Asn Pro
                85                  90                  95

Asn Val Asp Pro Asn Ala Asn Pro Asn Val Asp Pro Asn Ala Asn Pro
            100                 105                 110

Asn Ala Asn Pro Asn Ala Asn Pro Asn Ala Asn Pro Asn Ala Asn Pro
            115                 120                 125

Asn Ala Asn Pro Asn Ala Asn Pro Asn Ala Asn Pro Asn Ala Asn Pro
            130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Lys Asn Asn
                165                 170                 175

Gln Gly Asn Gly Gln Gly His Asn Met Pro Asn Asp Pro Asn Arg Asn
            180                 185                 190

Val Asp Glu Asn Ala Asn Ala Asn Ser Ala Val Lys Asn Asn Asn Asn
            195                 200                 205

Glu Glu Pro Ser Asp Lys His Ile Lys Glu Tyr Leu Asn Lys Ile Gln
    210                 215                 220

Asn Ser Leu Ser Thr Glu Trp Ser Pro Cys Ser Val Thr Cys Gly Asn
225                 230                 235                 240

Gly Ile Gln Val Arg Ile Lys Pro Gly Ser Ala Asn Lys Pro Lys Asp
                245                 250                 255

Glu Leu Asp Tyr Ala Asn Asp Ile Glu Lys Lys Ile Cys Lys Met Glu
            260                 265                 270

Lys Cys Ser Gly Ser Gly Leu Asn Asp Ile Phe Glu Ala Gln Lys Ile
            275                 280                 285

Glu Trp His Glu Leu Glu Val Leu Phe Gln Gly Pro Gly His His His
    290                 295                 300

His His His
305

<210> SEQ ID NO 15
<211> LENGTH: 251
<212> TYPE: PRT
<213> ORGANISM: Artificial Sequence
<220> FEATURE:
<223> OTHER INFORMATION: C5S-SAmut-5/3

<400> SEQUENCE: 15

Gln Glu Tyr Gln Ser Tyr Gly Ser Ser Ser Asn Thr Arg Val Leu Asn
1               5                   10                  15

Glu Leu Asn Tyr Asp Asn Ala Gly Thr Asn Leu Tyr Asn Glu Leu Glu
            20                  25                  30

Met Asn Tyr Tyr Gly Lys Gln Glu Asn Trp Tyr Ser Leu Ser Ser Asn
        35                  40                  45

Ser Ala Ser Leu Gly Glu Asn Asp Asp Gly Asn Asn Glu Asp Asn Glu
    50                  55                  60

Lys Leu Arg Lys Pro Lys His Lys Lys Leu Lys Gln Pro Ala Asp Gly
65                  70                  75                  80

Asn Pro Asp Pro Asn Ala Asn Pro Asn Val Asp Pro Asn Ala Asn Pro
                85                  90                  95

-continued

```
Asn Val Asp Pro Asn Ala Asn Pro Asn Val Asp Pro Asn Ala Asn Pro
            100                 105                 110

Asn Ala Asn Pro Asn Lys Asn Gln Gly Asn Gly Gln Gly His Asn
        115                 120                 125

Met Pro Asn Asp Pro Asn Arg Asn Val Asp Glu Asn Ala Asn Ala Asn
130                 135                 140

Ser Ala Val Lys Asn Asn Asn Glu Glu Pro Ser Asp Lys His Ile
145                 150                 155                 160

Lys Glu Tyr Leu Asn Lys Ile Gln Asn Ser Leu Ser Thr Glu Trp Ser
                165                 170                 175

Pro Cys Ser Val Thr Cys Gly Asn Gly Ile Gln Val Arg Ile Lys Pro
            180                 185                 190

Gly Ser Ala Asn Lys Pro Lys Asp Glu Leu Asp Tyr Ala Asn Asp Ile
        195                 200                 205

Glu Lys Lys Ile Cys Lys Met Glu Lys Cys Ser Gly Ser Gly Leu Asn
    210                 215                 220

Asp Ile Phe Glu Ala Gln Lys Ile Glu Trp His Glu Leu Glu Val Leu
225                 230                 235                 240

Phe Gln Gly Pro Gly His His His His His His
                245                 250

<210> SEQ ID NO 16
<211> LENGTH: 15
<212> TYPE: PRT
<213> ORGANISM: Artificial Sequence
<220> FEATURE:
<223> OTHER INFORMATION: junctional epitope

<400> SEQUENCE: 16

Asn Pro Asp Pro Asn Ala Asn Pro Asn Val Asp Pro Asn Ala Asn
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: minor epitope

<400> SEQUENCE: 17

Asn Val Asp Pro Asn Ala Asn Pro Asn Val Asp Pro Asn
1               5                   10

<210> SEQ ID NO 18
<211> LENGTH: 29
<212> TYPE: PRT
<213> ORGANISM: Artificial Sequence
<220> FEATURE:
<223> OTHER INFORMATION: junctional epitope linked to minor epitope

<400> SEQUENCE: 18

Asn Pro Asp Pro Asn Ala Asn Pro Asn Val Asp Pro Asn Ala Asn Pro
1               5                   10                  15

Asn Val Asp Pro Asn Ala Asn Pro Asn Val Asp Pro Asn
            20                  25

<210> SEQ ID NO 19
<211> LENGTH: 424
<212> TYPE: PRT
<213> ORGANISM: Plasmodium falciparum
```

<400> SEQUENCE: 19

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Ile Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
                100                 105                 110

Leu Lys Gln Pro Gly Asp Gly Asn Pro Asp Pro Asn Ala Asn Pro Asn
            115                 120                 125

Val Asp Pro Asn Ala Asn Pro Asn Val Asp Pro Asn Ala Asn Pro Asn
            130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
                180                 185                 190

Ala Asn Pro Asn Ala Asn Pro Asn Ala Asn Pro Asn Ala Asn Pro Asn
                195                 200                 205

Ala Asn Pro Asn Ala Asn Pro Asn Ala Asn Pro Asn Ala Asn Pro Asn
                210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Ala Asn Pro Asn
                260                 265                 270

Ala Asn Pro Asn Ala Asn Pro Asn Ala Asn Pro Asn Ala Asn Pro Asn
                275                 280                 285

Ala Asn Pro Asn Ala Asn Pro Asn Ala Asn Pro Asn Lys Asn Asn Gln
                290                 295                 300

Gly Asn Gly Gln Gly His Asn Met Pro Asn Asp Pro Asn Arg Asn Val
305                 310                 315                 320

Asp Glu Asn Ala Asn Ala Asn Ala Val Lys Asn Asn Asn Asn Asn Glu
                325                 330                 335

Glu Pro Ser Asp Lys His Ile Glu Gln Tyr Leu Lys Lys Ile Gln Asn
            340                 345                 350

Ser Leu Ser Thr Glu Trp Ser Pro Cys Ser Val Thr Cys Gly Asn Gly
            355                 360                 365

Ile Gln Val Arg Ile Lys Pro Gly Ser Ala Asn Lys Pro Lys Asp Glu
        370                 375                 380

Leu Asp Tyr Glu Asn Asp Ile Glu Lys Lys Ile Cys Lys Met Glu Lys
385                 390                 395                 400

Cys Ser Ser Val Phe Asn Val Val Asn Ser Ser Ile Gly Leu Ile Met
                405                 410                 415
```

Val Leu Ser Phe Leu Phe Leu Asn
                420

<210> SEQ ID NO 20
<211> LENGTH: 368
<212> TYPE: PRT
<213> ORGANISM: Plasmodium vivax

<400> SEQUENCE: 20

Val Asp Leu Ser Lys Ala Ile Asn Leu Asn Gly Val Asn Phe Asn Asn
1               5                   10                  15

Val Asp Ala Ser Ser Leu Gly Ala Ala His Val Gly Gln Ser Ala Ser
            20                  25                  30

Arg Gly Arg Gly Leu Gly Glu Asn Pro Asp Asp Glu Glu Gly Asp Ala
        35                  40                  45

Lys Lys Lys Lys Asp Gly Lys Lys Ala Glu Pro Lys Asn Pro Arg Glu
50                  55                  60

Asn Lys Leu Lys Gln Pro Gly Asp Arg Ala Asp Gly Gln Ala Ala Gly
65                  70                  75                  80

Asn Gly Ala Gly Gly Gln Pro Ala Gly Asp Arg Ala Ala Gly Gln Pro
            85                  90                  95

Ala Gly Asp Gly Ala Ala Gly Gln Pro Ala Gly Asp Gly Ala Asp Gly
            100                 105                 110

Gln Ala Ala Gly Asn Gly Ala Gly Gly Gln Pro Ala Gly Asp Arg Ala
            115                 120                 125

Ala Gly Gln Pro Ala Gly Asp Gly Ala Ala Gly Gln Pro Ala Gly Asp
        130                 135                 140

Arg Ala Asp Gly Gln Pro Ala Gly Asp Arg Ala Ala Gly Gln Pro Ala
145                 150                 155                 160

Gly Asp Arg Ala Asp Gly Gln Pro Ala Gly Asp Arg Ala Ala Gly Gln
                165                 170                 175

Ala Ala Gly Asn Gly Ala Gly Gly Gln Ala Ala Gly Asn Gly Ala Gly
            180                 185                 190

Gly Gln Pro Ala Gly Asp Arg Thr Ala Gly Gln Pro Ala Gly Asn Arg
        195                 200                 205

Thr Thr Gly Gln Ala Ala Gly Asn Gly Ala Gly Gln Ala Ala Gly
    210                 215                 220

Lys Gly Ala Gly Gly Gln Ala Ala Arg Asn Gly Ala Gly Gly Gln Ala
225                 230                 235                 240

Ala Gly Asn Gly Ala Gly Gly Pro Ala Ala Gly Gly Asn Ala Ala Asn
                245                 250                 255

Lys Lys Ala Glu Asp Ala Gly Gly Asn Ala Gly Gly Asn Ala Gly Gly
            260                 265                 270

Gln Gly Gln Asn Asn Glu Gly Ala Asn Ala Pro Asn Glu Lys Ser Val
        275                 280                 285

Lys Glu Tyr Leu Asp Lys Val Arg Ala Thr Val Gly Thr Glu Trp Thr
290                 295                 300

Pro Cys Ser Val Thr Cys Gly Val Gly Val Arg Val Arg Arg Arg Val
305                 310                 315                 320

Asn Ala Ala Asn Lys Lys Pro Glu Asp Leu Thr Leu Asn Asp Leu Glu
                325                 330                 335

Thr Asp Val Cys Thr Met Asp Lys Cys Ala Gly Ile Phe Asn Val Val
            340                 345                 350

Ser Asn Ser Leu Gly Leu Val Ile Leu Leu Cys Leu Ala Leu Phe Asn

<210> SEQ ID NO 21
<211> LENGTH: 406
<212> TYPE: PRT
<213> ORGANISM: Plasmodium knowlesi

<400> SEQUENCE: 21

```
Met Lys Asn Phe Ile Leu Leu Ala Val Ser Ser Ile Leu Leu Val Asp
1               5                   10                  15

Leu Leu Pro Thr His Phe Glu His Asn Val Asp Leu Ser Arg Ala Ile
            20                  25                  30

Asn Val Asn Gly Val Ser Phe Asn Val Asp Thr Ser Ser Leu Gly
        35                  40                  45

Ala Ala Gln Val Arg Gln Ser Ala Ser Arg Gly Arg Gly Leu Gly Glu
    50                  55                  60

Lys Pro Lys Glu Gly Asp Asp Lys Glu Lys Lys Glu Lys Glu Lys
65              70                  75                  80

Glu Glu Glu Pro Lys Asn Leu Asn Glu Asn Lys Pro Lys Gln Pro Asn
                85                  90                  95

Ala Glu Gly Asp Gly Ala Lys Pro Lys Gln Pro Asn Ala Glu Gly Asp
            100                 105                 110

Gly Ala Lys Leu Lys Gln Pro Asn Ala Glu Gly Asp Gly Ala Lys Leu
        115                 120                 125

Lys Gln Pro Asn Ala Glu Gly Asp Gly Asn Ala Arg Gln Pro Asn
130                 135                 140

Ala Glu Gly Asp Gly Gly Asn Ala Arg Gln Pro Asn Ala Glu Gly Asp
145                 150                 155                 160

Gly Gly Asn Ala Arg Gln Pro Asn Ala Glu Gly Asp Gly Gly Asn Ala
            165                 170                 175

Arg Gln Pro Asn Ala Glu Gly Asp Gly Gly Asn Ala Arg Gln Pro Asn
        180                 185                 190

Ala Glu Gly Asp Gly Gly Asn Ala Arg Gln Pro Asn Ala Glu Gly Asp
    195                 200                 205

Gly Gly Asn Ala Arg Gln Pro Asn Ala Glu Gly Asp Gly Gly Asn Ala
210                 215                 220

Arg Gln Pro Asn Ala Glu Gly Asp Gly Gly Asn Ala Arg Gln Pro Asn
225                 230                 235                 240

Ala Glu Gly Asp Gly Gly Asn Ala Arg Gln Pro Asn Ala Glu Gly Asp
            245                 250                 255

Gly Gly Asn Ala Arg Gln Pro Asn Ala Glu Gly Asp Gly Ala Asn Ala
        260                 265                 270

Arg Gln Pro Asn Ala Glu Gly Asp Gly Ala Asn Ala Arg Gln Pro Gln
    275                 280                 285

Ala Glu Gly Gly Gly Gly Asn Ala Arg Gln Gly Gly Asn Glu Gly Asn
    290                 295                 300

Lys Gln Ala Gly Lys Gly Gln Gly Gln Asn Asn Gln Gly Ala Asn Ala
305                 310                 315                 320

Pro Asn Glu Lys Val Val Asn Asp Tyr Leu Gln Lys Ile Arg Ser Ser
                325                 330                 335

Val Thr Thr Glu Trp Thr Pro Cys Ser Val Thr Cys Gly Asn Gly Val
            340                 345                 350

Arg Ile Arg Arg Ala His Ala Asp Lys Lys Lys Ala Glu Asp Leu
        355                 360                 365
```

```
Thr Met Asp Asp Leu Glu Val Glu Ala Cys Val Met Asp Lys Cys Ala
    370                 375                 380

Gly Ile Phe Asn Val Val Ser Asn Ser Leu Gly Leu Val Ile Leu Leu
385                 390                 395                 400

Val Leu Ala Leu Phe Asn
                405

<210> SEQ ID NO 22
<211> LENGTH: 429
<212> TYPE: PRT
<213> ORGANISM: Plasmodium malariae

<400> SEQUENCE: 22

Met Lys Lys Leu Ser Val Leu Ala Ile Ser Ser Phe Leu Ile Val Asp
1               5                   10                  15

Phe Leu Phe Pro Gly Tyr His His Asn Ser Asn Ser Thr Lys Ser Arg
                20                  25                  30

Asn Leu Ser Glu Leu Cys Tyr Asn Asn Val Asp Thr Lys Leu Phe Asn
            35                  40                  45

Glu Leu Glu Val Arg Tyr Ser Thr Asn Gln Asp His Phe Tyr Asn Tyr
    50                  55                  60

Asn Lys Thr Ile Arg Leu Leu Asn Glu Asn Asn Glu Lys Asp Gly
65                  70                  75                  80

Asn Val Thr Asn Glu Arg Lys Lys Lys Pro Thr Lys Ala Val Glu Asn
                85                  90                  95

Lys Leu Lys Gln Pro Pro Gly Asp Asp Gly Ala Gly Asn Asp Ala
            100                 105                 110

Gly Asn Asp Ala Gly Asn Asp Ala Gly Asn Ala Ala Gly Asn Ala Ala
        115                 120                 125

Gly Asn Ala Ala Gly Asn Ala Ala Gly Asn Ala Ala Gly Asn Ala Ala
    130                 135                 140

Gly Asn Ala Ala Gly Asn Ala Ala Gly Asn Ala Ala Gly Asn Ala Ala
145                 150                 155                 160

Gly Asn Asp Ala Gly Asn Ala Ala Gly Asn Asp Ala Gly Asn Ala Ala
                165                 170                 175

Gly Asn Ala Ala Gly Asn Ala Ala Gly Asn Ala Ala Gly Asn Ala Ala
            180                 185                 190

Gly Asn Asp Ala Gly Asn Ala Ala Gly Asn Ala Ala Gly Asn Ala Ala
        195                 200                 205

Gly Asn Ala Ala Gly Asn Ala Ala Gly Asn Ala Ala Gly Asn Ala Ala
    210                 215                 220

Gly Asn Ala Ala Gly Asn Ala Ala Gly Asn Ala Ala Gly Asn Asp Ala
225                 230                 235                 240

Gly Asn Ala Ala Gly Asn Ala Ala Gly Asn Ala Ala Gly Asn Ala Ala
                245                 250                 255

Gly Asn Ala Ala Gly Asn Ala Ala Gly Asn Ala Ala Gly Asn Ala Ala
            260                 265                 270

Gly Asn Ala Ala Gly Asn Ala Ala Gly Asn Ala Ala Gly Asn Ala Ala
        275                 280                 285

Gly Asn Ala Ala Gly Asn Ala Ala Gly Asn Ala Ala Gly Asn Ala Ala
    290                 295                 300

Gly Asn Ala Ala Gly Asn Ala Ala Gly Asn Glu Lys Ala Lys Asn Lys
305                 310                 315                 320

Asp Asn Lys Val Asp Ala Asn Thr Asn Lys Lys Asp Asn Gln Glu Glu
                325                 330                 335
```

```
Asn Asn Asp Ser Ser Asn Gly Pro Ser Glu Glu His Ile Lys Asn Tyr
            340                 345                 350

Leu Glu Ser Ile Arg Asn Ser Ile Thr Glu Glu Trp Ser Pro Cys Ser
        355                 360                 365

Val Thr Cys Gly Ser Gly Ile Arg Ala Arg Arg Lys Val Asp Ala Lys
    370                 375                 380

Asn Lys Lys Pro Ala Glu Leu Val Leu Ser Asp Leu Glu Thr Glu Ile
385                 390                 395                 400

Cys Ser Leu Asp Lys Cys Ser Ser Ile Phe Asn Val Val Ser Asn Ser
                405                 410                 415

Leu Gly Ile Val Leu Val Leu Val Leu Ile Leu Phe His
            420                 425

<210> SEQ ID NO 23
<211> LENGTH: 398
<212> TYPE: PRT
<213> ORGANISM: Plasmodium cynomolgi

<400> SEQUENCE: 23

Met Lys Asn Phe Ile Leu Leu Ala Val Ser Ser Ile Leu Leu Val Asp
1               5                   10                  15

Leu Phe Arg Thr Gln Trp Gly His Asn Val Asp Phe Ser Lys Ala Ile
            20                  25                  30

Asn Leu Asn Gly Val Ser Phe Asn Val Asp Ala Ser Ser Leu Gly
        35                  40                  45

Ala Ala Gln Val Arg Gln Ser Ala Ser Arg Gly Arg Gly Leu Gly Glu
    50                  55                  60

Asn Pro Lys Asn Glu Glu Gly Ala Asp Lys Pro Lys Lys Asp Glu
65                  70                  75                  80

Lys Gln Val Glu Pro Lys Lys Pro Arg Glu Asn Lys Leu Lys Gln Pro
                85                  90                  95

Ala Gly Asn Asn Ala Ala Ala Gly Glu Ala Gly Asn Asn Ala Ala Ala
            100                 105                 110

Gly Glu Ala Gly Asn Asn Ala Ala Ala Gly Glu Ala Gly Asn Asn Ala
        115                 120                 125

Ala Ala Gly Glu Ala Gly Asn Asn Ala Ala Gly Glu Ala Gly Asn
    130                 135                 140

Asn Ala Ala Ala Gly Glu Ala Gly Asn Asn Ala Ala Gly Gly Ala Ala
145                 150                 155                 160

Gly Asn Asn Ala Ala Ala Gly Glu Ala Gly Asn Asn Ala Ala Gly Gly
                165                 170                 175

Ala Ala Gly Asn Asn Ala Ala Ala Gly Glu Ala Gly Asn Asn Ala Ala
            180                 185                 190

Gly Gly Ala Ala Gly Asn Asn Ala Ala Gly Glu Ala Gly Asn Asn
        195                 200                 205

Ala Ala Gly Gly Ala Ala Gly Asn Asn Ala Ala Gly Glu Ala Gly
    210                 215                 220

Asn Asn Ala Ala Ala Gly Ala Ala Gly Asn Asn Ala Ala Gly Ala
225                 230                 235                 240

Ala Gly Asn Asn Ala Ala Ala Gly Glu Ala Gly Ala Gly Gly Ala Gly
                245                 250                 255

Arg Ala Gly Asn Asn Ala Ala Ala Gly Glu Ala Gly Ala Gly Gly Ala
            260                 265                 270

Gly Arg Ala Gly Asn Asn Ala Ala Ala Gly Glu Ala Gly Ala Gly Gly
```

```
            275                 280                 285
Ala Gly Gly Asn Ala Gly Asn Lys Lys Ala Gly Asp Ala Gly Gln Gly
    290                 295                 300

Gln Asn Asn Gly Gly Ala Asn Val Pro Asn Val Lys Leu Val Gln Glu
305                 310                 315                 320

Tyr Leu Asp Lys Ile Arg Ser Thr Ile Gly Val Glu Trp Ser Pro Cys
                325                 330                 335

Ser Val Thr Cys Gly Lys Gly Val Arg Met Arg Arg Lys Val Asn Ala
            340                 345                 350

Ala Asn Lys Lys Pro Glu Glu Leu Asp Ala Asn Asp Leu Glu Thr Glu
        355                 360                 365

Val Cys Thr Met Asp Lys Cys Ala Gly Ile Phe Asn Val Val Ser Asn
    370                 375                 380

Ser Leu Gly Leu Val Ile Leu Leu Val Leu Ala Leu Phe Asn
385                 390                 395

<210> SEQ ID NO 24
<211> LENGTH: 395
<212> TYPE: PRT
<213> ORGANISM: Plasmodium reichenowi

<400> SEQUENCE: 24

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Gly Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Ala Asp Asn
65                  70                  75                  80

Gly Asp Glu Gly Ile Asp Glu Asn Arg Arg His Arg Asn Lys Glu Gly
                85                  90                  95

Lys Glu Lys Leu Lys Lys Pro Lys His Asn Lys Leu Lys Gln Pro Gly
            100                 105                 110

Asn Asp Asn Val Asp Pro Asn Ala Asn Pro Asn Val Asp Pro Asn Ala
        115                 120                 125

Asn Pro Asn Val Asp Pro Asn Ala Asn Pro Asn Val Asp Pro Asn Ala
130                 135                 140

Asn Pro Asn Val Asp Pro Asn Ala Asn Pro Asn Val Asn Pro Asn Ala
145                 150                 155                 160

Asn Pro Asn Val Asp Pro Asn Ala Asn Pro Asn Val Asn Pro Asn Ala
                165                 170                 175

Asn Pro Asn Val Asn Pro Asn Ala Asn Pro Asn Val Asn Pro Asn Ala
            180                 185                 190

Asn Pro Asn Val Asn Pro Asn Ala Asn Pro Asn Val Asn Pro Asn Ala
        195                 200                 205

Asn Pro Asn Ala Asn Pro Asn Ala Asn Pro Asn Ala Asn Pro Asn Ala
    210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
                245                 250                 255
```

```
Asn Pro Asn Ala Asn Pro Asn Ala Asn Pro Asn Ala Asn Pro Asn Arg
                260                 265                 270

Asn Asn Glu Ala Asn Gly Gln Gly His Asn Lys Pro Asn Asp Gln Asn
            275                 280                 285

Arg Asn Val Asn Glu Asn Ala Asn Ala Asn Asn Ala Gly Arg Asn Asn
        290                 295                 300

Asn Asn Glu Glu Pro Ser Asp Lys His Ile Glu Glu Phe Leu Lys Gln
305                 310                 315                 320

Ile Pro Asn Asn Leu Ser Thr Glu Trp Ser Pro Cys Ser Val Thr Cys
                325                 330                 335

Gly Asn Gly Ile Gln Val Arg Ile Lys Pro Gly Ser Ala Gly Lys Pro
            340                 345                 350

Lys Asp Gln Leu Asp Tyr Glu Asn Asp Leu Glu Lys Lys Ile Cys Lys
        355                 360                 365

Met Glu Lys Arg Ser Ser Val Phe Asn Val Val Asn Ser Ser Ile Gly
370                 375                 380

Leu Ile Met Val Leu Ser Phe Leu Phe Leu Asn
385                 390                 395

<210> SEQ ID NO 25
<211> LENGTH: 340
<212> TYPE: PRT
<213> ORGANISM: Plasmodium berghei

<400> SEQUENCE: 25

Met Lys Lys Cys Thr Ile Leu Val Val Ala Ser Leu Leu Leu Val Asn
1               5                   10                  15

Ser Leu Leu Pro Gly Tyr Gly Gln Asn Lys Ser Ile Gln Ala Gln Arg
            20                  25                  30

Asn Leu Asn Glu Leu Cys Tyr Asn Glu Gly Asn Asp Asn Lys Leu Tyr
        35                  40                  45

His Val Leu Asn Ser Lys Asn Gly Lys Ile Tyr Asn Arg Asn Thr Val
    50                  55                  60

Asn Arg Leu Leu Ala Asp Ala Pro Glu Gly Lys Lys Asn Glu Lys Lys
65                  70                  75                  80

Asn Glu Lys Ile Glu Arg Asn Asn Lys Leu Lys Gln Pro Pro Pro Pro
                85                  90                  95

Pro Asn Pro Asn Asp Pro Pro Pro Asn Pro Asn Asp Pro Pro Pro Pro
            100                 105                 110

Pro Asn Pro Asn Asp Pro Pro Pro Asn Pro Asn Asp Pro Pro Pro Pro
            115                 120                 125

Pro Asn Ala Asn Asp Pro Pro Pro Asn Ala Asn Asp Pro Ala Pro Pro
            130                 135                 140

Pro Asn Ala Asn Asp Pro Ala Pro Pro Asn Ala Asn Asp Pro Ala Pro
145                 150                 155                 160

Pro Asn Ala Asn Asp Pro Ala Pro Pro Asn Ala Asn Asp Pro Pro Pro
                165                 170                 175

Pro Asn Pro Asn Asp Pro Ala Pro Pro Asn Ala Asn Asp Pro Pro Pro
            180                 185                 190

Pro Asn Pro Asn Asp Pro Ala Pro Pro Gln Gly Asn Asn Asn Pro Gln
            195                 200                 205

Pro Gln Pro Arg Pro Gln Pro Gln Pro Gln Pro Gln Pro Gln Pro Gln
        210                 215                 220

Pro Gln Pro Gln Pro Gln Pro Arg Pro Gln Pro Gln Pro Gln Pro Gly
225                 230                 235                 240
```

Gly Asn Asn Asn Lys Asn Asn Asn Asp Asp Ser Tyr Ile Pro
            245                 250                 255

Ser Ala Glu Lys Ile Leu Glu Phe Val Lys Gln Ile Arg Asp Ser Ile
            260                 265                 270

Thr Glu Glu Trp Ser Gln Cys Asn Val Thr Cys Gly Ser Gly Ile Arg
            275                 280                 285

Val Arg Lys Arg Lys Gly Ser Asn Lys Lys Ala Glu Asp Leu Thr Leu
            290                 295                 300

Glu Asp Ile Asp Thr Glu Ile Cys Lys Met Asp Lys Cys Ser Ser Ile
305                 310                 315                 320

Phe Asn Ile Val Ser Asn Ser Leu Gly Phe Val Ile Leu Leu Val Leu
            325                 330                 335

Val Phe Phe Asn
            340

<210> SEQ ID NO 26
<211> LENGTH: 427
<212> TYPE: PRT
<213> ORGANISM: Plasmodium yoelii

<400> SEQUENCE: 26

Met Lys Lys Cys Thr Ile Leu Val Val Ala Ser Leu Leu Leu Val Asp
1               5                   10                  15

Ser Leu Leu Pro Gly Tyr Gly Gln Asn Lys Ser Val Gln Ala Gln Arg
            20                  25                  30

Asn Leu Asn Glu Leu Cys Tyr Asn Glu Glu Asn Asp Asn Lys Leu Tyr
            35                  40                  45

His Val Leu Asn Ser Lys Asn Gly Lys Ile Tyr Asn Arg Asn Ile Val
            50                  55                  60

Asn Arg Leu Leu Gly Asp Ala Leu Asn Gly Lys Pro Glu Glu Lys Lys
65              70                  75                  80

Asp Asp Pro Pro Lys Asp Gly Asn Lys Asp Leu Pro Lys Glu Gly
            85                  90                  95

Lys Lys Asp Asp Leu Pro Lys Glu Glu Lys Lys Asp Asp Pro Pro Lys
            100                 105                 110

Asp Pro Lys Lys Asp Asp Pro Pro Lys Glu Ala Gln Asn Lys Leu Asn
            115                 120                 125

Gln Pro Val Val Ala Asp Glu Asn Val Asp Gln Gly Pro Gly Ala Pro
            130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
            165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
            195                 200                 205

Ala Pro Gln Gly Pro Gly Ala Pro Gln Gly Pro Gly Ala Pro Gln Gly
            210                 215                 220

Pro Gly Ala Pro Gln Gly Pro Gly Ala Pro Gln Gly Pro Gly Ala Pro
225                 230                 235                 240

Gln Gly Pro Gly Ala Pro Gln Gly Pro Gly Ala Pro Gln Gly Pro Gly
            245                 250                 255

Ala Pro Gln Gly Pro Gly Ala Pro Gln Gly Pro Gly Ala Pro Gln Gly

```
                260                 265                 270
Pro Gly Ala Pro Gln Gly Pro Ala Pro Gln Gly Pro Gly Ala Pro
            275                 280                 285

Gln Glu Pro Gln Gln Pro Pro Gln Gln Pro Pro Gln Gln Pro Pro
            290                 295                 300

Gln Gln Pro Pro Gln Gln Pro Pro Gln Gln Pro Pro Gln Gln Pro Arg
305                 310                 315                 320

Pro Gln Pro Asp Gly Asn Asn Asn Asn Asn Asn Asn Gly Asn Asn
                325                 330                 335

Asn Glu Asp Ser Tyr Val Pro Ser Ala Glu Gln Ile Leu Glu Phe Val
            340                 345                 350

Lys Gln Ile Ser Ser Gln Leu Thr Glu Glu Trp Ser Gln Cys Ser Val
            355                 360                 365

Thr Cys Gly Ser Gly Val Arg Val Arg Lys Arg Lys Asn Val Asn Lys
            370                 375                 380

Gln Pro Glu Asn Leu Thr Leu Glu Asp Ile Asp Thr Glu Ile Cys Lys
385                 390                 395                 400

Met Asp Lys Cys Ser Ser Ile Phe Asn Ile Val Ser Asn Ser Leu Gly
                405                 410                 415

Phe Val Ile Leu Leu Val Leu Val Phe Phe Asn
            420                 425

<210> SEQ ID NO 27
<211> LENGTH: 388
<212> TYPE: PRT
<213> ORGANISM: Plasmodiumgallinaceum

<400> SEQUENCE: 27

Met Lys Lys Leu Ala Ile Leu Ser Ala Ser Ser Phe Leu Phe Ala Asp
1               5                   10                  15

Phe Leu Phe Gln Glu Tyr Gln His Asn Gly Asn Tyr Lys Asn Phe Arg
            20                  25                  30

Leu Leu Asn Glu Val Cys Tyr Asn Asn Met Asn Ile Gln Leu Tyr Asn
        35                  40                  45

Glu Leu Glu Met Glu Asn Tyr Met Ser Asn Thr Tyr Phe Tyr Asn Asn
    50                  55                  60

Lys Lys Thr Ile Arg Leu Leu Gly Glu Asn Asp Asn Glu Ala Asn Val
65                  70                  75                  80

Asn Arg Ala Asn Asn Val Ala Asn Asp Asn Arg Ala Asn Gly Asn
                85                  90                  95

Arg Gly Asn Val Asn Arg Ala Asn Asp Arg Asn Ile Pro Tyr Phe Arg
            100                 105                 110

Glu Asn Val Val Asn Leu Asn Gln Pro Val Gly Gly Asn Gly Gly Val
        115                 120                 125

Gln Pro Ala Gly Gly Asn Gly Gly Val Gln Pro Ala Gly Gly Asn Gly
    130                 135                 140

Gly Val Gln Pro Ala Gly Gly Asn Gly Gly Val Gln Pro Ala Gly Gly
145                 150                 155                 160

Asn Gly Gly Val Gln Pro Ala Gly Gly Asn Gly Gly Val Gln Pro Ala
                165                 170                 175

Gly Gly Asn Gly Gly Val Gln Pro Ala Gly Gly Asn Gly Gly Ala Gln
            180                 185                 190

Pro Val Ala Ala Gly Gly Ala Gln Pro Val Val Ala Asp Gly Gly
        195                 200                 205
```

-continued

```
Val Gln Pro Leu Arg Gln Glu Gly Asp Ala Glu Asp Gly Gly Asn
        210                 215                 220
Gly Gly Ala Gln Pro Ala Gly Asn Gly Gly Ala Gln Pro Ala Gly
225                 230                 235                 240
Gly Asn Gly Gly Ala Gln Pro Ala Gly Asn Gly Gly Ala Gln Pro
                245                 250                 255
Ala Gly Gly Asn Gly Gly Ala Gln Pro Ala Gly Gly Asn Asp Ala Ala
                260                 265                 270
Lys Pro Asp Gly Gly Asn Asp Asp Lys Pro Glu Gly Gly Asp Glu
                275                 280                 285
Lys Ser Glu Glu Glu Lys Glu Asp Glu Pro Ile Pro Asp Pro Thr Gln
    290                 295                 300
Glu Glu Ile Asp Lys Tyr Leu Lys Ser Ile Leu Gly Asn Val Thr Ser
305                 310                 315                 320
Glu Trp Thr Asn Cys Asn Val Thr Cys Gly Lys Gly Ile Gln Ala Lys
                325                 330                 335
Ile Lys Ser Thr Ser Ala Asn Lys Lys Arg Glu Glu Ile Thr Pro Asn
                340                 345                 350
Asp Val Glu Val Lys Ile Cys Glu Leu Glu Arg Cys Ser Phe Ser Ile
                355                 360                 365
Phe Asn Val Ile Ser Asn Ser Leu Gly Leu Ala Ile Ile Leu Thr Phe
                370                 375                 380
Leu Phe Phe Tyr
385

<210> SEQ ID NO 28
<211> LENGTH: 8
<212> TYPE: PRT
<213> ORGANISM: Artificial Sequence
<220> FEATURE:
<223> OTHER INFORMATION: site for mutation

<400> SEQUENCE: 28

Gln Ser Ala Ser Arg Gly Arg Gly
1               5

<210> SEQ ID NO 29
<211> LENGTH: 8
<212> TYPE: PRT
<213> ORGANISM: Artificial Sequence
<220> FEATURE:
<223> OTHER INFORMATION: site after mutation

<400> SEQUENCE: 29

Gln Ser Ala Ser Ser Gly Ser Gly
1               5

<210> SEQ ID NO 30
<211> LENGTH: 4
<212> TYPE: PRT
<213> ORGANISM: Artificial Sequence
<220> FEATURE:
<223> OTHER INFORMATION: repeat region residues

<400> SEQUENCE: 30

Asn Ala Asn Pro
1

<210> SEQ ID NO 31
<211> LENGTH: 4
<212> TYPE: PRT
```

<213> ORGANISM: Artificial Sequence
<220> FEATURE:
<223> OTHER INFORMATION: minor repeat residues

<400> SEQUENCE: 31

Asn Val Asp Pro
1

<210> SEQ ID NO 32
<211> LENGTH: 4
<212> TYPE: PRT
<213> ORGANISM: Artificial Sequence
<220> FEATURE:
<223> OTHER INFORMATION: junction residues

<400> SEQUENCE: 32

Asn Pro Asp Pro
1

<210> SEQ ID NO 33
<211> LENGTH: 68
<212> TYPE: PRT
<213> ORGANISM: Artificial Sequence
<220> FEATURE:
<223> OTHER INFORMATION: C4b multimerization domain

<400> SEQUENCE: 33

Ser Gly Arg Ala His Ala Gly Trp Glu Thr Pro Glu Gly Cys Glu Gln
1               5                   10                  15

Val Leu Thr Gly Lys Arg Leu Met Gln Cys Leu Pro Asn Pro Glu Asp
            20                  25                  30

Val Lys Met Ala Leu Glu Val Tyr Lys Leu Ser Leu Glu Ile Glu Gln
        35                  40                  45

Leu Glu Leu Gln Arg Asp Ser Ala Arg Gln Ser Thr Leu Asp Lys Glu
    50                  55                  60

Leu Val Pro Arg
65

<210> SEQ ID NO 34
<211> LENGTH: 55
<212> TYPE: PRT
<213> ORGANISM: Artificial Sequence
<220> FEATURE:
<223> OTHER INFORMATION: C4b multimerization domain

<400> SEQUENCE: 34

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu
    50                  55

<210> SEQ ID NO 35
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 35

```
Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Ser Ala
        35                  40                  45

Arg Gln Ser Thr Leu Asp Lys Glu Leu
    50                  55

<210> SEQ ID NO 36
<211> LENGTH: 58
<212> TYPE: PRT
<213> ORGANISM: Artificial Sequence
<220> FEATURE:
<223> OTHER INFORMATION: C4b multimerization domain

<400> SEQUENCE: 36

Trp Glu Thr Pro Glu Gly Cys Glu Gln Val Leu Thr Gly Lys Arg Leu
1               5                   10                  15

Met Gln Cys Leu Pro Asn Pro Glu Asp Val Lys Met Ala Leu Glu Val
            20                  25                  30

Tyr Lys Leu Ser Leu Glu Ile Glu Gln Leu Glu Leu Gln Arg Asp Ser
        35                  40                  45

Ala Arg Gln Ser Thr Leu Asp Lys Glu Leu
    50                  55

<210> SEQ ID NO 37
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 37

Cys Glu Gln Val Leu Thr Gly Lys Arg Leu Met Gln Cys Leu Pro Asn
1               5                   10                  15

Pro Glu Asp Val Lys Met Ala Leu Glu Val Tyr Lys Leu Ser Leu Glu
            20                  25                  30

Ile Glu Gln Leu Glu Leu Gln Arg Asp Ser Ala Arg Gln Ser Thr Leu
        35                  40                  45

Asp Lys Glu Leu
    50

<210> SEQ ID NO 38
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 38

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Ser Ala
        35                  40                  45

Arg Gln Tyr Thr Leu Asp Lys Glu Leu
    50                  55
```

<210> SEQ ID NO 39
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 39

Glu Thr Pro Glu Gly Cys Glu Gln Val Leu Ala Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Arg Ala
        35                  40                  45

Arg Gln Ser Thr Leu Asp Lys Glu Leu
    50                  55

<210> SEQ ID NO 40
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 40

Glu Thr Pro Glu Gly Cys Glu Gln Val Leu Ala Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Arg Ala
        35                  40                  45

Arg Gln Ser Thr Trp Asp Lys Glu Leu
    50                  55

<210> SEQ ID NO 41
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 41

Glu Val Pro Glu Gly Cys Glu Gln Val Gln Ala Gly Arg Arg Leu Met
1               5                   10                  15

Gln Cys Leu Ala Asp Pro Tyr Glu Val Lys Met Ala Leu Glu Val Tyr
            20                  25                  30

Lys Leu Ser Leu Glu Ile Glu Leu Leu Glu Leu Gln Arg Asp Lys Ala
        35                  40                  45

Arg Lys Ser Ser Val Leu Arg Gln Leu
    50                  55

<210> SEQ ID NO 42
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 42

Val Val Pro Glu Gly Cys Glu His Ile Leu Lys Gly Arg Lys Thr Met
1               5                   10                  15

Gln Cys Leu Pro Asn Pro Glu Asp Val Lys Met Ala Leu Glu Ile Tyr 20                  25                  30

Lys Leu Ser Leu Asp Ile Glu Leu Leu Glu Leu Gln Arg Asp Arg Ala
        35                  40                  45

Lys Glu Ser Thr Val Gln Ser Pro Val
    50                  55

<210> SEQ ID NO 43
<211> LENGTH: 55
<212> TYPE: PRT
<213> ORGANISM: Artificial Sequence
<220> FEATURE:
<223> OTHER INFORMATION: C4b multimerization domain

<400> SEQUENCE: 43

Glu Val Pro Lys Asp Cys Glu His Val Phe Ala Gly Lys Lys Leu Met
1               5                   10                  15

Gln Cys Leu Pro Asn Ser Asn Asp Val Lys Met Ala Leu Glu Val Tyr
                20                  25                  30

Lys Leu Thr Leu Glu Ile Lys Gln Leu Gln Leu Gln Ile Asp Lys Ala
        35                  40                  45

Lys His Val Asp Arg Glu Leu
    50                  55

<210> SEQ ID NO 44
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 44

Glu Tyr Pro Glu Asp Cys Glu Gln Val His Glu Gly Lys Lys Leu Met
1               5                   10                  15

Gln Cys Leu Pro Asn Leu Glu Glu Ile Lys Leu Ala Leu Glu Leu Tyr
                20                  25                  30

Lys Leu Ser Leu Glu Thr Lys Leu Leu Glu Leu Gln Ile Asp Lys Glu
        35                  40                  45

Lys Lys Ala Lys Ala Lys Tyr Ser Ile
    50                  55

<210> SEQ ID NO 45
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 45

Glu Tyr Pro Glu Asp Cys Glu Gln Val His Glu Gly Lys Lys Leu Met
1               5                   10                  15

Glu Cys Leu Pro Thr Leu Glu Glu Ile Lys Leu Ala Leu Ala Leu Tyr
                20                  25                  30

Lys Leu Ser Leu Glu Thr Asn Leu Leu Glu Leu Gln Ile Asp Lys Glu
        35                  40                  45

Lys Lys Ala Lys Ala Lys Tyr Ser Thr
    50                  55

<210> SEQ ID NO 46
<211> LENGTH: 57
<212> TYPE: PRT
<213> ORGANISM: Artificial Sequence

```
<220> FEATURE:
<223> OTHER INFORMATION: C4b multimerization domain

<400> SEQUENCE: 46

Glu Ile Ala Glu Gly Cys Glu Gln Val Leu Ala Gly Arg Lys Ile Met
1               5                   10                  15

Gln Cys Leu Pro Lys Pro Glu Asp Val Arg Thr Ala Leu Glu Leu Tyr
            20                  25                  30

Lys Leu Ser Leu Glu Ile Lys Gln Leu Glu Lys Lys Leu Glu Lys Glu
        35                  40                  45

Glu Lys Cys Thr Pro Glu Val Gln Glu
    50                  55

<210> SEQ ID NO 47
<211> LENGTH: 67
<212> TYPE: PRT
<213> ORGANISM: Artificial Sequence
<220> FEATURE:
<223> OTHER INFORMATION: C4b multimerization domain

<400> SEQUENCE: 47

Glu Tyr Pro Glu Gly Cys Glu Gln Val Val Thr Gly Arg Lys Leu Leu
1               5                   10                  15

Gln Cys Leu Ser Arg Pro Glu Glu Val Lys Leu Ala Leu Glu Val Tyr
            20                  25                  30

Lys Leu Ser Leu Glu Ile Glu Ile Leu Gln Thr Asn Lys Leu Lys Lys
        35                  40                  45

Glu Ala Phe Leu Leu Arg Glu Arg Glu Lys Asn Val Thr Cys Asp Phe
    50                  55                  60

Asn Pro Glu
65

<210> SEQ ID NO 48
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 48

Glu Tyr Pro Glu Gly Cys Glu Gln Val Val Thr Gly Arg Lys Leu Leu
1               5                   10                  15

Lys Cys Leu Ser Arg Pro Glu Val Lys Leu Ala Leu Glu Val Tyr
            20                  25                  30

Lys Leu Ser Leu Glu Ile Ala Leu Glu Leu Gln Ile Asp Lys Pro
        35                  40                  45

Lys Asp Ala Ser
    50

<210> SEQ ID NO 49
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 49

Glu Val Pro Glu Asn Cys Glu Gln Val Ile Val Gly Lys Lys Leu Met
1               5                   10                  15

Lys Cys Leu Ser Asn Pro Asp Glu Ala Gln Met Ala Leu Gln Leu Tyr
            20                  25                  30
```

Lys Leu Ser Leu Glu Ala Glu Leu Leu Arg Leu Gln Ile Val Lys Ala
        35                  40                  45

Arg Gln Gly Ser
    50

<210> SEQ ID NO 50
<211> LENGTH: 54
<212> TYPE: PRT
<213> ORGANISM: Artificial Sequence
<220> FEATURE:
<223> OTHER INFORMATION: C4b multimerization domain

<400> SEQUENCE: 50

Glu Ala Ser Glu Asp Leu Lys Pro Ala Leu Thr Gly Asn Lys Thr Met
1               5                   10                  15

Gln Tyr Val Pro Asn Ser His Asp Val Lys Met Ala Leu Glu Ile Tyr
            20                  25                  30

Lys Leu Thr Leu Glu Val Glu Leu Leu Gln Leu Gln Ile Gln Lys Glu
        35                  40                  45

Lys His Thr Glu Ala His
    50

<210> SEQ ID NO 51
<211> LENGTH: 51
<212> TYPE: PRT
<213> ORGANISM: Artificial Sequence
<220> FEATURE:
<223> OTHER INFORMATION: C4b multimerization domain

<400> SEQUENCE: 51

Val Ser Ala Glu Val Cys Glu Ala Val Phe Lys Gly Gln Lys Leu Leu
1               5                   10                  15

Lys Cys Leu Pro Asn Ala Met Glu Val Lys Met Ala Leu Glu Val Tyr
            20                  25                  30

Lys Leu Ser Leu Glu Ile Glu Lys Leu Glu Gln Glu Lys Arg Lys Leu
        35                  40                  45

Glu Ile Ala
    50

<210> SEQ ID NO 52
<211> LENGTH: 66
<212> TYPE: PRT
<213> ORGANISM: Artificial Sequence
<220> FEATURE:
<223> OTHER INFORMATION: C4b multimerization domain

<400> SEQUENCE: 52

Glu Val Pro Glu Glu Cys Lys Gln Val Ala Ala Gly Arg Lys Leu Leu
1               5                   10                  15

Glu Cys Leu Pro Asn Pro Ser Asp Val Lys Met Ala Leu Glu Val Tyr
            20                  25                  30

Lys Leu Ser Leu Glu Ile Glu Gln Leu Glu Lys Glu Lys Tyr Val Lys
        35                  40                  45

Ile Gln Glu Lys Phe Ser Lys Lys Glu Met Lys Gln Leu Thr Ser Ala
    50                  55                  60

Leu His
65

<210> SEQ ID NO 53
<211> LENGTH: 59

```
<212> TYPE: PRT
<213> ORGANISM: Artificial Sequence
<220> FEATURE:
<223> OTHER INFORMATION: C4b multimerization domain

<400> SEQUENCE: 53

Glu Val Leu Glu Asp Cys Arg Ile Val Ser Arg Gly Ala Gln Leu Leu
1               5                   10                  15

His Cys Leu Ser Ser Pro Glu Asp Val His Arg Ala Leu Lys Val Tyr
            20                  25                  30

Lys Leu Phe Leu Glu Ile Glu Arg Leu Glu His Gln Lys Glu Lys Trp
        35                  40                  45

Ile Gln Leu His Arg Lys Pro Gln Ser Met Lys
    50                  55

<210> SEQ ID NO 54
<211> LENGTH: 63
<212> TYPE: PRT
<213> ORGANISM: Artificial Sequence
<220> FEATURE:
<223> OTHER INFORMATION: C4b multimerization domain

<400> SEQUENCE: 54

Glu Gly Pro Glu Asp Cys Glu Ile Val Asn Lys Gly Arg Gln Leu Leu
1               5                   10                  15

Gln Cys Leu Ser Ser Pro Glu Asp Val Gln Arg Ala Leu Glu Val Tyr
            20                  25                  30

Lys Leu Ser Leu Glu Ile Glu Arg Leu Glu Gln Gln Arg Glu Lys Arg
        35                  40                  45

Thr Ser Val His Arg Lys Ala His Tyr Thr Lys Val Asp Gly Pro
    50                  55                  60

<210> SEQ ID NO 55
<211> LENGTH: 67
<212> TYPE: PRT
<213> ORGANISM: Artificial Sequence
<220> FEATURE:
<223> OTHER INFORMATION: C4b multimerization domain

<400> SEQUENCE: 55

Glu Ala Pro Glu Gly Cys Glu Gln Val Leu Thr Gly Arg Lys Leu Met
1               5                   10                  15

Gln Cys Leu Pro Ser Pro Glu Asp Val Lys Val Ala Leu Glu Val Tyr
            20                  25                  30

Lys Leu Ser Leu Glu Ile Lys Gln Leu Glu Lys Glu Arg Asp Lys Leu
        35                  40                  45

Met Asn Thr His Gln Lys Phe Ser Gly Lys Glu Glu Met Lys Asp Leu
    50                  55                  60

Phe Phe Pro
65

<210> SEQ ID NO 56
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 56

Glu Val Pro Glu Gly Cys Glu Gln Val Leu Thr Gly Lys Lys Leu Met
1               5                   10                  15
```

-continued

Gln Cys Leu Pro Asn Pro Glu Asp Val Lys Met Ala Leu Glu Val Tyr
                20                  25                  30

Lys Leu Ser Leu Glu Ile Glu Leu Leu Glu Leu Gln Ile Asp Lys Ala
        35                  40                  45

Arg Gln Gly Ser
    50

<210> SEQ ID NO 57
<211> LENGTH: 47
<212> TYPE: PRT
<213> ORGANISM: Artificial Sequence
<220> FEATURE:
<223> OTHER INFORMATION: C4b multimerization domain

<400> SEQUENCE: 57

Gly Cys Glu Gln Val Leu Thr Gly Lys Arg Leu Met Gln Cys Leu Pro
1               5                   10                  15

Asn Pro Glu Asp Val Lys Met Ala Leu Glu Val Tyr Lys Leu Ser Leu
                20                  25                  30

Glu Ile Glu Gln Leu Glu Leu Gln Arg Asp Ser Ala Arg Gln Ser
        35                  40                  45

<210> SEQ ID NO 58
<211> LENGTH: 51
<212> TYPE: PRT
<213> ORGANISM: Artificial Sequence
<220> FEATURE:
<223> OTHER INFORMATION: C4b multimerization domain

<400> SEQUENCE: 58

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
                20                  25                  30

Lys Leu Ser Leu Glu Ile Glu Gln Leu Glu Leu Gln Arg Asp Ser Ala
        35                  40                  45

Arg Gln Ser
    50

<210> SEQ ID NO 59
<211> LENGTH: 53
<212> TYPE: PRT
<213> ORGANISM: Artificial Sequence
<220> FEATURE:
<223> OTHER INFORMATION: C4b multimerization domain

<400> SEQUENCE: 59

Gly Ser Glu Gln Val Leu Thr Gly Lys Arg Leu Met Gln Ser Leu Pro
1               5                   10                  15

Asn Pro Glu Asp Val Lys Met Ala Leu Glu Val Tyr Lys Leu Ser Leu
                20                  25                  30

Glu Ile Glu Gln Leu Glu Leu Gln Arg Asp Ser Ala Arg Gln Ser Thr
        35                  40                  45

Leu Asp Lys Glu Leu
    50

<210> SEQ ID NO 60
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 60

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Ile Tyr
            20                  25                  30

Lys Leu Thr Leu Glu Ile Glu Gln Leu Glu Leu Gln Arg Asp Ser Ala
        35                  40                  45

Arg Gln Ser Thr Leu Asp Lys Glu Leu
    50                  55

<210> SEQ ID NO 61
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 61

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Ile Tyr
            20                  25                  30

Lys Leu Ser Leu Glu Ile Lys Gln Leu Glu Leu Gln Arg Asp Ser Ala
        35                  40                  45

Arg Gln Ser Thr Leu Asp Lys Glu Leu
    50                  55

<210> SEQ ID NO 62
<211> LENGTH: 50
<212> TYPE: PRT
<213> ORGANISM: Artificial Sequence
<220> FEATURE:
<223> OTHER INFORMATION: C4b multimerization domain

<400> SEQUENCE: 62

Glu Gly Cys Glu Gln Ile Leu Thr Gly Lys Arg Leu Met Gln Cys Leu
1               5                   10                  15

Pro Asp Pro Glu Asp Val Lys Met Ala Leu Glu Ile Tyr Lys Leu Ser
            20                  25                  30

Leu Glu Ile Lys Gln Leu Glu Leu Gln Arg Asp Arg Ala Arg Gln Ser
        35                  40                  45

Thr Leu
    50

<210> SEQ ID NO 63
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 63

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Lys Gln Leu Glu Leu Gln Arg Asp Arg Ala
        35                  40                  45

Arg Gln Ser Thr Leu Asp Lys Glu Leu

-continued 50                  55

<210> SEQ ID NO 64
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 64

Glu Gly Cys Glu Gln Ile Leu Thr Gly Lys Arg Leu Met Gln Cys Leu
1               5                   10                  15

Pro Asn Pro Glu Asp Val Lys Met Ala Leu Glu Ile Tyr Lys Leu Ser
            20                  25                  30

Leu Glu Ile Glu Gln Leu Glu Leu Gln Arg Asp Arg Ala Arg Gln Ser
        35                  40                  45

Thr Leu Asp Lys
    50

<210> SEQ ID NO 65
<211> LENGTH: 61
<212> TYPE: PRT
<213> ORGANISM: Artificial Sequence
<220> FEATURE:
<223> OTHER INFORMATION: C4b multimerization domain

<400> SEQUENCE: 65

Trp Glu Thr Pro Glu Gly Cys Glu Gln Val Leu Thr Gly Lys Arg Leu
1               5                   10                  15

Met Gln Cys Leu Pro Asn Pro Glu Asp Val Lys Met Ala Leu Glu Val
            20                  25                  30

Tyr Lys Leu Ser Leu Glu Ile Glu Gln Leu Glu Leu Gln Arg Asp Ser
        35                  40                  45

Ala Arg Gln Ser Thr Leu Asp Lys Glu Leu Val Pro Arg
    50                  55                  60

<210> SEQ ID NO 66
<211> LENGTH: 62
<212> TYPE: PRT
<213> ORGANISM: Homo sapiens

<400> SEQUENCE: 66

Ala His Ala Gly Trp Glu Thr Pro Glu Gly Cys Glu Gln Val Leu Thr
1               5                   10                  15

Gly Lys Arg Leu Met Gln Cys Leu Pro Asn Pro Glu Asp Val Lys Met
            20                  25                  30

Ala Leu Glu Val Tyr Lys Leu Ser Leu Glu Ile Glu Gln Leu Glu Leu
        35                  40                  45

Gln Arg Asp Ser Ala Arg Gln Ser Thr Leu Asp Lys Glu Leu
    50                  55                  60

<210> SEQ ID NO 67
<211> LENGTH: 56
<212> TYPE: PRT
<213> ORGANISM: Gallus gallus

<400> SEQUENCE: 67

Ser Lys Lys Gln Gly Asp Ala Asp Val Cys Gly Glu Val Ala Tyr Ile
1               5                   10                  15

Gln Ser Val Val Ser Asp Cys His Val Pro Thr Glu Asp Val Lys Thr
            20                  25                  30

Leu Leu Glu Ile Arg Lys Leu Phe Leu Glu Ile Gln Lys Leu Lys Val
        35                  40                  45

Glu Leu Gln Gly Leu Ser Lys Glu
    50                  55

<210> SEQ ID NO 68
<211> LENGTH: 56
<212> TYPE: PRT
<213> ORGANISM: Artificial Sequence
<220> FEATURE:
<223> OTHER INFORMATION: modified heptamerization domain from Gallus
      gallus

<400> SEQUENCE: 68

Ser Lys Lys Gln Gly Asp Ala Asp Val Cys Gly Glu Val Ala Tyr Ile
1               5                   10                  15

Gln Ser Val Val Ser Asp Cys His Val Pro Thr Ala Glu Leu Arg Thr
            20                  25                  30

Leu Leu Glu Ile Arg Lys Leu Phe Leu Glu Ile Gln Lys Leu Lys Val
        35                  40                  45

Glu Leu Gln Gly Leu Ser Lys Glu
    50                  55

<210> SEQ ID NO 69
<211> LENGTH: 4
<212> TYPE: PRT
<213> ORGANISM: Artificial Sequence
<220> FEATURE:
<223> OTHER INFORMATION: linker
<220> FEATURE:
<221> NAME/KEY: MOD_RES
<222> LOCATION: (1)..(1)
<223> OTHER INFORMATION: ACETYLATION

<400> SEQUENCE: 69

Cys Gly Gly Gly
1

<210> SEQ ID NO 70
<211> LENGTH: 18
<212> TYPE: PRT
<213> ORGANISM: Artificial Sequence
<220> FEATURE:
<223> OTHER INFORMATION: linker

<400> SEQUENCE: 70

Gly Ser Thr Ser Gly Ser Gly Lys Pro Gly Ser Gly Glu Gly Ser Thr
1               5                   10                  15

Lys Gly

<210> SEQ ID NO 71
<211> LENGTH: 7
<212> TYPE: PRT
<213> ORGANISM: Artificial Sequence
<220> FEATURE:
<223> OTHER INFORMATION: linker

<400> SEQUENCE: 71

Ser Gly Arg Ala His Ala Gly
1               5

<210> SEQ ID NO 72
<211> LENGTH: 21
<212> TYPE: PRT

```
<213> ORGANISM: Artificial Sequence
<220> FEATURE:
<223> OTHER INFORMATION: T2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 72

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 73
<211> LENGTH: 22
<212> TYPE: PRT
<213> ORGANISM: Artificial Sequence
<220> FEATURE:
<223> OTHER INFORMATION: P2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 73

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 74
<211> LENGTH: 24
<212> TYPE: PRT
<213> ORGANISM: Artificial Sequence
<220> FEATURE:
<223> OTHER INFORMATION: E2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 74

Gly Ser Gly Gln Cys Thr Asn Tyr Ala Leu Leu Lys Leu Ala Gly Asp
1               5                   10                  15

Val Glu Ser Asn Pro Gly Pro Pro
            20

<210> SEQ ID NO 75
<211> LENGTH: 25
<212> TYPE: PRT
<213> ORGANISM: Artificial Sequence
<220> FEATURE:
<223> OTHER INFORMATION: F2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 75

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 76
<211> LENGTH: 14
<212> TYPE: PRT
<213> ORGANISM: Artificial Sequence
<220> FEATURE:
<223> OTHER INFORMATION: mutant circumsporozoite protein (CSP)

<400> SEQUENCE: 76

Ser Leu Ser Ser Asn Ser Ala Ser Leu Gly Glu Asn Asp Asp
1               5                   10

<210> SEQ ID NO 77
<211> LENGTH: 337
<212> TYPE: PRT
<213> ORGANISM: Artificial Sequence
<220> FEATURE:
<223> OTHER INFORMATION: DeltaN-CSP

<400> SEQUENCE: 77

Ser Leu Gly Glu Asn Asp Asp Gly Asn Asn Glu Asp Asn Glu Lys Leu
1               5                   10                  15

Arg Lys Pro Lys His Lys Lys Leu Lys Gln Pro Ala Asp Gly Asn Pro
                20                  25                  30

Asp Pro Asn Ala Asn Pro Asn Val Asp Pro Asn Ala Asn Pro Asn Val
            35                  40                  45

Asp Pro Asn Ala Asn Pro Asn Val Asp Pro Asn Ala Asn Pro Asn Ala
        50                  55                  60

Asn Pro Asn Ala Asn Pro Asn Ala Asn Pro Asn Ala Asn Pro Asn Ala
65                  70                  75                  80

Asn Pro Asn Ala Asn Pro Asn Ala Asn Pro Asn Ala Asn Pro Asn Ala
                85                  90                  95

Asn Pro Asn Ala Asn Pro Asn Ala Asn Pro Asn Ala Asn Pro Asn Ala
            100                 105                 110

Asn Pro Asn Ala Asn Pro Asn Ala Asn Pro Asn Ala Asn Pro Asn Val
            115                 120                 125

Asp Pro Asn Ala Asn Pro Asn Ala Asn Pro Asn Ala Asn Pro Asn Ala
        130                 135                 140

Asn Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
                165                 170                 175

Asn Pro Asn Ala Asn Pro Asn Ala Asn Pro Asn Ala Asn Pro Asn Ala
            180                 185                 190

Asn Pro Asn Ala Asn Pro Asn Ala Asn Pro Asn Lys Asn Asn Gln Gly
            195                 200                 205

Asn Gly Gln Gly His Asn Met Pro Asn Asp Pro Asn Arg Asn Val Asp
        210                 215                 220

Glu Asn Ala Asn Ala Asn Ser Ala Val Lys Asn Asn Asn Asn Glu Glu
225                 230                 235                 240

Pro Ser Asp Lys His Ile Lys Glu Tyr Leu Asn Lys Ile Gln Asn Ser
                245                 250                 255

Leu Ser Thr Glu Trp Ser Pro Cys Ser Val Thr Cys Gly Asn Gly Ile
            260                 265                 270

Gln Val Arg Ile Lys Pro Gly Ser Ala Asn Lys Pro Lys Asp Glu Leu
        275                 280                 285

Asp Tyr Ala Asn Asp Ile Glu Lys Lys Ile Cys Lys Met Glu Lys Cys

```
                  290                 295                 300

Ser Gly Ser Gly Leu Asn Asp Ile Phe Glu Ala Gln Lys Ile Glu Trp
305                 310                 315                 320

His Glu Leu Glu Val Leu Phe Gln Gly Pro Gly His His His His His
                325                 330                 335

His
```

<210> SEQ ID NO 78
<211> LENGTH: 277
<212> TYPE: PRT
<213> ORGANISM: Artificial Sequence
<220> FEATURE:
<223> OTHER INFORMATION: DeltaN-CSP-5/3

<400> SEQUENCE: 78

```
Ser Leu Gly Glu Asn Asp Asp Gly Asn Asn Glu Asp Asn Glu Lys Leu
1               5                   10                  15

Arg Lys Pro Lys His Lys Lys Leu Lys Gln Pro Ala Asp Gly Asn Pro
                20                  25                  30

Asp Pro Asn Ala Asn Pro Asn Val Asp Pro Asn Ala Asn Pro Asn Val
            35                  40                  45

Asp Pro Asn Ala Asn Pro Asn Val Asp Pro Asn Ala Asn Pro Asn Ala
        50                  55                  60

Asn Pro Asn Ala Asn Pro Asn Ala Asn Pro Asn Ala Asn Pro Asn Ala
65                  70                  75                  80

Asn Pro Asn Ala Asn Pro Asn Ala Asn Pro Asn Ala Asn Pro Asn Ala
                85                  90                  95

Asn Pro Asn Ala Asn Pro Asn Ala Asn Pro Asn Ala Asn Pro Asn Ala
            100                 105                 110

Asn Pro Asn Ala Asn Pro Asn Ala Asn Pro Asn Ala Asn Pro Asn Val
        115                 120                 125

Asp Pro Asn Ala Asn Pro Asn Ala Asn Pro Asn Ala Asn Pro Asn Lys
    130                 135                 140

Asn Asn Gln Gly Asn Gly Gln Gly His Asn Met Pro Asn Asp Pro Asn
145                 150                 155                 160

Arg Asn Val Asp Glu Asn Ala Asn Ala Asn Ser Ala Val Lys Asn Asn
                165                 170                 175

Asn Asn Glu Glu Pro Ser Asp Lys His Ile Lys Glu Tyr Leu Asn Lys
            180                 185                 190

Ile Gln Asn Ser Leu Ser Thr Glu Trp Ser Pro Cys Ser Val Thr Cys
        195                 200                 205

Gly Asn Gly Ile Gln Val Arg Ile Lys Pro Gly Ser Ala Asn Lys Pro
    210                 215                 220

Lys Asp Glu Leu Asp Tyr Ala Asn Asp Ile Glu Lys Lys Ile Cys Lys
225                 230                 235                 240

Met Glu Lys Cys Ser Gly Ser Gly Leu Asn Asp Ile Phe Glu Ala Gln
                245                 250                 255

Lys Ile Glu Trp His Glu Leu Glu Val Leu Phe Gln Gly Pro Gly His
            260                 265                 270

His His His His His
        275
```

<210> SEQ ID NO 79
<211> LENGTH: 257
<212> TYPE: PRT
<213> ORGANISM: Artificial Sequence

```
<220> FEATURE:
<223> OTHER INFORMATION: DeltaN-CSP-19/3

<400> SEQUENCE: 79

Ser Leu Gly Glu Asn Asp Asp Gly Asn Asn Glu Asp Asn Glu Lys Leu
1               5                   10                  15

Arg Lys Pro Lys His Lys Lys Leu Lys Gln Pro Ala Asp Gly Asn Pro
            20                  25                  30

Asp Pro Asn Ala Asn Pro Asn Val Asp Pro Asn Ala Asn Pro Asn Val
                35                  40                  45

Asp Pro Asn Ala Asn Pro Asn Val Asp Pro Asn Ala Asn Pro Asn Ala
            50                  55                  60

Asn Pro Asn Ala Asn Pro Asn Ala Asn Pro Asn Ala Asn Pro Asn Ala
65                  70                  75                  80

Asn Pro Asn Ala Asn Pro Asn Ala Asn Pro Asn Ala Asn Pro Asn Ala
                85                  90                  95

Asn Pro Asn Ala Asn Pro Asn Ala Asn Pro Asn Ala Asn Pro Asn Ala
                100                 105                 110

Asn Pro Asn Ala Asn Pro Asn Ala Asn Pro Lys Asn Asn Gln Gly
                115                 120                 125

Asn Gly Gln Gly His Asn Met Pro Asn Asp Pro Asn Arg Asn Val Asp
            130                 135                 140

Glu Asn Ala Asn Ala Asn Ser Ala Val Lys Asn Asn Asn Glu Glu
145                 150                 155                 160

Pro Ser Asp Lys His Ile Lys Glu Tyr Leu Asn Lys Ile Gln Asn Ser
                165                 170                 175

Leu Ser Thr Glu Trp Ser Pro Cys Ser Val Thr Cys Gly Asn Gly Ile
            180                 185                 190

Gln Val Arg Ile Lys Pro Gly Ser Ala Asn Lys Pro Lys Asp Glu Leu
            195                 200                 205

Asp Tyr Ala Asn Asp Ile Glu Lys Lys Ile Cys Lys Met Glu Lys Cys
            210                 215                 220

Ser Gly Ser Gly Leu Asn Asp Ile Phe Glu Ala Gln Lys Ile Glu Trp
225                 230                 235                 240

His Glu Leu Glu Val Leu Phe Gln Gly Pro Gly His His His His His
                245                 250                 255

His
```